United States Patent
Tanaka et al.

[19]

[11] Patent Number: 6,103,736
[45] Date of Patent: Aug. 15, 2000

[54] FUSED IMIDAZO[1,2-A]PYRIDINES

[75] Inventors: Hironori Tanaka; Kazuyoshi Fukuzumi; Takeshi Togawa; Kimiko Banno; Toshihisa Ushiro; Masaaki Morii; Takafumi Nakatani, all of Osaka, Japan

[73] Assignee: Shinnippon Pharmaceutical Inc., Osaka, Japan

[21] Appl. No.: 09/340,737

[22] Filed: Jun. 29, 1999

Related U.S. Application Data

[62] Division of application No. 08/945,326, Oct. 21, 1997, Pat. No. 6,020,342.

[30] Foreign Application Priority Data

Apr. 21, 1995 [JP] Japan ........................... 7-97130

[51] Int. Cl.[7] .......................... A01N 43/42; A61K 31/44; C07D 471/00; C07D 491/00; C07D 235/02
[52] U.S. Cl. ........................... 514/292; 514/294; 546/87; 548/302.1
[58] Field of Search ..................... 514/292, 294; 546/87; 548/302.1

[56] References Cited

U.S. PATENT DOCUMENTS

| 4,468,400 | 8/1984 | Gold et al. ............. | 424/256 |
|---|---|---|---|
| 4,507,294 | 3/1985 | Bristol et al. ........... | 514/249 |
| 4,686,227 | 8/1987 | Ueda et al. ............. | 514/292 |
| 4,725,601 | 2/1988 | Ueda et al. ............. | 514/249 |

FOREIGN PATENT DOCUMENTS

| 0 033 094 | 8/1981 | European Pat. Off. . |
|---|---|---|
| 0 068 378 | 1/1983 | European Pat. Off. . |
| 0 165 545 | 12/1985 | European Pat. Off. . |
| 0 204 285 | 12/1986 | European Pat. Off. . |
| 0 266 890 | 5/1988 | European Pat. Off. . |
| 30 46 510 | 10/1981 | Germany . |
| 56-113782 | 9/1981 | Japan . |
| 58-13584 | 1/1983 | Japan . |
| 62-16483 | 1/1987 | Japan . |

*Primary Examiner*—Richard L. Raymond
*Assistant Examiner*—Tamthom N. Truong
*Attorney, Agent, or Firm*—Foley & Lardner

[57] ABSTRACT

Compounds of the formula:

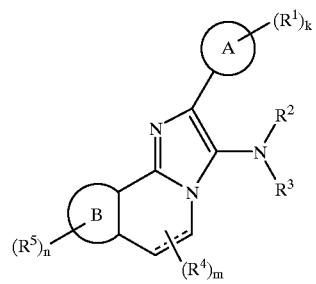

(I)

which are useful as anti-ulcer agent are provided.

12 Claims, No Drawings

FUSED IMIDAZO[1,2-A]PYRIDINES

This application is a divisional of application Ser. No. 8/945,326, filed Oct. 21, 1997 now U.S. Pat. No. 6,020,342.

FIELD OF THE INVENTION

The present invention relates to novel fused imidazo[1,2-a]pyridines and medicaments containing them. More particularly, it relates to fused imidazo[1,2-a]pyridines useful for treatment of peptic ulcers, which are characterized by having a (hetero)aryl group on the 2-position and an amino group on the 3-position, and pharmaceutically acceptable salts or solvates thereof, and pharmaceutical compositions containing them.

BACKGROUND OF THE INVENTION

It has been explained that peptic ulcers like gastric and duodenal ulcers are developed due to collapse of balance between aggressive factors (gastric acid, pepsin, etc.) and defensive factors (blood flow, mucus, mucosal resistance, mucosal protection, etc.). Peptic ulcers are usually subjected to medical treatment, and various medications are applied thereto. The drugs for peptic ulcer therapy may be divided into two types, one being inhibitors of aggressive factors, the other being promoters of defensive factors, and they are used properly according to the type of diseases. Currently, histamine $H_2$-blockers (e.g. cimetidine, ranitidine, etc.) are generally used in the clinical stage as inhibitors against aggressive factors. However, it has been reported that there are refractory ulcers, and that the $H_2$-blockers possess adverse side effects, such as antiandrogen action and inhibitory action against liver metabolizing enzymes. Recently, it has been found that $H^+/K^+$-ATPase is associated with the final step for acid secretion, and it has been suggested that benzimidazoles having inhibitory action on this enzyme, such as omeprazole, are useful as anti-ulcer drugs. However, palindromia of ulcer is a problem remained unsolved. Furthermore, other problems requiring an improvement exist, such as development of carcinoid, and an interaction with other drugs, which decreases liver clearances for diazepam and fenitoin. On the other hand, it is well-known that the promoters of defensive factors show limited healing rate as compared with the inhibitors of aggressive factors, and that the former provides delayed disappearance of subjective symptom. Thus, anti-ulcer drugs presently available are not satisfactory, and development of promising new anti-ulcer drugs has being desired.

The purpose of the present invention is to find compounds having both inhibitory action against aggressive factors and promoting action on mucosal defensive factors, and to provide more promising anti-ulcer drugs.

European Patent Publication No. 0165545 and U.S. Pat. No. 4,468,400 disclose tricyclic compounds which have similar structures to the compounds of the present invention. However, they don't disclose compounds which have the same substituents as the substituents on the compounds of the present invention. European Patent Publications No. 0033094, No. 0068378 and No. 0204285 disclose non-fused imidazo[1,2-a]pyridines which, on account of their antisecretory and cytoprotective actions, are intended to use for the treatment of ulcer.

DETAILED DESCRIPTION

The present inventors have now discovered, after extensive studies, that novel fused imidazo[1,2-a]pyridines bearing a (hetero)aryl group on the 2-position and an amino group on the 3-position, and pharmaceutically acceptable salts or solvates thereof have noteworthy pharmacological properties and they are advantageously different from known imidazo[1,2-a]pyridines above-noted in their pharmacological activities. The present invention is based on such findings.

Accordingly, one object of the present invention is to provide novel fused imidazo[1,2-a]pyridines and pharmaceutically acceptable salts or solvates thereof, which show an inhibitory action on gastric acid secretion and a protective action of gastric mucosa.

Another object of the invention is to provide pharmaceutical compositions comprising, as an active ingredient, said fused imidazo[1,2-a]pyridine, or a pharmaceutically acceptable salt or solvate thereof.

The compound of the invention is represented by the following general formula (1):

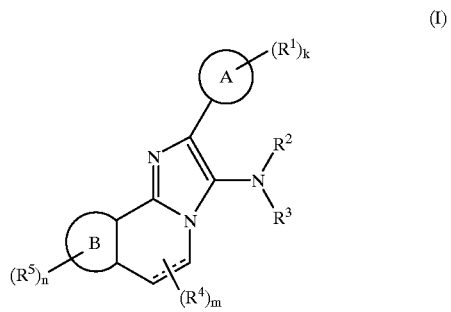

wherein ring A and ring B each independently represent an aromatic ring selected from benzene, thiophene, furan or pyrrole ring; $R^1$ is hydroxyl group, halogen atom, lower alkyl group which may be halogenated, lower alkoxy group or acyloxy group, k represents 0, 1, 2 or 3; $R^2$ and $R^3$ may be the same or different and each represent hydrogen atom, alkenyl group, acyl group, alkoxycarbonyl group or lower alkyl group which may have substituent(s) selected from the group consisting of 1) halogen atom, 2) hydroxyl group, 3) lower alkoxy group, 4) lower alkylthio group, 5) alkylsulfinyl group, 6) alkoxycarbonyl group, 7) carbamoyl group, 8) alkylamino group and 9) aryl group, or $R^2$ and $R^3$, together with the nitrogen atom to which they are attached, may form a 5- or 6-membered monocyclic heterocyclic ring, or $R^2$ and $R^3$, together with the nitrogen atom to which they are attached, may form an alkylideneamino group or arylalkylideneamino group; $R^4$ and $R^5$ each independently represent halogen atom, cyano group, hydroxyl group, carboxyl group, alkoxycarbonyl group, acyl group, alkylamino group, aryl group, acyloxy group, carbamoyloxy group, lower alkyl group which may have substituent(s) selected from the group consisting of 1) hydroxyl group, 2) lower alkoxy group, 3) aryl group and 4) aryloxy group, lower alkoxy group which may have substituent(s) selected from the group consisting of 1) hydroxyl group, 2) lower alkoxy group, 3) lower alkoxycarbonyl group and 4) aryl group, or lower alkylthio group which may be substituted with aryl group; m represents 0, 1 or 2; n represents 0, 1 or 2; the dotted line, together with the solid line, represents a single or double bond, provided that plural $R^4$s may be attached to the same carbon atom.

The terms used herein are defined below. Substituents on the compounds(I) of the present invention have the following significances, whether the substituents exist alone or constitute part of other group.

"Benzene, thiophene, furan or pyrrole ring represented by ring A" are shown below.

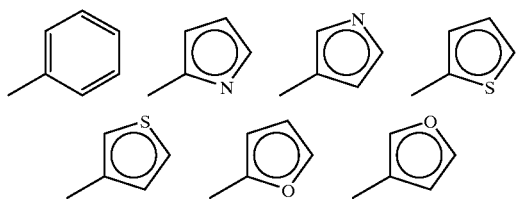

"Benzene, thiophene, furan or pyrrole ring represented by ring B" are shown below.

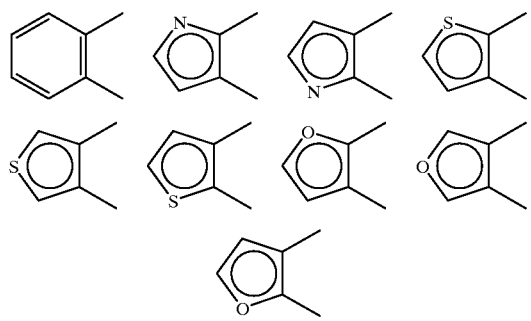

"Halogen atom" may include a fluorine atom, a chlorine atom, a bromine atom and an iodine atom.

"Lower alkyl group" means straight, branched or cyclic alkyl group having 1 to 6 carbon atoms, and may include, for example, methyl group, ethyl group, propyl group, isopropyl group, butyl group, isobutyl group, sec-butyl group, tert-butyl group, pentyl group, isopentyl group, neopentyl group, tert-pentyl group, 1-methylbutyl group, 2-methylbutyl group, 1,2-dimethylpropyl group, hexyl group, isohexyl group, 1-methylpentyl group, 2-methylpentyl group, 3-methylpentyl group, 1,1-dimethylbutyl group, 1,2-dimethylbutyl group, 2,2-dimethylbutyl group, 1,3-dimethylbutyl group, 2,3-dimethylbutyl group, 3,3-dimethylbutyl group, 1-ethylbutyl group, 2-ethylbutyl group, 1,2,2-trimethylpropyl group, 1-ethyl-1-methylpropyl group, 1-ethyl-2-methylpropyl group, cyclopropyl group, cyclobutyl group, cyclopentyl group, 2-methylcyclopentyl group, cyclohexyl group and the like. Preferable lower alkyl groups include an alkyl group having 1 to 4 carbon atoms, in particular, lower alkyl group having 1 to 3 carbon atoms.

"Acyl group" may include a residue of an organic acid such as aliphatic saturated carboxylic acid, aliphatic unsaturated carboxylic acid and arylcarboxylic acid, and specific examples are lower alkanoyl group carrying, for example, formyl group, acetyl group, propionyl group, butyryl group, isobutyryl group, hexanoyl group, bromoacetyl group, trifluoroacetyl group, methoxyacetyl group, butoxyacetyl group, phenoxyacetyl group, 4-bromomethylphenylacetyl group, 4-methoxyphenylacetyl group, 1-naphthylacetyl group, 3-pyridylacetyl group, 3-chloropropionyl group, 3-bromopropionyl group, 3-(methylthio)propionyl group, 3-ethoxypropionyl group, 3-(3,4-dimethoxyphenyl) propionyl group, 3-carboxypropionyl group, 3-benzoylpropionyl group, 4-chlorobutyryl group, 3-acetylbutyryl group, succinyl group, cyclopentylacetyl group, 6-bromohexanoyl group and the like; lower alkenoyl group carrying, for example, acryloyl group, 2-furylacryloyl group, crotonoyl group, 3-methylcrotonoyl group, cinnamoyl group, 4-methoxycinnamoyl group, methoxymaleoyl group, methoxyfumaroyl group and the like; arylcarbonyl group such as benzoyl group, 4-pentylbenzoyl group, p-anisoyl group, o-anisoyl group, 3,5-bis(trifluoromethyl) benzoyl group, 4-bromobenzoyl group, 4-butoxybenzoyl group, 4-chlorobenzoyl group, 3-chlorobenzoyl group, 4-chloromethylbenzoyl group, 4-cyanobenzoyl group, 3,4-dichlorobenzoyl group, 3,5-dichlorobenzoyl group, 2,4-difluorobenzoyl group, 3,4-dimethoxybenzoyl group, 4-ethoxybenzoyl group, 3-fluorobenzoyl group, 4-isopropylbenzoyl group, 3-(trifluoromethyl)benzoyl group, 3,4,5-trimethoxybenzoyl group, 3,4-dimethylbenzoyl group, m-toluoyl group, o-toluoyl group, p-toluoyl group, 1-naphthoyl group, 2-naphthoyl group, 1-bromo-2-naphthoyl group and the like; or heteroarylcarbonyl group such as 2-thenoyl group, 3-thenoyl group, 5-methyl-2-thenoyl group, 2-furoyl group, 5-bromo-2-furoyl group, nicotinoyl group, isonicotinoyl group, 6-methylpicolinoyl group, 3-methyl-2-benzo[b]furoyl group, quinoline-2-carbonyl group and the like. Preferable acyl groups are residues of aliphatic carboxylic acids, in particular, residues of aliphatic saturated carboxylic acids.

"Alkenyl group" means straight or branched alkenyl group having 2 to 6 carbon atoms, and may include, for example vinyl group, allyl group, 1-propenyl group, isopropenyl group, 2-methyl-1-propenyl group, 1-butenyl group, 2-butenyl group, 3-butenyl group, 2-ethyl-i-butenyl group, 3-methyl-2-butenyl group, 1,3-butadienyl group, 1-pentenyl group, 2-pentenyl group, 3-pentenyl group, 4-pentenyl group, 4-methyl-3-pentenyl group, 1-hexenyl group, 2-hexenyl group, 3-hexenyl group, 4-hexenyl group, 5-hexenyl group and the like. Preferable alkenyl groups are alkenyl groups having 2 to 3 carbon atoms.

"Lower alkoxy group" means alkoxy group having 1 to 6 carbon atoms, such as methoxy group, ethoxy group, propoxy group, isopropoxy group, butoxy group, isobutoxy group, sec-butoxy group, tert-butoxy group, pentyloxy group, isopentyloxy group, neopentyloxy group, tert-pentyloxy group, 1-methylbutoxy group, 2-methylbutoxy group, 1,2-dimethylpropoxy group, hexyloxy group, isohexyloxy group, 1-methylpentyloxy group, 2-methylpentyloxy group, 3-methylpentyloxy group, 1-ethylbutoxy group, 2-ethylbutoxy group, 1,2,2,-trimethylpropoxy group, 1-ethyl-1-methylpropoxy group, 1-ethyl-2-methylpropoxy group and the like. Preferable alkoxy groups are alkoxy groups having 1 to 4 carbon atoms, in particular, alkoxy groups having 1 to 3 carbon atoms.

"Lower alkylthio group" may include methylthio group, ethylthio group, propylthio group, isopropylthio group, butylthio group, isobutylthio group, sec-butylthio group, tert-butylthio group, pentylthio group, isopentylthio group, neopentylthio group, tert-pentylthio group, 1-methylbutylthio group, 2-methylbutylthio group and the like.

"Alkylsulfinyl group" means the above-mentioned "alkyl group" to which a sulfinyl group is bonded, and it may include, for example, methylsulfinyl group, ethylsulfinyl group, isopropylsulfinyl group, butylsulfinyl group and the like.

"Lower alkoxycarbonyl group" means the above-mentioned "lower alkoxy group" to which a carbonyl group is bonded, and it may include, for example, methoxycarbonyl group, ethoxycarbonyl group, propoxycarbonyl group, isopropoxycarbonyl group, butoxycarbonyl group, isobutoxycarbonyl group, sec-butoxycarbonyl group, tert-butoxycarbonyl group, pentyloxycarbonyl group, isopentyloxycarbonyl group, 3-methylpentyloxycarbonyl group, 2,3- dimethylbutoxycarbonyl group, 3,3-dimethylbutoxycarbonyl group, 2-ethylbutoxycarbonyl group and the like.

"Carbamoyl group" may include carbamoyl group, dimethylcarbamoyl group, ethylcarbamoyl group, diethylcarbamoyl group, allylcarbamoyl group, cyclopentylcarbamoyl group, hexylcarbamoyl group, N-(4-ethoxycarbonyloxyphenyl)carbamoyl group, N-(4-trifluoromethylphenyl)carbamoyl group and the like.

"Alkylamino group" may include methylamino group, ethylamino group, dimethylamino group, diethylamino group, dipropylamino group, N-methyl-N-ethylaamino group, N-methyl-N-propylamino group, N-ethyl-N-propylamino group and the like.

"Aryl group" may include phenyl group, 2-chlorophenyl group, 3-fluorophenyl group, 4-bromo-3-methylphenyl group, 4-methoxyphenyl group, 2-thienyl group, 2-chloro-5-thienyl group, 3-methyl-2-furyl group, 4-methyl-5-thiazolyl group, 4-chloro-2-methyl-5-oxazolyl group, 1-methyl-2-imidazolyl group, 1-bromo-2-naphthyl group, 6-methyl-2-naphthyl group, 8-methoxy-1-naphthyl group, 3-methyl-2-benzo[b]furyl group, 5-chloro-3-benzo[b]thienyl group and the like.

"5- or 6-membered cyclic ring formed together with the nitrogen atom" may include, for example, pyrrolyl group, 2-pyrrolinyl group, 3-pyrrolinyl group, pyrrolidinyl group, imidazolidinyl group, pyrazolidinyl group, succinimide group, piperidino group, piperazinyl group, morpholino group, glutarimide group and the like.

"Alkylideneamino group" may include ethylideneamino group, propylideneamino group, isopentylideneamino group, 2-methylpentylideneamino group, 3,3-dimethylbutylideneamino group, 2-ethylbutylideneamino group and the like.

"Arylalkylideneamino group" may include benzylideneamino group, 4-bromobenzylideneamino group, 2-chloro-6-fluorobenzylideneamino group, 2-methylbenzylideneamino group, 4-methylbenzylideneamino group, 2,5-dimethylbenzylideneamino group, 2,4,6-trimethylbenzylideneamino group, 3-methoxybenzylideneamino group, 3,4-dimethoxybenzylideneamino group, 2-phenethylideneamino group, (1-bromo-2-naphthyl)methylideneamino group, cinnamylideneamino group and the like.

"Acyloxy group", "carbamoyloxy group" or "aryloxy group" respectively means the above-mentioned "acyl group", "carbamoyl group" or "aryl group", to which an oxygen atom is bonded.

The novel compounds of the present invention represented by the formula (I) may be classified into the following two-types according to the partial structure of the compounds. Thus, when ring B is benzene ring, the compounds of the invention can be represented by the formula (I-1), and when ring B is thiophene, furan or pyrrole ring, the compounds of the invention can be represented by the formula (I-2).

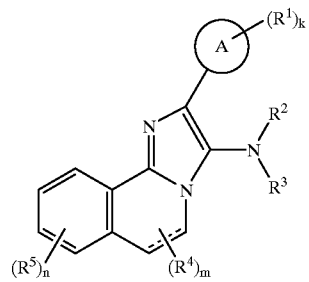
(I-1)

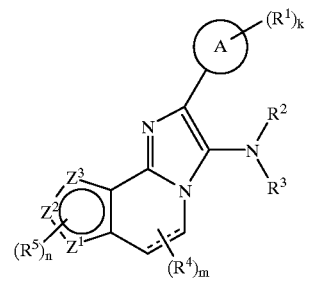
(I-2)

wherein ring A, $R^1$, $R^2$, $R^3$, $R^4$, $R^5$, k, m and n are as defined above, any one of $Z^1$, $Z^2$, or $Z^3$ represents a hetero-atom selected from sulfur, oxygen or nitrogen atom, and the others represent carbon atom.

Preferred compounds of the invention represented by the formula (I) may include the compounds (I-1) wherein ring B is benzene ring, or the compounds (I-2) wherein ring B is thiophene, furan, or pyrrole ring, and either $Z^1$ or $Z^3$ represents a hetero atom selected from sulfur, oxygen or nitrogen atom, and the other represents carbon atom. In particular, ring B preferably represents benzene or thiophene ring.

Preferred compounds of the invention represented by the formula (I) may include those wherein $R^1$ represents halogen atom, lower alkyl group which may be halogenated, or lower alkoxy group. In particular, $R^1$ preferably represents lower alkyl group having 1 or 2 carbon atoms.

Further preferred compounds of the invention represented by the formula (I) may include those wherein $R^2$ and $R^3$ may be the same or different and each represent hydrogen atom, alkenyl group or lower alkyl group which may have substituent(s) selected from the group consisting of halogen atom, lower alkoxy group, lower alkylthio group and aryl group, or $R^2$ and $R^3$, together with the nitrogen atom to which they are attached, may form a 5- or 6-membered monocyclic heterocyclic ring. Additional preferred compounds are those wherein at least one of $R^2$ and $R^3$ represents hydrogen atom.

Other preferred compounds of the invention represented by the formula (I) are those wherein ring A is benzene, thiophene, furan or pyrrole ring; ring B is benzene or thiophene ring; one of $R^1$ is halogen atom, lower alkyl group which may be halogenated, or lower alkoxy group; k is 1 or 2; $R^2$ and $R^3$ may be the same or different and each represent hydrogen atom, alkenyl group or lower alkyl group which may have substituent(s) selected from the group consisting of halogen atom, lower alkoxy group, lower alkylthio group and aryl group, or $R^2$ and $R^3$, together with the nitrogen atom to which they are attached, may form a 5- or 6-membered monocyclic heterocyclic ring.

Especially preferable compounds of the invention represented by the formula (I) are those wherein ring A is benzene, thiophene, furan or pyrrole ring; and at least one of the substituent(s) on ring A is located at ortho-position with respect to the binding site where ring A is bound to other part of the molecule including ring B moiety, as illustrated below:

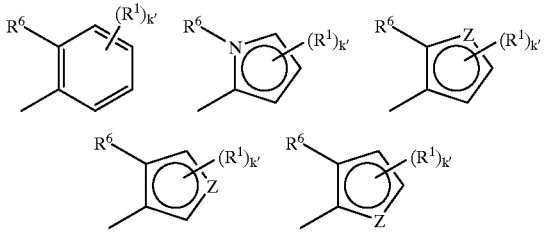

wherein $R^1$ and $R^6$ represent halogen atom, lower alkyl group which may be halogenated, or lower alkoxy group; k' represents 0 or 1; and Z represents a hetero-atom selected from sulfur, oxygen or nitrogen atom; ring B represents benzene or thiophene ring represented by the formula (I-2) in which either $Z^1$ or $Z^3$ represents sulfur atom; $R^2$ is hydrogen atom; $R^3$ is hydrogen atom, alkenyl group or lower alkyl group which may have substituent(s) selected from the group consisting of halogen atom, lower alkoxy group, lower alkylthio group and aryl group; and the dotted line, together with the solid line, represents a double bond.

Most preferable compounds of the invention represented by the formula (I) are those wherein ring A is benzene, thiophene, furan or pyrrole ring; the substituent $R^6$ on the ring A represented by the above-illustrated formulae is lower alkyl group having 1 or 2 carbon atoms; k' is 0 or 1; ring B represents benzene or thiophene ring represented by the formula (I-2) in which $Z^1$ is sulfur atom; $R^2$ and $R^3$ are each a hydrogen atom; $R^4$ and $R^5$ are each halogen atom, lower alkyl group, lower alkoxy group or lower alkylthio group; m is 0, 1 or 2; n is 0, 1 or 2; and the dotted line, together with the solid line, represents a double bond.

The following may be mentioned as examples of the compounds according to the invention to be singled out in particular:
3-amino-9-chloro-2-(2-methylphenyl)imidazo[2,1-a]isoquinoline,
3-amino-5-methyl-2-(2-methylphenyl)imidazo[2,1-a]isoquinoline,
3-amino-9-methyl-2-(2-methylphenyl)imidazo[2,1-a]isoquinoline,
3-amino-5-ethyl-2-(2-methylphenyl)imidazo[2,1-a]isoquinoline,
3-amino-5-isopropyl-2-(2-methylphenyl)imidazo[2,1-a]isoquinoline,
3-amino-5-methoxy-2-(2-methylphenyl)imidazo[2,1-a]isoquinoline,
3-amino-9-methoxy-2-(2-methylphenyl)imidazo[2,1-a]isoquinoline,
3-amino-2-(2-methylphenyl)-9-(methylthio)imidazo[2,1-a]isoquinoline,
3-amino-9-fluoro-5-methyl-2-(2-methylphenyl)imidazo[2,1-a]isoquinoline,
3-amino-2-(4-fluoro-2-methylphenyl)-5-methylimidazo[2,1-a]isoquinoline,
3-amino-2-(5-fluoro-2-methylphenyl)-9-methoxyimidazo[2,1-a]isoquinoline,
3-amino-2-(2-methyl-3-thienyl)imidazo[2,1-a]isoquinoline,
3-amino-5-methyl-2-(2-methyl-3-thienyl)imidazo[2,1-a]isoquinoline,
3-amino-2-(2-methyl-3-thienyl)-9-(methylthio)imidazo[2,1-a]isoquinoline,
3-amino-5-methoxy-2-(2-methyl-3-thienyl)imidazo[2,1-a]isoquinoline,
3-amino-9-fluoro-5-methyl-2-(2-methyl-3-thienyl)imidazo[2,1-a]isoquinoline,
3-amino-2-(2-ethyl-3-thienyl)imidazo[2,1-a]isoquinoline,
3-amino-2-(2,5-dimethyl-3-thienyl)-9-fluoroimidazo[2,1-a]isoquinoline,
3-amino-2-(2,5-dimethyl-3-thienyl)-5-methylimidazo[2,1-a]isoquinoline,
3-amino-2-(2,5-dimethyl-3-thienyl)-9-methoxyimidazo[2,1-a]isoquinoline,
3-amino-2-(5-chloro-2-methyl-3-thienyl)-5-methylimidazo[2,1-a]isoquinoline,
3-amino-2-(5-ethyl-2-methyl-3-thienyl)-5-methyimidazo[2,1-a]isoquinoline,
3-amino-2-(2-chloro-3-methyl-4-thienyl)-5-methylimidazo[2,1-a]isoquinoline,
3-amino-2-(2-methyl-3-furyl)-5-methylimidazo[2,1-a]isoquinoline,
3-amino-2-(2,5-dimethyl-3-furyl)-5-methylimidazo[2,1-a]isoquinoline,
3-amino-5-methyl-2-(2-methylphenyl)imidazo[1,2-a]thieno[3,2-c]pyridine,
3-amino-5-ethyl-2-(2-methylphenyl)imidazo[1,2-a]thieno[3,2-c]pyridine,
3-amino-5,8-dimethyl-2-(2-methylphenyl)imidazo[1,2-a]thieno[3,2-c]pyridine,
3-amino-2-(4-fluoro-2-methylphenyl)-5-methylimidazo[1,2-a]thieno[3,2-c]pyridine,
3-amino-5-methyl-2-(2-methyl-3-thienyl)imidazo[1,2-a]thieno[3,2-c]pyridine,
3-amino-8-methyl-2-(2-methyl-3-thienyl)imidazo[1,2-a]thieno[3,2-c]pyridine,
3-amino-5,6-dimethyl-2-(2-methyl-3-thienyl)imidazo[1,2-a]thieno[3,2-c]pyridine,
3-amino-2-(4-methyl-3-thienyl)imidazo[1,2-a]thieno[3,2-c]pyridine,
3-amino-2-(2-ethyl-3-thienyl)-5-methylimidazo[1,2-a]thieno[3,2-c]pyridine,
3-amino-2-(2-methoxy-3-thienyl)-5-methylimidazo[1,2-a]thieno[3,2-c]pyridine,
3-amino-2-(5-chloro-2-methyl-3-thienyl)-5-methylimidazo[1,2-a]thieno[3,2-c]pyridine,
3-amino-2-(2,5-dimethyl-3-thienyl)-5-methylimidazo[1,2-a]thieno[3,2-c]pyridine,
3-amino-2-(2,5-dimethyl-3-thienyl)-5-ethylimidazo[1,2-a]thieno[3,2-c]pyridine,
3-amino-2-(5-ethyl-2-methyl-3-thienyl)imidazo[1,2-a]thieno[3,2-c]pyridine,
3-amino-2-(5-methoxy-2-methyl-3-thienyl)-5-methylimidazo[1,2-a]thieno[3,2-c]pyridine,
3-amino-2-(2-chloro-3-methyl-4-thienyl)-5-methylimidazo[1,2-a]thieno[3,2-c]pyridine,
3-amino-5-methyl-2-(2-methyl-3-furyl)imidazo[1,2-a]thieno[3,2-c]pyridine,
3-amino-2-(2-methoxy-3-furyl)imidazo[1,2-a]thieno[3,2-c]pyridine,
3-amino-5-methyl-2-(1-methyl-2-pyrrolyl)imidazo[1,2-a]thieno[3,2-c]pyridine,
3-amino-2-(2,5-dimethyl-3-thienyl)furo[3,2-c]imidazo[1,2-a]pyridine,
3-amino-7-(4-chlorobenzyl)-2-(2-methylphenyl)imidazo[1,2-a]pyrrolo[3,2-c]pyridine,
3-amino-5-methyl-2-(2-methyl-3-thienyl)imidazo[1,2-a]thieno[3,4-c]pyridine,
3-amino-2-(2-chlorophenyl)imidazo[1,2-a]thieno[2,3-c]pyridine, 3-amino-5-methyl-2-(2-methylphenyl)imidazo[1,2-a]thieno[2,3-c]pyridine, 3-amino-5-methyl-2-(2-methyl-3-thienyl)imidazo[1,2-a]thieno[2,3-c]pyridine, 3-amino-2-(2,5-dimethyl-3-thienyl)imidazo[1,2-a]thieno[2,3-c]pyridine, 3-amino-2-(2,5-dimethyl-3-furyl)-5-methylimidazo[1,2-a]thieno[2,3-c]pyridine, 3-amino-2-(1-methyl-2-pyrrolyl)imidazo[1,2-a]thieno[2,3-c]pyridine, Suitable pharmaceutically acceptable salts of the compound (I) may include conventional salts used for drugs, such as those formed with an alkali metal (e.g. sodium, potassium, etc.) or an alkaline earth metal (e.g. magnesium, calcium, etc.) or an inorganic base(e.g. aluminum, etc.), and those formed with an organic base (e.g. ethylamine, propylamine, diethylamine, triethylamine, morpholine, pyridine, piperidine, N-ethylpiperidine, diethanolamine, cyclohexylamine, etc.), those formed with a basic amino acid (e.g. lysine, ornithine etc.), an ammonium salt, those formed with a mineral acid (e.g. hydrochloric acid, sulfuric acid, phosphoric acid, hydrobromic acid, etc.), those formed with an organic acid (e.g. acetic acid, oxalic acid, succinic acid, citric acid, maleic acid, malic acid, fumaric acid, tararic acid, picric acid, methanesulfonic acid, ethanesulfonic acid, etc.), and those formed with an acidic amino acid (e.g. glutamic acid, aspartic acid, etc.).

The compounds (I) of the present invention and pharmaceutically acceptable salts thereof may include their solvates (e.g. water, ethanol, etc.) and polymorphism, in case that they can be isolated.

The compounds (I) of the invention include stereoisomers, optical isomers or geometrical isomers thereof.

The compounds of the invention may be prepared by various methods. Typical methods are shown below.

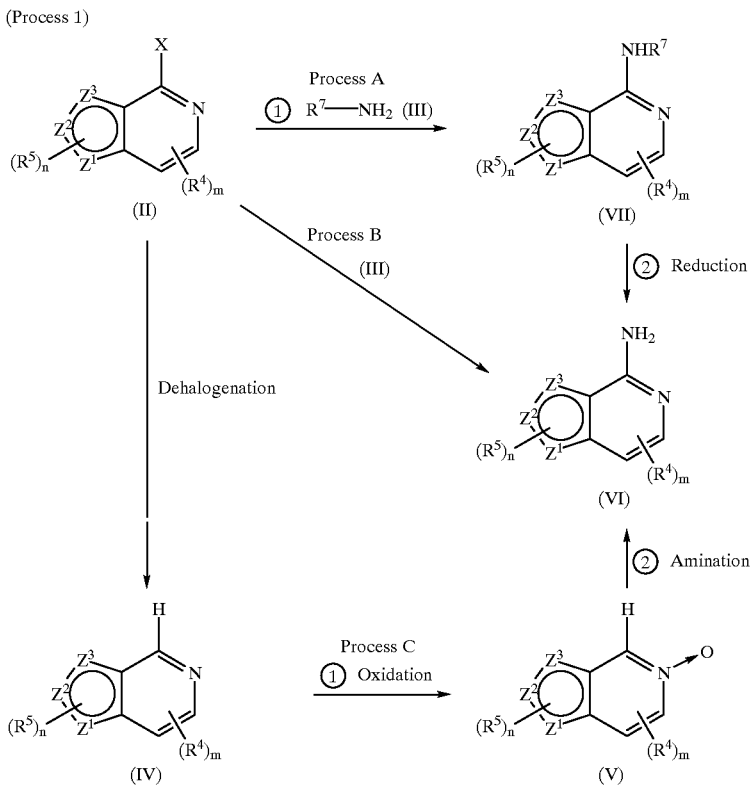

(Process 1)

wherein $R^4$, $R^5$, $Z^1$, $Z^2$, $Z^3$, m and n are as defined above; X is a leaving group to be replaced by amine, $R^7$ is hydrogen atom, amino group, arylalkyl group which may have substituent(s), or alkyl group which may have substituent(s).

Among the compounds represented by the formula (II), thienopyridines, in which any one of $Z^1$, $Z^2$ or $Z^3$ is a sulfur atom, can be prepared according to methods known to those skilled in the art [see, for example, Journal of Chemical Society, Perkin Transactions 1, p1390, (1975)], or analogous methods thereto. Furopyridines, any one of $Z^1$, $Z^2$ or $Z^3$ is an oxygen atom in the formula (II), can also be prepared according to methods known to those skilled in the art [see, for example, Journal of Heterocyclic Chemistry, 19, p1207, (1982)], or analogous methods thereto. Pyrrolopyridines, any one of $Z^1$, $Z^2$ or $Z^3$ is a nitrogen atom in the formula (II), can be prepared according to methods known to those skilled in the art [see, for example, Tetrahedron, 32, p773, (1976)], or analogous methods thereto. The leaving group X to be replaced by amine, may include, for example, alkoxy group, alkylthio group, alkylsulfinyl group, alkylsulfonyl group and halogen atom. Suitable leaving group X is halogen atom, in particular, chlorine atom.

Among the compounds represented by the formula (IV), thienopyridines, in which any one of $Z^1$, $Z^2$ or $Z^3$ is a sulfur atom, can be prepared according to methods known to those skilled in the art [see, for example, Journal of Heterocyclic Chemistry, 9, p843, (1972), Journal of Heterocyclic Chemistry, 30, p289, (1993)], or analogous methods thereto.

Furopyridines, any one of $Z^1$, $Z^2$ or $Z^3$ is an oxygen atom in the formula (IV), can be prepared according to methods known to those skilled in the art [see, for example, U.S. Pat. No. 4,808,595, Journal of Heterocyclic Chemistry, 8, p57, (1971), Tetrahedron Letters, p1741, (1977)], or analogous methods thereto. Pyrrolopyridines, any one of $Z^1$, $Z^2$ or $Z^3$ is a nitrogen atom in the formula (IV), can be prepared according to methods known to those skilled in the art [see, for example, Journal of Heterocyclic Chemistry, 29, p359, (1992)], or analogous methods thereto.

Among the compounds represented by the formula (VI), pyrrolo[3,2-c]pyridines, in which $Z^1$ is a nitrogen atom, can be prepared according to methods known to those skilled in the art [see, for example, Journal of Chemical Research. Synopses, 1, p4, (1986) or literatures mentioned therein], or analogous methods thereto.

Compound (VI) shown in Process 1 can be prepared according to Process A wherein compound (II) is condensed with compound (III) with heating (first step) and the resultant compound (VII) is reduced (second step), or Process B wherein compound (II) is condensed with compound (III) in which $R^7$ is a hydrogen atom with heating, or Process C wherein compound (IV) is subjected to oxidation (first step) and then the resultant compound (V) is subjected to amination (second step).

Process A (1) First step:

Of the compounds represented by the formula (III), suitable $R^7$ may include amino group, methyl group substituted by phenyl which has 1–3 straight or branched alkyl or alkoxy groups having 1 to 4 carbon atom(s), or benzyl group.

The reaction of compound (II) with compound (III) is conveniently carried out in an organic solvent, if neccessary, such as alcohols [e.g. 2-methoxyethanol, etc.], ethers [e.g. tetrahydrofuran, diethyl ether, etc.], aromatic hydrocarbons [e.g. benzene, toluene, xylene, etc.], organic amides [e.g. N,N-dimethylformamide, etc.] or other solvents which do not adversely affect the reaction. Preferably, this reaction is carried out without a solvent and at high temperature.

(2) Second step

The reduction in this step may include hydrogenolysis in the presence of catalyst [e.g. acids such as hydrochloric acid, sulfuric acid, Lewis acid and the like, Raney nickel, palladium-carbon, platinum oxide, etc.].

The reaction is carried out in a solvent such as organic nitrites [e.g. acetonitrile, etc.], acids [e.g. acetic acid, trifluoroacetic acid, etc.], alcohols [e.g. methanol, ethanol, etc.], ethers [e.g. tetrahydrofuran, diethyl ether, etc.], aromatic hydrocarbons [e.g. benzene, toluene, xylene, etc.], organic amides [e.g. N,N-dimethylformamide, etc.], any other solvents which do not adversely affect the reaction, or a mixture thereof.

The reaction temperature is not critical and the reaction is usually carried out with cooling or heating.

The reaction is completed in 5 minutes to 24 hours.

Process B

The reaction is usually carried out in ammonium hydroxide or a solution of ammonia in alcohol [e.g. methanol, ethanol, etc.] in a sealed reaction tube.

The reaction temperature is not critical, and the reaction is carried out with heating at 50 to 200° C.

The reaction is completed in 2 to 72 hours.

Process C (1) First step:

The oxidation in this step may include oxidation by peroxide [e.g. inorganic peroxides such as hydrogen peroxide and the like, organic peroxides such as 3-chloroperbenzoic acid, alkyl hydroperoxide, peracetic acid and the like].

The reaction is carried out in a solvent such as organic amides [e.g. N,N-dimethylformamide, etc.], alcohols [e.g. methanol, ethanol, etc.], ethers [e.g. tetrahydrofuran, diethyl ether, dioxane, etc.], hydrocarbons [e.g. benzene, toluene, xylene, hexane, etc.], organic nitrites [e.g. acetonitrile, etc.], acids [e.g. hydrochloric acid, sulfuric acid, acetic acid, etc.], water, any other solvents which do not adversely affect the reaction, or a mixture thereof.

The reaction temperature is not critical, and the reaction is usually carried out with cooling or heating.

The reaction is completed in 5 minutes to 24 hours.

(2) Second step:

The amination applied to this reaction may include the reaction with an aminating agent [e.g. ethanolamine, ammonia, etc.] in the presence of an acylating agent [e.g. p-toluenesulfonyl chloride, methanesulfonyl chloride, acetyl chloride, etc.].

The reaction is carried out in a solvent such as alcohols [e.g. methanol, ethanol, etc.], ethers [e.g. tetrahydrofuran, diethyl ether, dioxane, etc.], aromatic hydrocarbons [e.g. benzene, toluene, xylene, etc.], halogenated hydrocarbons [e.g. dichloromethane, chloroform, etc.], cyclic organic bases [e.g. pyridine, picoline, etc.], water, any other solvents which do not adversely affect the reaction, or a mixture thereof.

The reaction temperature is not critical, and the reaction is usually carried out with cooling or heating.

The reaction is completed in 30 minutes to 48 hours.

(Process 2)

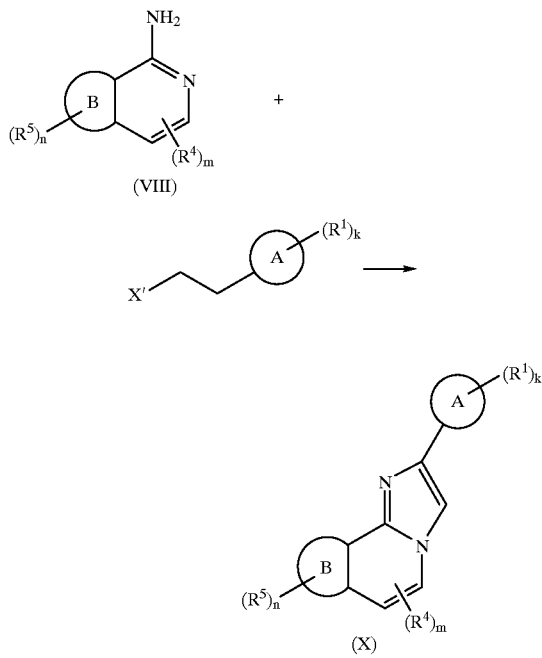

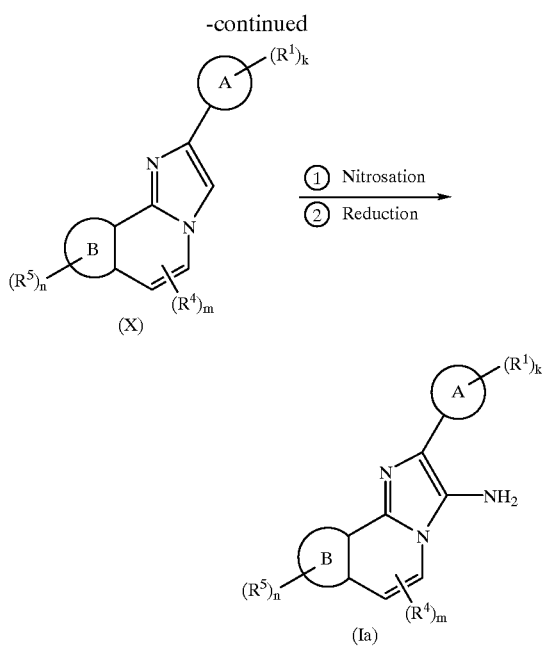

wherein ring A, ring B, $R^1$, $R^4$, $R^5$, k, m and n are as defined above; X' is a halogen atom.

Aminoisoquinolines, represented by the formula (VIII) in which ring B is benzene ring, can be prepared according to procedures known to those skilled in the art [e.g. Chemical and Pharmaceutical Bulletin, 5, p606, (1957); Heterocycles, 38, p375, (1994); European Patent Publication No. 143001], or analogous methods thereto. Among compounds of the formula (VIII), the compounds wherein ring B is thiophene, furan or pyrrole ring, may be represented by the formula (VI), and processes for preparing the same have been shown in aforementioned Process 1. 2-Halogenoethanones represented by the formula (IX) can be prepared according to procedures known to those skilled in the art [e.g. Japanese Patent Publication (Kokai) No. 152677/86; Journal of Medicinal Chemistry, 37, p57, (1994)], or analogous methods thereto.

Compound (X) or a salt thereof can be prepared by reacting Compound (VIII) or a salt thereof with Compound (IX).

The reaction is conveniently carried out in a solvent such as alcohols [e.g. methanol, ethanol, etc.], ethers [e.g. tetrahydrofuran, diethyl ether, etc.], aromatic hydrocarbons [e.g. benzene, toluene, xylene, etc.], halogenated hydrocarbons [e.g. dichloromethane, chloroform, etc.], organic amides [e.g. N,N-dimethylformamide, etc.] or any other solvents which do not adversely affect the reaction.

The reaction may be preferably carried out in the presence of an inorganic base or an organic base, such as an alkali metal hydroxide [e.g. sodium hydroxide, potassium hydroxide, etc.], an alkali metal carbonate [e.g. sodium carbonate, potassium carbonate, etc.], an alkali metal bicarbonate [e.g. sodium bicarbonate, potassium bicarbonate, etc.], trialkylamine [e.g. trimethylamine, triethylamine, etc.], pyridine or lutidine, or the like.

The reaction temperature is not critical, and the reaction is usually carried out at room temperature or with heating. The reaction is completed in 30 minutes to 24 hours.

The compounds represented by the formula (X) may also be prepared by change of partial structure of Compound (X) having suitable substituent(s) by means of a suitable means. For example, the aimed compound can be obtained in accordance with the following reactions: by replacing halogen such as chlorine, bromine, and the like with nitrile [see Shin jikken kagaku kouza; Maruzene company: Japan, 14, p1437], or by cross-coupling to convert halogen such as chlorine, bromine and the like into alkyl group such as methyl, ethyl and the like or aryl group such as phenyl, naphthyl, and the like [Synthesis, p317, (1985)], or hydrolysis of nitrile to carboxylic acid and its derivative [Organic Syntheses, 2, p588, (1943)], or conversion of nitrile into acyl group by using an organic metal reagent [Journal of Chemical Society, p4566, (1965)], or protection and deprotection of hydroxy or amino group [W.Greene, "Protective Groups in Organic Synthesis"], or reduction of nitro group into amino group, or reduction of carboxylic acid or its derivative into hydroxymethyl group, or alkylation of hydroxy or amino group, or conversion of amino group into alkylthio or arylthio group via diazonium salt [Journal of the American Chemical Society, 82, p2872, (1960)].

Compound (Ia) or a salt thereof can be prepared by subjecting compound (X) or a salt thereof to nitrosation (first step) and then subjecting the resultant compound to reduction (second step).

(1) First step:

Suitable nitrosating agents to be used in this reaction may include alkali metal nitrite salt [e.g. sodium nitrite, potassium nitrite, etc.], or nitrite ester [e.g. t-butyl nitrite, pentyl nitrite, isopentyl nitrite, etc.] and the like. The reaction is carried out in a solvent such as organic amides [e.g. N,N-dimethylformamide, etc.], alcohols [e.g. methanol, ethanol, etc.], ethers [e.g. tetrahydrofuran, diethyl ether, dioxane, etc.], hydrocarbons [e.g. benzene, toluene, xylene, hexane, etc.], organic nitrites [e.g. acetonitrile, etc.], acids [e.g. hydrochloric acid, sulfuric acid, acetic acid, etc.], water, any other solvents which do not adversely affect the reaction, or a mixture thereof.

The reaction temperature is not critical, and the reaction is usually carried out with cooling or heating.

The reaction is completed in 5 minutes to 6 hours.

(2) Second step:

The reduction applied to this reaction may include catalytic reduction in the presence of catalyst [e.g. palladium-carbon, platinum oxide, etc.] or reductions using a combination of a metal [e.g. titanium, iron, zinc, etc.] with an inorganic or organic acid such as hydrochloric acid, acetic acid, propionic acid and the like.

The reaction is carried out in a solvent such as organic amides [e.g. N,N-dimethylformamide, etc.], alcohols [e.g. methanol, ethanol, etc.], ethers [e.g. tetrahydrofuran, diethyl ether, dioxane, etc.], hydrocarbons [e.g. benzene, toluene, xylene, hexane, etc.], organic nitrites [e.g. acetonitrile, etc.], acids [e.g. hydrochloric acid, sulfuric acid, acetic acid, etc.], water, any other solvents which do not adversely affect the reaction, or a mixture thereof.

The reaction temperature is not critical, and the reaction is usually carried out with cooling or heating.

The reaction is completed in 5 minutes to 24 hours.

(Process 3)

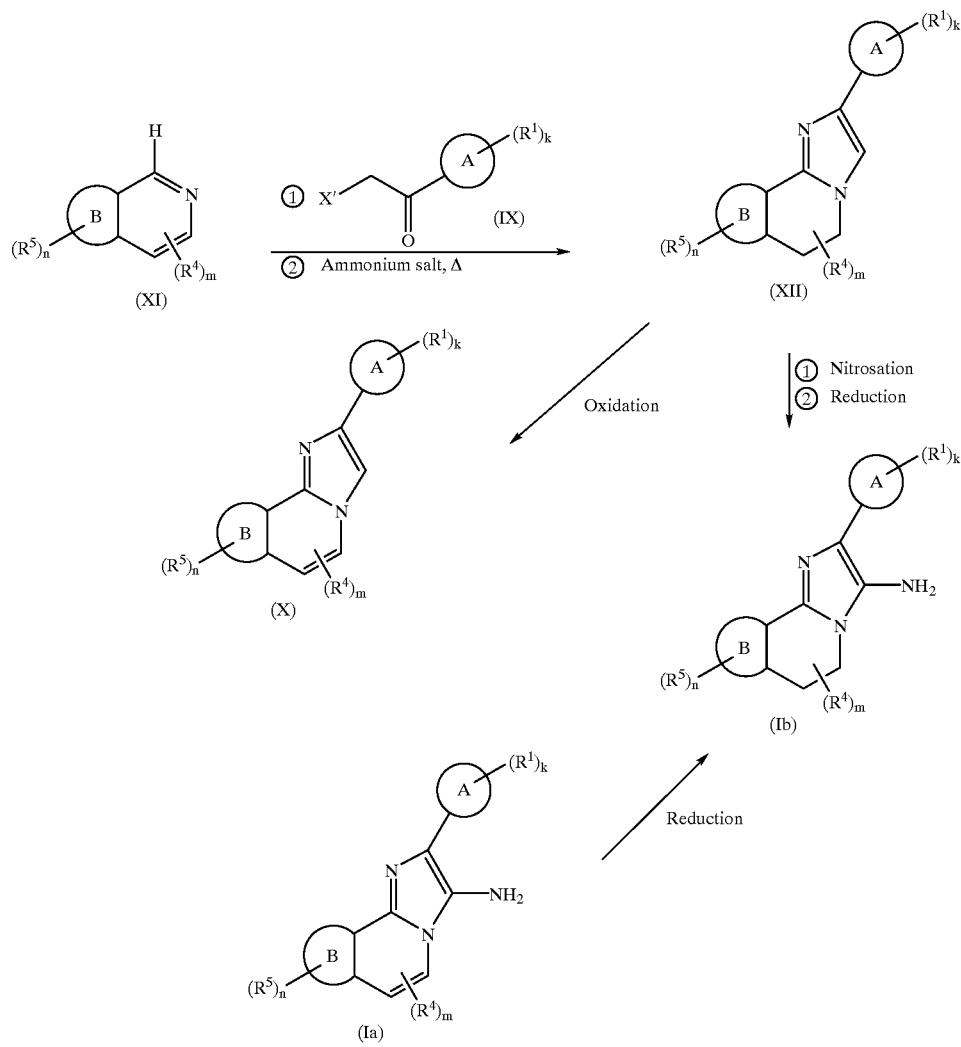

wherein ring A, ring B, $R^1$, $R^4$, $R^5$, k, m and n are as defined above; X' is a halogen atom. 3,4-Dihydroisoquinolines represented by the formula (XI) in which ring B is benzene ring, can be prepared according to procedures known to those skilled in the art [e.g. Japanese Patent Publication (Kokai) No. 213870/93 or literatures cited therein], or analogous methods thereto. Compounds represented by the formula (XI) wherein ring B is thiophene, furan or pyrrole ring, can be prepared according to procedures known to those skilled in the art [e.g. Journal of Medicinal Chemistry, 31, p641, (1988); Journal of Chemical Research Synopses, 1, p4, (1986), or literautures cited therein], or analogous methods thereto.

5,6-Dihydroimidazopyridines represented by the formula (XII) can be prepared by reacting compound (XI) with compound (IX) (first step) and then subjecting the resultant compound to react with an ammonium salt (second step).
(1) First step:

The reaction is carried out in a solvent such as ethers [e.g. tetrahydrofuran, diethyl ether, dioxane, etc.], hydrocarbons [e.g. benzene, toluene, xylene, hexane, etc.], halogenated hydrocarbons [e.g. dichloromethane, chloroform, etc.], organic amides [e.g. N,N-dimethylformamide, etc.] or any other solvents which do not adversely affect the reaction.

The reaction temperature is not critical, and the reaction is usually carried out at room temperature or with heating.

The reaction is completed in 30 minutes to 24 hours.
(2) Second step:

Suitable ammonium salts to be used in this reaction include inorganic ammonium salts [e.g. ammonium carbonate, ammonium sulfate, etc.] or organic ammonium salts [e.g. ammonium formate, ammonium acetate, etc.].

The reaction is carried out in a solvent such as organic amides [e.g. N,N-dimethylformamide, etc.], alcohols [e.g. methanol, ethanol, etc.], ethers [e.g. tetrahydrofuran, diethyl ether, dioxane, etc.], hydrocarbons [e.g. benzene, toluene, xylene, hexane, etc.], organic nitrites [e.g. acetonitrile, etc.], acids [e.g. hydrochloric acid, sulfuric acid, acetic acid, etc.], water or any other solvents which do not adversely affect the reaction.

The reaction temperature is not critical, and the reaction is usually carried out at room temperature or with heating.

The reaction is completed in 30 minutes to 24 hours.

The compounds represented by the formula (XII) can also be prepared by conversion of partial structure of the compounds (XII) having suitable substituent(s) by using the means exemplified above.

Compound (Ib) or a salt thereof in Process 3 can be prepared from compound (XII) in a similar manner to the method the compound (Ia) or a salt thereof from the compound (X) or a salt thereof aforementioned in Process 2.

The compound (X) or a salt thereof in Process 3 can also be prepared by subjecting compound (XII) or a salt thereof to oxidation.

The oxidation applied to this reaction may include dehydrogenation in the presence of catalyst [e.g. platinum, palladium-carbon, precipitated alumina-chromium oxide, copper, nickel, etc.].

The reaction solvent may include, for example, diphenylether, diphenylmethane, benzene, toluene, dimethylformamide, etc.] or any other solvents which do not adversely affect the reaction.

The reaction temperature is not critical, and the reaction is preferably carried out at ambient temperature or at the boiling point of the solvent used.

The reaction is completed in 30 minutes to 72 hours.

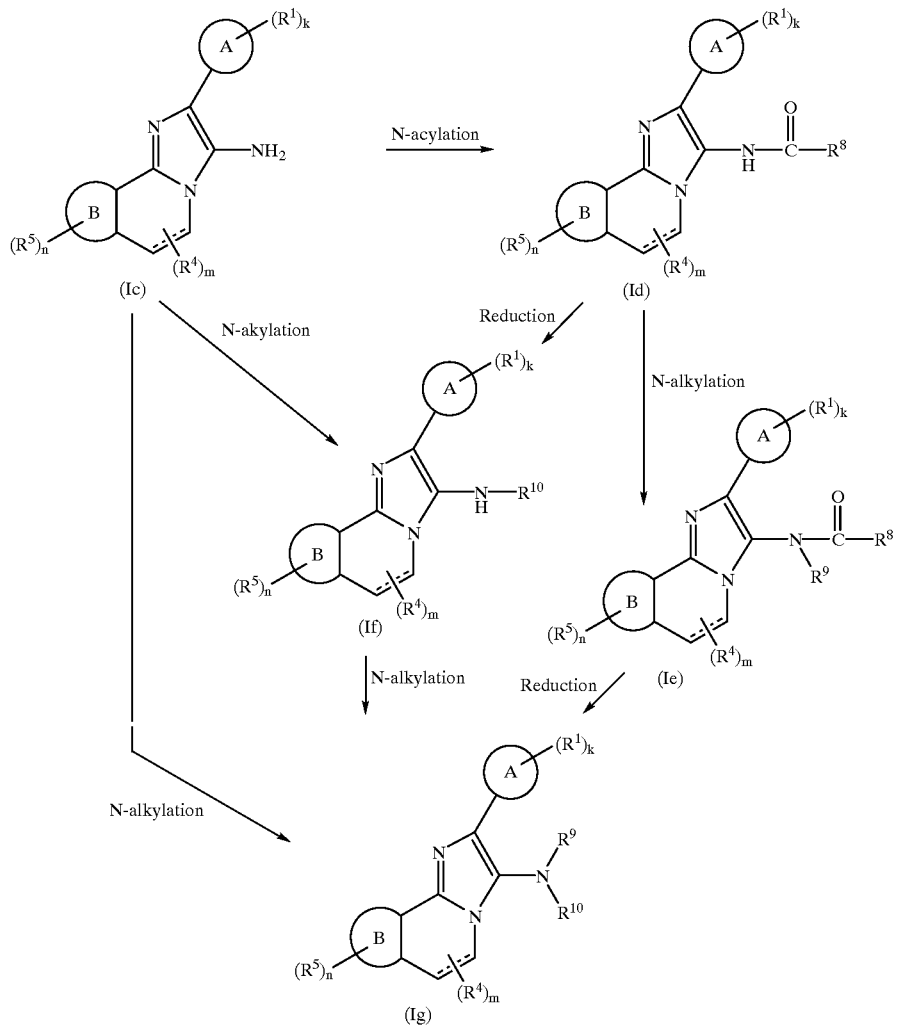

(Process 4)

naphthalene, tetralin, decalin, and the like. The reaction can also be carried out without solvent.

High reaction temperature is required although it is not critical, and the reaction is usually carried out with heating.

The reaction is completed in 30 minutes to 24 hours.

Compound (Ib) or a salt thereof can also be prepared by subjecting Compound (Ia) or a salt thereof to reduction.

The reduction applied to this reaction may include catalytic reduction in the presence of catalyst [e.g. palladium-carbon, platinum oxide, etc.].

The reaction is carried out in a solvent such as alcohols [e.g. methanol, ethanol, etc.], ethers [e.g. tetrahydrofuran, diethyl ether, dioxane, etc.], aromatic hydrocarbons [e.g. benzene, toluene, xylene, etc.], organic amides [e.g. N,N- wherein ring A, ring B, $R^1$, $R^4$, $R^5$, k, m and n are as defined above; $R^8$ is hydrogen atom, lower alkoxy group, alkenyl group, or lower alkyl group which may have substituent(s) selected from halogen atom, hydroxy group, lower alkoxy group, alkylthio group, alkylsulfinyl group, alkoxycarbonyl group, carbamoyl group, alkylamino group, or aryl group; $R^9$ and $R^{10}$ may be same or different and each represent hydrogen atom, lower alkoxy group, alkenyl group or lower alkyl group which may have substituent(s) selected from halogen atom, alkoxycarbonyl group, carbamoyl group, alkylamino group or aryl group.

Compound (Id) or a salt thereof can be prepared by subjecting compound (Ic) or a salt thereof to acylation.

The acylating agent to be used in this reaction may include desired carboxylic acids, carboxylic anhydrides, halogenated acyls or a combination of any one of those compounds with a suitable condensing agent.

The reaction is carried out in a solvent such as cyclic organic bases [e.g. pyridine, etc.], alcohols [e.g. methanol, ethanol, etc.], ethers [e.g. tetrahydrofuran, diethyl ether, dioxane, etc.], hydrocarbons [e.g. benzene, toluene, xylene, hexane, etc.], halogenated hydrocarbons [e.g. dichloromethane, chloroform, etc.], organic amides [e.g. N,N-dimethylformamide, etc.] or any other solvents which do not adversely affect the reaction.

The reaction temperature is not critical, and the reaction is usually carried out with cooling or heating.

The reaction is completed in 5 minutes to 6 hours.

Compounds (If), (Ig) and (Ie) or salts thereof can be prepared by subjecting the compounds (Ic), (If) and (Id) or salts thereof to alkylation.

The alkylating agent to be used in this reaction may include desired halogenated alkyls, halogenated arylalkyls or halogenated alkenyls and the like.

The reaction is usually carried out in the presence of a base.

Suitable bases may include inorganic bases such as alkali metal hydrides [e.g. sodium hydride, potassium hydride, etc.], alkali metal hydroxides [e.g. sodium hydroxide, potassium hydroxide, etc.], alkaline earth metal hydroxides [e.g. magnesium hydroxide, calcium hydroxide, etc.], alkali metal carbonates [e.g. sodium carbonate, potassium carbonate, etc.], alkaline earth metal carbonates [e.g. magnesium carbonate, calcium carbonate, etc.], alkali metal bicarbonates [e.g. sodium bicarbonate, potassium bicarbonate, etc.], alkaline earth metal phosphates [e.g. magnesium phosphate, calcium phosphate, etc.], alkali metal acetates [e.g. sodium acetate, potassium acetate, etc.], or the like, and organic bases such as trialkylamines [e.g. trimethylamine, triethylamine, etc.], pyridine, picoline, N-methylmorpholine, N-methylpyrrolidine, or the like.

The reaction is carried out in a solvent such as alcohols [e.g. methanol, ethanol, etc.], ethers [e.g. tetrahydrofuran, diethyl ether, dioxane, etc.], hydrocarbons [e.g. benzene, toluene, xylene, hexane, etc.], organic amides [e.g. N,N-dimethylformamide, etc.] or any other solvents which do not adversely affect the reaction.

The reaction temperature is not critical, and the reaction is preferably carried out at ambient temperature or at the boiling point of the solvent used.

The reaction is completed in 5 minutes to 24 hours.

Compounds (If) and (Ig) or salts thereof can also be prepared by subjecting compounds (Id) and (Ie) or salts thereof to reduction.

Suitable reducing agent to be used in this reaction may include lithium aluminium hydride and the like.

This reaction is usually carried out in a solvent such as ethers [e.g. tetrahydrofuran, diethyl ether, dioxane, etc.], hydrocarbons [e.g. benzene, toluene, xylene, hexane, etc.] or any other solvents which do not adversely affect the reaction.

The reaction temperature is not critical, and the reaction is usually carried out with cooling or heating.

The reaction is completed in 5 minutes to 24 hours.

(Process 5)

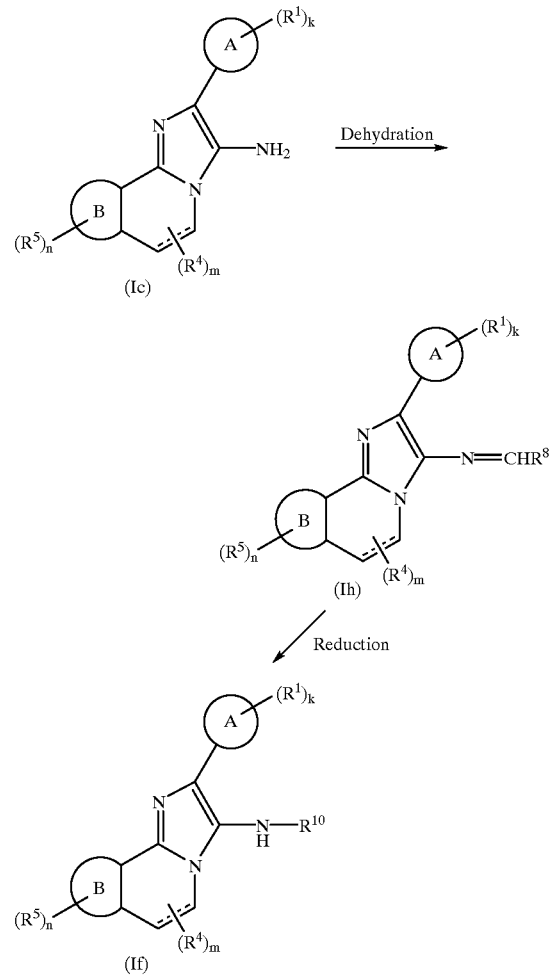

wherein ring A, ring B, $R^1$, $R^4$, $R^5$, $R^8$, $R^{10}$, k, m and n are as defined above.

Compound (Ih) or a salt thereof can be prepared by subjecting compound (Ic) or a salt thereof and a desired aldehyde to dehydration.

This reaction is usually carried out in a solvent such as alcohols [e.g. methanol, ethanol, etc.], ethers [e.g. tetrahydrofuran, diethyl ether, dioxane, etc.], aromatic hydrocarbons [e.g. benzene, toluene, xylene, etc.], halogenated hydrocarbons [e.g. dichloromethane, chloroform, etc.] or any other solvents which do not adversely affect the reaction, or without solvent.

As a catalyst, there may be used an inorganic base such as alkali metal hydroxide [e.g. sodium hydroxide, potassium hydroxide, etc.], an inorganic acid [e.g. hydrochloric acid, sulfuric acid, etc.] or Lewis acid [e.g. toluenesulfonic acid, zinc chloride, boron trifluoride, etc.].

The reaction temperature is not critical, and the reaction is usually carried out with cooling or heating.

The reaction is completed in 5 minutes to 24 hours.

Compound (If) or a salt thereof can also be prepared by subjecting compound (Ih) or a salt thereof to reduction.

Reductions applied to this reaction may include a reduction using metal hydride complex [e.g. sodium borohydride, etc.] and catalytic reduction in the presence of catalyst [e.g. palladium-carbon, platinum oxide, etc.].

This reaction is carried out in a solvent such as alcohols [e.g. methanol, ethanol, etc.], ethers [e.g. tetrahydrofuran, diethyl ether, dioxane, etc.], aromatic hydrocarbons [e.g. benzene, toluene, xylene, etc.], organic amides [e.g. N,N-dimethylformamide, etc.] or any other solvents which do not adversely affect the reaction.

The reaction temperature is not critical, and the reaction is preferably carried out at ambient temperature or at the boiling point of the solvent used.

The reaction is completed in 5 minutes to 24 hours.

Suitable salts of compounds (Ia)–(Ih), (X) and (XII) are acid addition salts as exemplified in compounds (I).

The compounds represented by the formula (I) can also be prepared by conversion of partial structure of compounds (I) having suitable substituent(s) using means as partly exemplified above.

The intermediates and aimed compounds obtained in the above processes can be isolated and purified using purification processes conveniently used in synthetic organic chemistry, for example, filtration, extraction, washing, concentration, drying, recrystallization, various chromatographies and the like. Intermediates can also be used in subsequent reactions without further purification.

When salts of compounds (I) are desirous to obtain and compound (I) is produced in the form of a salt, it may be suitably purified. When compound (I) is produced in the form of a free base, a salt can be obtained by the addition of an acid to a solution or suspension of compound (I) in a suitable organic solvent. Compounds (I) and pharmaceutically acceptable salts thereof can also exist as adducts with water or the solvent used. These adducts are included in this invention.

The compounds of the invention represented by the general formula (I) are shown in Table 1 and Table 2. The compound numbers will be referred to in the description hereinafter. The compounds represented by the formula (I-1) are shown in Table 1 and the compounds represented by the formula (I-2) are shown in Table 2. For reader's convenience, chemical formulae (I-1) and (I-2) in which position numbers are indicated are provided below.

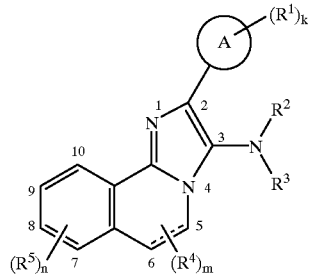

(I-1)

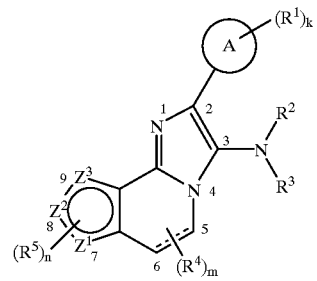

(I-2)

In Table 1 and Table 2, substituents are sometimes indicated using abbreviations, which are as follows:

| Me | methyl group | Pip | piperidino group |
|---|---|---|---|
| Et | ethyl group | Mor | morpholino group |
| Pr | n-propyl group | Suc | succinimide group |
| i-Pr | isopropyl group | Ph | phenyl group |
| Bu | n-butyl group | Pyr | pyrrolyl group |
| Pen | n-pentyl group | Fu | furyl group |
| i-Pen | isopentyl group | Th | thienyl group |
| c-Pen | cyclopentyl group | Naph | naphthyl group |
| Hex | n-hexyl group | Bzfu | benzo[b]furyl group |
| Ac | acetyl group | | |

In Table 1 and Table 2, the number in parentheses means the position where ring A binds to the 2-position, and the number and substitution in brackets means where the substituent(s) $R^1$ locates on ring A. In addition, the number in parentheses indicates the position on the aryl group at which it binds to other group, and the number and substitution in brackets indicates the position and nature of the substitution on the aryl group. Several examples are given below.

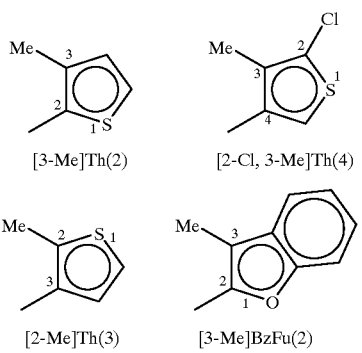

[3-Me]Th(2)    [2-Cl, 3-Me]Th(4)

[2-Me]Th(3)    [3-Me]BzFu(2)

In column "5–6" of Table 1 and Table 2, "DB" means that the dotted line, together with the solid line, represents a double bond between the 5- and 6-positions in the the formula (I-1) or (I-2), while "SB" means that the bond represents a single bond.

TABLE 1

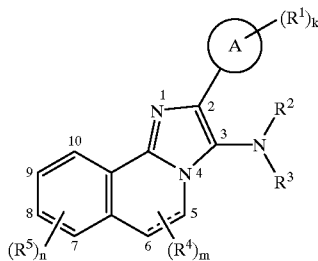

(I-1)

Examples of the compounds according to the invention represented by the formula (I-1).

| Compound No | A–(R¹)ₖ | NR²R³ | R⁴, R⁵ | 5–6 |
|---|---|---|---|---|
| 1 | [2-F]Ph | NH₂ | — | DB |
| 2 | [2-Cl]Ph | NH₂ | — | DB |
| 3 | [2-Me]Ph | NH₂ | — | DB |
| 4 | [2-Me]Ph | NH₂ | 9-F | DB |
| 5 | [2-Me]Ph | NH₂ | 7-Cl | DB |
| 6 | [2-Me]Ph | NH₂ | 9-Cl | DB |
| 7 | [2-Me]Ph | NH₂ | 10-Cl | DB |
| 8 | [2-Me]Ph | NH₂ | 7-Br | DB |
| 9 | [2-Me]Ph | NH₂ | 5-Me | DB |
| 10 | [2-Me]Ph | NH₂ | 9-Me | DB |
| 11 | [2-Me]Ph | NH₂ | 5-Et | DB |
| 12 | [2-Me]Ph | NH₂ | 5-Pr | DB |
| 13 | [2-Me]Ph | NH₂ | 7-Pr | DB |
| 14 | [2-Me]Ph | NH₂ | 5-i-Pr | DB |
| 15 | [2-Me]Ph | NH₂ | 6-i-Pen | DB |
| 16 | [2-Me]Ph | NH₂ | 6-CH₂OMe | DB |
| 17 | [2-Me]Ph | NH₂ | 6-CH₂OPh | DB |
| 18 | [2-Me]Ph | NH₂ | 7-CH₂OH | DB |
| 19 | [2-Me]Ph | NH₂ | 9-CH(OH)Me | DB |
| 20 | [2-Me]Ph | NH₂ | 9-Ph | DB |
| 21 | [2-Me]Ph | NH₂ | 6-[4-OMe]Ph | DB |
| 22 | [2-Me]Ph | NH₂ | 9-O | DB |
| 23 | [2-Me]Ph | NH₂ | 5-OMe | DB |
| 24 | [2-Me]Ph | NH₂ | 6-OMe | DB |
| 25 | [2-Me]Ph | NH₂ | 7-OMe | DB |
| 26 | [2-Me]Ph | NH₂ | 9-OMe | DB |
| 27 | [2-Me]Ph | NH₂ | 6-OEt | DB |
| 28 | [2-Me]Ph | NH₂ | 9-OEt | DB |
| 29 | [2-Me]Ph | NH₂ | 9-OPr | DB |
| 30 | [2-Me]Ph | NH₂ | 9-O-i-Pr | DB |
| 31 | [2-Me]Ph | NH₂ | 9-OBu | DB |
| 32 | [2-Me]Ph | NH₂ | 7,9-(OMe)₂ | DB |
| 33 | [2-Me]Ph | NH₂ | 8,9-(OMe)₂ | DB |
| 34 | [2-Me]Ph | NH₂ | 9,10-(OMe)₂ | DB |
| 35 | [2-Me]Ph | NH₂ | 9-OCH₂CO₂Et | DB |
| 36 | [2-Me]Ph | NH₂ | 9-OCH₂CH₂OH | DB |
| 37 | [2-Me]Ph | NH₂ | 9-OCH₂CH₂OMe | DB |
| 38 | [2-Me]Ph | NH₂ | 6-OCH₂Ph | DB |
| 39 | [2-Me]Ph | NH₂ | 7-OCH₂Ph | DB |
| 40 | [2-Me]Ph | NH₂ | 9-OCH₂Ph | DB |
| 41 | [2-Me]Ph | NH₂ | 9-OAc | DB |
| 42 | [2-Me]Ph | NH₂ | 9-OCOPr | DB |
| 43 | [2-Me]Ph | NH₂ | 9-OCO-i-Pr | DB |
| 44 | [2-Me]Ph | NH₂ | 9-OCONMe₂ | DB |
| 45 | [2-Me]Ph | NH₂ | 7-SCH₂Ph | DB |
| 46 | [2-Me]Ph | NH₂ | 7-SMe | DB |
| 47 | [2-Me]Ph | NH₂ | 6-Ac | DB |
| 48 | [2-Me]Ph | NH₂ | 7-CO-[4-OMe]Ph | DB |
| 49 | [2-Me]Ph | NH₂ | 7-CO₂H | DB |
| 50 | [2-Me]Ph | NH₂ | 6-CO₂Me | DB |
| 51 | [2-Me]Ph | NH₂ | 7-CO₂Me | DB |
| 52 | [2-Me]Ph | NH₂ | 7-CN | DB |
| 53 | [2-Me]Ph | NH₂ | 9-CN | DB |
| 54 | [2-Me]Ph | NH₂ | 7-N(Et)₂ | DB |

TABLE 1-continued

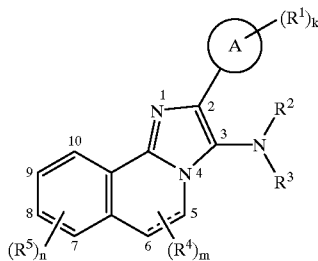

(I-1)

Examples of the compounds according to the invention represented by the formula (I-1).

| Compound No | A-(R¹)ₖ | NR²R³ | R⁴, R⁵ | 5–6 |
|---|---|---|---|---|
| 55 | [2-Me]Ph | NH₂ | 9-OMe, 10-Cl | DB |
| 56 | [2-Me]Ph | NH₂ | 5-Me, 9-OMe | DB |
| 57 | [3-Me]Ph | NH₂ | — | DB |
| 58 | [4-Me]Ph | NH₂ | — | DB |
| 59 | [2-Et]Ph | NH₂ | — | DB |
| 60 | [2-CF₃]Ph | NH₂ | — | DB |
| 61 | [2-OMe]Ph | NH₂ | — | DB |
| 62 | [2,4-Me₂]Ph | NH₂ | — | DB |
| 63 | [2-Me, 4-Et]Ph | NH₂ | — | DB |
| 64 | [2-Me, 4-F]Ph | NH₂ | 5-Me | DB |
| 65 | [2-Me, 5-F]Ph | NH₂ | 6-OMe | DB |
| 66 | [2-Me, 4-Cl]Ph | NH₂ | — | DB |
| 67 | [2-Me, 5-Cl]Ph | NH₂ | 10-Cl | DB |
| 68 | [2-Me, 4-OH]Ph | NH₂ | — | DB |
| 69 | [2-Me, 4-OMe]Ph | NH₂ | — | DB |
| 70 | [2-Me, 4-OAc]Ph | NH₂ | — | DB |
| 71 | [2,4,6-Me₃]Ph | NH₂ | — | DB |
| 72 | [2-Me, 4-OMe, 5-Br]Ph | NH₂ | — | DB |
| 73 | [3-Me]Th(2) | NH₂ | — | DB |
| 74 | [3-Me]Th(2) | NH₂ | 6-OMe | DB |
| 75 | [3-Me]Th(2) | NH₂ | 9-OMe | DB |
| 76 | [4-Me]Th(2) | NH₂ | — | DB |
| 77 | [3-Et]Th(2) | NH₂ | — | DB |
| 78 | [2-Me]Th(3) | NH₂ | — | DB |
| 79 | [2-Me]Th(3) | NH₂ | 5-Me | DB |
| 80 | [2-Me]Th(3) | NH₂ | 5-OMe | DB |
| 81 | [4-Me]Th(3) | NH₂ | — | DB |
| 82 | [2-Et]Th(3) | NH₂ | — | DB |
| 83 | [2,5-Me₂]Th(3) | NH₂ | — | DB |
| 84 | [2,5-Cl₂, 4-Me]Th(3) | NH₂ | — | DB |
| 85 | [2-Cl, 3-Me]Th(4) | NH₂ | — | DB |
| 86 | [2-Cl, 3-Me]Th(4) | NH₂ | 7-Br | DB |
| 87 | [2-Cl, 3-Me]Th(4) | NH₂ | 5-Me | DB |
| 88 | [3-Me]Fu(2) | NH₂ | — | DB |
| 89 | [2-Me]Fu(3) | NH₂ | — | DB |
| 90 | [2-Me]Fu(3) | NH₂ | 5-Me | DB |
| 91 | [2,5-Me₂]Fu(3) | NH₂ | — | DB |
| 92 | [2,5-Me₂]Fu(3) | NH₂ | 5-OMe | DB |
| 93 | [2,5-Me₂]Fu(3) | NH₂ | 9-OMe | DB |
| 94 | [1-Me]Pyr(2) | NH₂ | — | DB |
| 95 | [1-Et]Pyr(2) | NH₂ | — | DB |
| 96 | [2-Me]Ph | NH₂ | — | SB |
| 97 | [2-Me]Ph | NH₂ | 9-F | SB |
| 98 | [2-Me]Ph | NH₂ | 8-Cl | SB |
| 99 | [2-Me]Ph | NH₂ | 9-Br | SB |
| 100 | [2-Me]Ph | NH₂ | 5-Me | SB |
| 101 | [2-Me]Ph | NH₂ | 7-Me | SB |
| 102 | [2-Me]Ph | NH₂ | 9-Me | SB |
| 103 | [2-Me]Ph | NH₂ | 9-OMe | SB |
| 104 | [2-Me]Ph | NH₂ | 5,5-Me₂ | SB |
| 105 | [2-Me]Ph | NH₂ | 6,7-Me₂ | SB |
| 106 | [2-Me]Ph | NH₂ | 5-Me, 9-OMe | SB |
| 107 | [2-Me, 4-OH]Ph | NH₂ | — | SB |
| 108 | [2-Me, 4-OH, 5-Br]Ph | NH₂ | — | SB |

TABLE 1-continued (I-1)

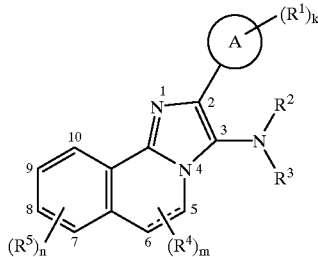

Examples of the compounds according to the invention represented by the formula (I-1).

| Compound No | A-(R$^1$)$_k$ | NR$^2$R$^3$ | R$^4$, R$^5$ | 5–6 |
|---|---|---|---|---|
| 109 | [2-Me]Th(3) | NH$_2$ | — | SB |
| 110 | [2,5-Me$_2$]Th(3) | NH$_2$ | — | SB |
| 111 | [2-F]Ph | NH(Ac) | — | DB |
| 112 | [2-Me]Ph | NH(Ac) | — | DB |
| 113 | [2-Me]Ph | NH(Ac) | 6-i-Pen | DB |
| 114 | [2-Me]Ph | NH(Ac) | 7-Pr | DB |
| 115 | [2-Me]Ph | NH(Ac) | 6-OMe | DB |
| 116 | [2-Me]Ph | NH(Ac) | 9-OMe | DB |
| 117 | [2-Me]Ph | NH(Ac) | 7,9-(OMe)$_2$ | DB |
| 118 | [3-Me]Ph | NH(Ac) | — | DB |
| 119 | [4-Me]Ph | NH(Ac) | — | DB |
| 120 | [2-Et]Ph | NH(Ac) | — | DB |
| 121 | [3-Me]Th(2) | NH(Ac) | — | DB |
| 122 | [3-Et]Th(2) | NH(Ac) | — | DB |
| 123 | [2-Cl, 3-Me]Th(4) | NH(Ac) | — | DB |
| 124 | [2-Me]Ph | NH(COCH$_2$CH$_2$Cl) | — | DB |
| 125 | [2-Me]Ph | NH(COCH$_2$CH$_2$SMe) | — | DB |
| 126 | [2-Me]Ph | NH(COCH$_2$CH$_2$COOH) | — | DB |
| 127 | [2,4-Me$_2$]Ph | NH(COCH$_2$CH$_2$COOH) | — | DB |
| 128 | [2-Me]Ph | NH(COPen) | — | DB |
| 129 | [2-Me]Ph | NH(COCH=CHCO$_2$Me) | — | DB |
| 130 | [2-Me]Ph | NH(CO-[3-CF$_3$]Ph) | — | DB |
| 131 | [2-Me]Ph | NH(CO-[4-OMe]Ph) | — | DB |
| 132 | [2-Me]Ph | NH(CO-Th(2)) | — | DB |
| 133 | [2-Me]Ph | NH(CO-[3-Me]Bzfu(2)) | — | DB |
| 134 | [2-Me]Ph | N(Ac)(CH$_2$CO$_2$Et) | — | DB |
| 135 | [3-Et]Th(2) | N(Ac)(CH$_2$CON(Et)$_2$) | — | DB |
| 136 | [2-Me]Ph | N(Ac)(CH$_2$CH$_2$OMe) | — | DB |
| 137 | [2-F]Ph | N(Ac)(Pr) | — | DB |
| 138 | [2-Me]Ph | N(Ac)(Pr) | — | DB |
| 139 | [2-Me]Ph | N(Ac)(Pr) | 6-i-Pen | DB |
| 140 | [2-Me]Ph | N(Ac)(Pr) | 6-OMe | DB |
| 141 | [2-Me]Ph | N(Ac)(Pr) | 9-OMe | DB |
| 142 | [2-Me]Ph | N(Ac)(Pr) | 8,9-(OMe)$_2$ | DB |
| 143 | [3-Me]Ph | N(Ac)(Pr) | — | DB |
| 144 | [3-Me]Th(2) | N(Ac)(Pr) | — | DB |
| 145 | [2-Me]Ph | N(Ac)(i-Pr) | — | DB |
| 146 | [2-Me]Ph | N(Ac)(CH$_2$CH=CH$_2$) | — | DB |
| 147 | [4-Me]Ph | N(Ac)(i-Pen) | — | DB |
| 148 | [2-Et]Ph | N(Ac)(i-Pen) | — | DB |
| 149 | [2,4-Me$_2$]Ph | N(Ac)(i-Pen) | — | DB |
| 150 | [2-Et]Ph | N(Ac)(CH$_2$-[4-Me]Ph) | — | DB |
| 151 | [2-Me]Ph | N(Ac)(CH$_2$-[4-Me]Ph) | — | DB |
| 152 | [2-Me]Ph | N(COCH$_2$CH$_2$SMe)(Et) | — | DB |
| 153 | [2-Me]Ph | Suc | — | DB |
| 154 | [2,4-Me$_2$]Ph | Suc | — | DB |
| 155 | [2-Me]Ph | NH(CH$_2$CO$_2$Et) | — | DB |
| 156 | [2-Me]Ph | NH(CH$_2$CO$_2$Pr) | — | DB |
| 157 | [2-Me]Ph | NH(CH$_2$CON(Et)$_2$) | — | DB |
| 158 | [2-Me]Ph | NH(Et) | — | DB |
| 159 | [2-Me]Ph | NH(Et) | 7-Cl | DB |
| 160 | [2-Me]Ph | NH(Et) | 9-Cl | DB |
| 161 | [2-Me]Ph | NH(Et) | 5-Me | DB |
| 162 | [2-Me]Ph | NH(Et) | 6-i-Pen | DB |

TABLE 1-continued

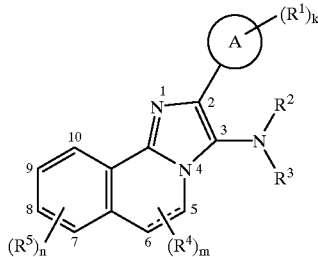

(I-1)

Examples of the compounds according to the invention represented by the formula (I-1).

| Compound No | A-(R$^1$)$_k$ | NR$^2$R$^3$ | R$^4$, R$^5$ | 5–6 |
|---|---|---|---|---|
| 163 | [2-Me]Ph | NH(Et) | 7-Pr | DB |
| 164 | [2-Me]Ph | NH(Et) | 6-CH$_2$OMe | DB |
| 165 | [2-Me]Ph | NH(Et) | 7-OH | DB |
| 166 | [2-Me]Ph | NH(Et) | 6-OMe | DB |
| 167 | [2-Me]Ph | NH(Et) | 9-OMe | DB |
| 168 | [2-Me]Ph | NH(Et) | 6-OCH$_2$Ph | DB |
| 169 | [2-Me]Ph | NH(Et) | 7-OCH$_2$Ph | DB |
| 170 | [2-Me]Ph | NH(Et) | 7-SMe | DB |
| 171 | [2-Me]Ph | NH(Et) | 7-OAc | DB |
| 172 | [2-Me]Ph | NH(Et) | 7-CO$_2$Me | DB |
| 173 | [2-Me]Ph | NH(Et) | 7-CO$_2$Et | DB |
| 174 | [2-Me]Ph | NH(Et) | 7-N(Et)$_2$ | DB |
| 175 | [2-CF$_3$]Ph | NH(Et) | — | DB |
| 176 | [3-Me]Th(2) | NH(Et) | 6-OMe | DB |
| 177 | [3-Me]Th(2) | NH(Et) | 9-OMe | DB |
| 178 | [3-Et]Th(2) | NH(Et) | — | DB |
| 179 | [2-Cl, 3-Me]Th(4) | NH(Et) | — | DB |
| 180 | [2-Me]Ph | NH(CH$_2$CH$_2$OMe) | — | DB |
| 181 | [2-Me]Ph | NH(Pr) | 6-i-Pen | DB |
| 182 | [2-Me]Ph | NH(Pr) | 6-OMe | DB |
| 183 | [2-Me]Ph | NH(Pr) | 9-Me | DB |
| 184 | [2-Me]Ph | NH(i-Pr) | — | DB |
| 185 | [2-Me]Ph | NH(CH$_2$CH$_2$CH$_2$SMe) | — | DB |
| 186 | [2-Me]Ph | NH(CH$_2$CH$_2$CH$_2$SOMe) | — | DB |
| 187 | [2-Me]Ph | NH(Pen) | — | DB |
| 188 | [2-Me]Ph | NH(i-Pen) | — | DB |
| 189 | [2,4-Me$_2$]Ph | NH(i-Pen) | — | DB |
| 190 | [2-Me]Ph | NH(c-Pen) | — | DB |
| 191 | [2-Me]Ph | NH(Hex) | — | DB |
| 192 | [2-Me]Ph | NH(CH(Me)(Ph)) | — | DB |
| 193 | [2-Me]Ph | NH(CH$_2$-[4-F]Ph) | — | DB |
| 194 | [2-Me]Ph | NH(CH$_2$-[4-Me]Ph) | — | DB |
| 195 | [2-Me]Ph | NH(CH$_2$-[1-Br]Naph(2)) | — | DB |
| 196 | [2-Me]Ph | NH(CH$_2$-[3-Me]Bzfu(2)) | — | DB |
| 197 | [2-Me]Ph | N(Me)$_2$ | 7-CO$_2$Me | DB |
| 198 | [2-Me]Ph | N(CH$_2$CON(Et)$_2$)$_2$ | — | DB |
| 199 | [2-Me]Ph | N(Et)$_2$ | 7-Cl | DB |
| 200 | [2-Me]Ph | N(Et)$_2$ | 7-Br | DB |
| 201 | [2-Cl, 3-Me]Th(4) | N(Et)$_2$ | — | DB |
| 202 | [2-Me]Ph | N(Et)(CH$_2$CH$_2$Cl) | — | DB |
| 203 | [3-Et]Th(2) | N(Et)(CH$_2$CH$_2$N(Et)$_2$) | — | DB |
| 204 | [2-Me]Ph | N(Et)(CH$_2$CH$_2$OH) | — | DB |
| 205 | [2-Me]Ph | N(Et)(CH$_2$CH$_2$OMe) | — | DB |
| 206 | [2-F]Ph | N(Et)(Pr) | — | DB |
| 207 | [2-Me]Ph | N(Et)(Pr) | — | DB |
| 208 | [2-Me]Ph | N(Et)(Pr) | 6-i-Pen | DB |
| 209 | [2-Me]Ph | N(Et)(Pr) | 9-OMe | DB |
| 210 | [2-Me]Ph | N(Et)(Pr) | 7,9-(OMe)$_2$ | DB |
| 211 | [3-Me]Ph | N(Et)(Pr) | — | DB |
| 212 | [3-Me]Th(2) | N(Et)(Pr) | — | DB |
| 213 | [2-Me]Ph | N(Et)(i-Pr) | — | DB |
| 214 | [2-Me]Ph | N(Et)(CH$_2$CH$_2$CH$_2$SMe) | — | DB |
| 215 | [2,5-Me$_2$]Th(3) | N(Et)(CH$_2$CH$_2$CH$_2$SMe) | 7-OCH$_2$Ph | DB |
| 216 | [2-Et]Ph | N(Et)(i-Pen) | — | DB |

TABLE 1-continued

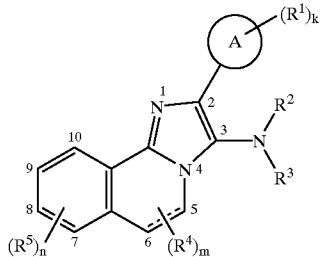

(I-1)

Examples of the compounds according to the invention represented by the formula (I-1).

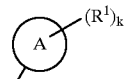

| Compound No | A-(R$^1$)$_k$ | NR$^2$R$^3$ | R$^4$, R$^5$ | 5–6 |
|---|---|---|---|---|
| 217 | [2-Me]Ph | Pip | — | DB |
| 218 | [2-Me]Ph | Mor | — | DB |
| 219 | [2-Me]Ph | N(Et)(CH$_2$-[4-Me]Ph) | — | DB |
| 220 | [2-Et]Ph | N(Et)(CH$_2$-[4-Me]Ph) | — | DB |
| 221 | [2-Me]Ph | NH(CH$_2$CH=CH$_2$) | — | DB |
| 222 | [2-Me]Ph | N(Et)(CH$_2$CH=CH$_2$) | — | DB |
| 223 | [2-Me]Ph | N(CH$_2$CH=CH$_2$)$_2$ | — | DB |
| 224 | [2-Me]Ph | N=CHCH$_2$CH$_3$ | — | DB |
| 225 | [2-Me]Ph | N=CH-[4-Me]Ph | — | DB |
| 226 | [2-Et]Ph | N=CH-[4-Me]Ph | — | DB |
| 227 | [2-Me]Fu(3) | N=CH-[4-Me]Ph | 7-SCH$_2$Ph | DB |
| 228 | [2-Me]Ph | N=CH-[1-Br]NaPh(2) | — | DB |

TABLE 2

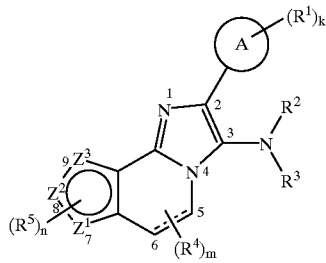

(I-2)

Examples of the compounds according to the invention represented by the formula (I-2).

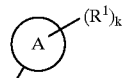

| Compound No | Z$^1$ | Z$^2$ | Z$^3$ | A-(R$^1$)$_k$ | NR$^2$R$^3$ | R$^4$, R$^5$ | 5–6 |
|---|---|---|---|---|---|---|---|
| 229 | S | C | C | Ph | NH$_2$ | — | DB |
| 230 | S | C | C | Ph | NH$_2$ | 5-Me | DB |
| 231 | S | C | C | [2-OH]Ph | NH$_2$ | 5-Me | DB |
| 232 | S | C | C | [2-Cl]Ph | NH$_2$ | — | DB |
| 233 | S | C | C | [4-Cl]Ph | NH$_2$ | 5-Me | DB |
| 234 | S | C | C | [2-Me]Ph | NH$_2$ | — | DB |
| 235 | S | C | C | [2-Me]Ph | NH$_2$ | 8-Br | DB |
| 236 | S | C | C | [2-Me]Ph | NH$_2$ | 5-Me | DB |
| 237 | S | C | C | [2-Me]Ph | NH$_2$ | 8-Me | DB |
| 238 | S | C | C | [2-Me]Ph | NH$_2$ | 5-Et | DB |
| 239 | S | C | C | [2-Me]Ph | NH$_2$ | 5,6-Me$_2$ | DB |
| 240 | S | C | C | [2-Me]Ph | NH$_2$ | 5,8-Me$_2$ | DB |
| 241 | S | C | C | [2-Me]Ph | NH$_2$ | 8-OMe | DB |

TABLE 2-continued (I-2)

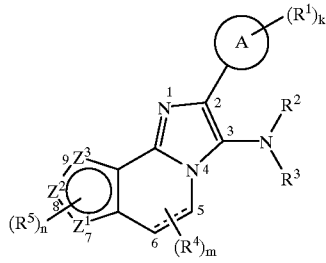

Examples of the compounds according to the invention represented by the formula (I-2).

| Compound No | $Z^1$ | $Z^2$ | $Z^3$ | A-(R$^1$)$_k$ | NR$^2$R$^3$ | R$^4$, R$^5$ | 5–6 |
|---|---|---|---|---|---|---|---|
| 242 | S | C | C | [3-Me]Ph | NH$_2$ | 5-Me | DB |
| 243 | S | C | C | [2-Et]Ph | NH$_2$ | 5-Me | DB |
| 244 | S | C | C | [2-CF$_3$]Ph | NH$_2$ | 5-Me | DB |
| 245 | S | C | C | [2-OMe]Ph | NH$_2$ | 5-Me | DB |
| 246 | S | C | C | [4-OAc]Ph | NH$_2$ | 5-Me | DB |
| 247 | S | C | C | [2-Me, 4-F]Ph | NH$_2$ | 5-Me | DB |
| 248 | S | C | C | [2-Me, 4-Cl]Ph | NH$_2$ | 5-Me | DB |
| 249 | S | C | C | Th(2) | NH$_2$ | 5-Me | DB |
| 250 | S | C | C | [3-Me]Th(2) | NH$_2$ | — | DB |
| 251 | S | C | C | [3-Me]Th(2) | NH$_2$ | 5-Me | DB |
| 252 | S | C | C | [3-Me]Th(2) | NH$_2$ | 8-Me | DB |
| 253 | S | C | C | Th(3) | NH$_2$ | 5-Me | DB |
| 254 | S | C | C | [2-Me]Th(3) | NH$_2$ | — | DB |
| 255 | S | C | C | [2-Me]Th(3) | NH$_2$ | 5-Me | DB |
| 256 | S | C | C | [2-Me]Th(3) | NH$_2$ | 8-Me | DB |
| 257 | S | C | C | [2-Me]Th(3) | NH$_2$ | 8-OMe | DB |
| 258 | S | C | C | [2-Me]Th(3) | NH$_2$ | 5,6-Me$_2$ | DB |
| 259 | S | C | C | [4-Me]Th(3) | NH$_2$ | — | DB |
| 260 | S | C | C | [2-Et]Th(3) | NH$_2$ | 5-Me | DB |
| 261 | S | C | C | [2-OMe]Th(3) | NH$_2$ | 5-Me | DB |
| 262 | S | C | C | [2,5-Cl$_2$]Th(3) | NH$_2$ | — | DB |
| 263 | S | C | C | [2,5-Cl$_2$]Th(3) | NH$_2$ | 5-Me | DB |
| 264 | S | C | C | [2,5-Me$_2$]Th(3) | NH$_2$ | — | DB |
| 265 | S | C | C | [2,5-Me$_2$]Th(3) | NH$_2$ | 5-Me | DB |
| 266 | S | C | C | [2-Cl, 3-Me]Th(4) | NH$_2$ | 5-Me | DB |
| 267 | S | C | C | Fu(2) | NH$_2$ | 5-Me | DB |
| 268 | S | C | C | Fu(3) | NH$_2$ | 5-Me | DB |
| 269 | S | C | C | [2-Me]Fu(3) | NH$_2$ | — | DB |
| 270 | S | C | C | [2-OMe]Fu(3) | NH$_2$ | — | DB |
| 271 | S | C | C | [2,5-Me$_2$]Fu(3) | NH$_2$ | — | DB |
| 272 | S | C | C | [2,5-Me$_2$]Fu(3) | NH$_2$ | 8-Br | DB |
| 273 | S | C | C | [2,5-Me$_2$]Fu(3) | NH$_2$ | 5-Me | DB |
| 274 | S | C | C | [2,5-Me$_2$]Fu(3) | NH$_2$ | 8-Me | DB |
| 275 | S | C | C | [1-Me]Pyr(2) | NH$_2$ | — | DB |
| 276 | O | C | C | [2-Me]Ph | NH$_2$ | — | DB |
| 277 | O | C | C | [2-Me]Ph | NH$_2$ | 5-Me | DB |
| 278 | O | C | C | [2-CF$_3$]Ph | NH$_2$ | — | DB |
| 279 | O | C | C | [2-CF$_3$]Ph | NH$_2$ | 5-Me | DB |
| 280 | O | C | C | [2-Me]Th(3) | NH$_2$ | — | DB |
| 281 | O | C | C | [2-Me]Th(3) | NH$_2$ | 5-Me | DB |
| 282 | O | C | C | [2-Et]Th(3) | NH$_2$ | 5-Me | DB |
| 283 | O | C | C | [2-OMe]Th(3) | NH$_2$ | 5-Me | DB |
| 284 | O | C | C | [2,5-Cl$_2$]Th(3) | NH$_2$ | — | DB |
| 285 | O | C | C | [2-Me, 5-Br]Th(3) | NH$_2$ | — | DB |
| 286 | O | C | C | [2,5-Me$_2$]Th(3) | NH$_2$ | — | DB |
| 287 | O | C | C | [3-Me]Fu(2) | NH$_2$ | — | DB |
| 288 | O | C | C | [2,5-Me$_2$]Fu(3) | NH$_2$ | — | DB |
| 289 | O | C | C | [1-Me]Pyr(3) | NH$_2$ | — | DB |
| 290 | N | C | C | [2-Me]Ph | NH$_2$ | — | DB |
| 291 | N | C | C | [2-Me]Ph | NH$_2$ | 7-Me | DB |
| 292 | N | C | C | [2-Me]Ph | NH$_2$ | 7-CH$_2$Ph | DB |
| 293 | N | C | C | [2-Me]Ph | NH$_2$ | 7-CH$_2$-[4-Cl]Ph | DB |
| 294 | N | C | C | [2-Me]Ph | NH$_2$ | 7-CH$_2$-[4-OMe]Ph | DB |
| 295 | N | C | C | [2-Me]Ph | NH$_2$ | 5,7-Me$_2$ | DB |

TABLE 2-continued

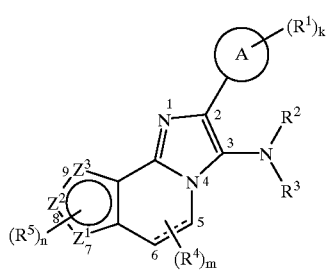

Examples of the compounds according to the invention represented by the formula (I-2).

| Compound No | $Z^1$ | $Z^2$ | $Z^3$ | (R¹)ₖ–A | NR²R³ | R⁴, R⁵ | 5–6 |
|---|---|---|---|---|---|---|---|
| 296 | N | C | C | [2-Me]Th(3) | NH₂ | 7-Me | DB |
| 297 | N | C | C | [2-Et]Th(3) | NH₂ | 7-CH₂Ph | DB |
| 298 | N | C | C | [2-Me]Th(3) | NH₂ | 5,7-Me₂ | DB |
| 299 | N | C | C | [2-Cl, 3-Me]Th(4) | NH₂ | 7-Me | DB |
| 300 | N | C | C | [2-Cl]Fu(3) | NH₂ | 7-CH₂Ph | DB |
| 301 | N | C | C | [2,5-Me₂]Fu(3) | NH₂ | 7-Me | DB |
| 302 | N | C | C | [1-Me]Pyr(2) | NH₂ | 7-Me | DB |
| 303 | C | S | C | [2-Me]Ph | NH₂ | 5-Me | DB |
| 304 | C | S | C | [3-Me]Th(2) | NH₂ | — | DB |
| 305 | C | S | C | [2-Me]Th(3) | NH₂ | 5-Me | DB |
| 306 | C | S | C | [1-Me]Pyr(2) | NH₂ | — | DB |
| 307 | C | O | C | [2-Me]Ph | NH₂ | — | DB |
| 308 | C | O | C | [2-Me]Th(3) | NH₂ | — | DB |
| 309 | C | C | S | [2-Cl]Ph | NH₂ | 5-Me | DB |
| 310 | C | C | S | [2-Me]Ph | NH₂ | — | DB |
| 311 | C | C | S | [2-Me]Ph | NH₂ | 5-Me | DB |
| 312 | C | C | S | [2-Me]Ph | NH₂ | 8-Me | DB |
| 313 | C | C | S | [2-CF₃]Ph | NH₂ | 5-Me | DB |
| 314 | C | C | S | [2-Me]Th(3) | NH₂ | 5-Me | DB |
| 315 | C | C | S | [4-Me]Th(3) | NH₂ | — | DB |
| 316 | C | C | S | [2,5-Me₂]Fu(3) | NH₂ | — | DB |
| 317 | C | C | S | [1-Me]Pyr(2) | NH₂ | — | DB |
| 318 | C | C | O | [2-Me]Ph | NH₂ | — | DB |
| 319 | C | C | O | [2-Me]Th(3) | NH₂ | 5-Me | DB |
| 320 | C | C | O | [3-Et, 5-Me]Fu(2) | NH₂ | — | DB |
| 321 | C | C | N | [2-Me]Ph | NH₂ | 9-Me | DB |
| 322 | C | C | N | [2-Me]Th(3) | NH₂ | 9-Me | DB |
| 323 | C | C | S | [2-Me]Ph | NH₂ | — | SB |
| 324 | S | C | C | [2-Me]Ph | NH₂ | 5,5-Me₂ | SB |
| 325 | S | C | C | [2-Me]Th(3) | NH₂ | 5,6-Me₂ | SB |
| 326 | S | C | C | [2,5-Me₂]Th(3) | NH₂ | — | SB |
| 327 | S | C | C | [2-Me]Fu(3) | NH₂ | — | SB |
| 328 | S | C | C | [2-Me]Ph | NH(Ac) | — | DB |
| 329 | S | C | C | [2-Me]Ph | NH(Ac) | 5-Me | DB |
| 330 | S | C | C | [2-Me]Th(3) | NH(Ac) | — | DB |
| 331 | S | C | C | [2,5-Me₂]Fu(3) | NH(Ac) | — | DB |
| 332 | N | C | C | [1-Me]Pyr(2) | NH(Ac) | 7-Me | DB |
| 333 | C | C | S | [2-Me]Ph | NH(Ac) | — | DB |
| 334 | S | C | C | [2-Me]Ph | NH(COPen) | 5-Me | DB |
| 335 | S | C | C | [2-Me]Ph | N(Ac)(Pr) | 5-Me | DB |
| 336 | S | C | C | [2-Me]Th(3) | N(Ac)(Pr) | — | DB |
| 337 | C | C | S | [2-Me]Ph | N(Ac)(Pr) | — | DB |
| 338 | S | C | C | [2-Me]Ph | N(Ac)(CH₂CH=CH₂) | 5-Me | DB |
| 339 | S | C | C | [2-Me]Th(3) | N(Ac)(CH₂CH=CH₂) | 5-Me | DB |
| 340 | S | C | C | [2-Me]Ph | NH(Et) | — | DB |
| 341 | S | C | C | [2-Me]Ph | NH(Et) | 5-Me | DB |
| 342 | S | C | C | [2-Me]Th(3) | NH(Et) | — | DB |
| 343 | S | C | C | [2,5-Me₂]Fu(3) | NH(Et) | — | DB |
| 344 | N | C | C | [2,5-Me₂]Fu(3) | NH(Et) | 7-Me | DB |
| 345 | C | C | S | [2-Me]Ph | NH(Et) | — | DB |
| 346 | C | C | S | [1-Me]Pyr(2) | NH(Et) | — | DB |
| 347 | S | C | C | [2-Me]Ph | NH(Hex) | 5-Me | DB |
| 348 | S | C | C | [2-Me]Ph | NH(CH₂CH=CH₂) | 5-Me | DB |
| 349 | S | C | C | [2-Me]Th(3) | NH(CH₂CH=CH₂) | 5-Me | DB |

TABLE 2-continued

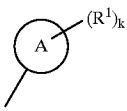

(I-2)

Examples of the compounds according to the invention represented by the formula (I-2).

| Compound No | $Z^1$ | $Z^2$ | $Z^3$ | A–$(R^1)_k$ | $NR^2R^3$ | $R^4$, $R^5$ | 5–6 |
|---|---|---|---|---|---|---|---|
| 350 | S | C | C | [2-Me]Ph | N(Et)(Pr) | 5-Me | DB |
| 351 | S | C | C | [2-Me]Th(3) | N(Et)(Pr) | — | DB |
| 352 | O | C | C | [2-Cl,3-Me]Th(4) | N(Et)(Pr) | — | DB |
| 353 | S | C | C | [2-Me]Ph | N(Et)(CH$_2$CH=CH$_2$) | 5-Me | DB |
| 354 | S | C | C | [2-Me]Th(3) | N(Et)(CH$_2$CH=CH$_2$) | 5-Me | DB |
| 355 | S | C | C | [2-Me]Ph | NH(CO$_2$Et) | — | DB |
| 356 | C | C | S | [2-Me]Ph | N(Et)(Pr) | — | DB |
| 357 | C | C | S | [3-Et]Th(2) | N(Et)(Pr) | — | DB |

Industrial Applicability

For illustrating superior inhibitory action on gastric acid secretion and superior protective action of gastric mucosa of the compounds of the invention, pharmacological and acute toxicity tests are shown below, which were conducted using experimental animal models. In Table 3, Table 4, Table 5, Table 6, and Table 7, the numbers of test compounds correspond to the compound numbers shown in Table 1 and Table 2.

Experiment 1 Inhibitory action on H$^+$/K$^+$-ATPase activity

According to the method of Hongo et al. [The Japanese Journal of Pharmacology, 52, p295, (1990)], a microsome fraction prepared from porcine gastric mucosa was used as a standard enzyme. The standard enzyme (10–20 µg protein) and the test compound (0.1–100 µM) dissolved in dimethylsulfoxide was incubated at 37° C. for 30 minutes in the 50 mM Tris-acetate buffer (pH7.4, containing 2 mM magnesium chloride, 5 mM potassium chloride). The enzyme reaction was started by adding adenosinetriphosphate (ATP)-Tris at the final concentration of 2 mM, and the reaction was kept at 37° C. for 15 minutes. The reaction was stopped by adding chilled 10% trichloroacetic acid. Inorganic phosphate released during the reaction was calorimetrically determined according to the method of Fiske-Subbarow [The Journal of Biological Chemistry, 66, p375, (1925)]. H$^+$/K$^+$-ATPase activity was determined by the difference of the enzyme activities under the conditions with or without potassium chloride. The inhibitory activities of test compounds were determined as the 50% inhibitory concentration (IC$_{50}$ value) from reaction-concentration curve, and the results are shown in Table 3.

TABLE 3

The inhibitory action on H$^+$/K$^+$-ATPase activity

| Test Compound | | IC$_{50}$(µM) | Test Compound | | IC$_{50}$(µM) |
|---|---|---|---|---|---|
| 3 | | 26.0 | 195 | | 8.8 |
| 6 | | 12.0 | 200 | hydrochloride | 1.2 |
| 7 | | 8.0 | 202 | hydrochloride | 9.8 |
| 9 | | 34.0 | 206 | | 2.3 |
| 10 | | 20.0 | 207 | hydrochloride | 9.3 |
| 12 | | 12.5 | 211 | hydrochloride | 2.4 |
| 15 | | 3.7 | 212 | hydrochloride | 1.9 |
| 21 | | 7.4 | 214 | | 7.0 |
| 22 | | 1.9 | 216 | hydrochloride | 2.5 |
| 24 | | 13.5 | 217 | hydrochloride | 4.7 |
| 26 | | 32.0 | 219 | hydrochloride | 3.6 |
| 38 | | 4.8 | 222 | hydrochloride | 2.0 |
| 46 | | 8.4 | 223 | hydrochloride | 4.5 |
| 54 | hydrochloride | 1.0 | 226 | | 1.9 |
| 75 | hydrochloride | 6.4 | 230 | | 20.0 |
| 78 | | 17.0 | 232 | | 17.0 |
| 83 | hydrochloride | 5.6 | 234 | | 7.6 |
| 91 | | 5.6 | 236 | | 4.7 |
| 94 | | 3.0 | 238 | | 2.9 |
| 96 | maleate | 17.5 | 239 | | 26.0 |
| 104 | | 12.0 | 245 | | 9.0 |
| 107 | | 33.0 | 248 | | 4.7 |
| 151 | hydrochloride | 7.8 | 254 | | 4.5 |
| 158 | hydrochloride | 13.0 | 255 | | 6.6 |
| 163 | hydrochloride | 4.6 | 264 | | 1.2 |
| 166 | hydrochloride | 23.0 | 271 | hydrochloride | 5.2 |
| 169 | | 5.8 | 275 | | 24.0 |
| 176 | | 9.0 | 291 | hydrochloride | 4.8 |
| 179 | | 4.8 | 292 | hydrochloride | 8.8 |
| 182 | | 11.0 | 310 | | 26.0 |
| 188 | | 10.5 | 311 | | 8.0 |
| 189 | hydrochloride | 6.8 | 340 | hydrochloride | 33.0 |
| 191 | hydrochloride | 5.2 | 356 | hydrochloride | 8.4 |
| 192 | | 4.4 | | | |

Experiment 2 Inhibition of gastric acid secretion observed under acute fistula method Male Wistar rats (6–8weeks) fasted for 24 hours (water ad libitum) were used. The rats were anesthetized by intraperitoneal administration of 1.25 g/kg of urethane. The abdomen was incised, and acute gastric fistula was connected to the stomach. Two ml of saline was injected into the stomach, and recovered every 20 minutes. The gastric acid secretion was determined by titrating of gastric juice by 150 mM sodium hydroxide up to pH7.0 using an autotitrator. Test compounds (30 mg/kg) suspended in a 0.5% aqueous sodium carboxymethylcellulose (CMC-Na) solution were administered intraduodenally. After 1 hour, gastric acid secretion was stimulated by subcutaneous administration of histamine dihydrochloride dissolved in saline (10 mg/kg). Inhibition (%) of gastric acid secretion was determined by calculating cumulative amount of the acid secretion during two hours after histamine stimulation and then comparing the cumulative amount with that in the control group. In the control group, only 0.5% aqueous CMC-Na solution was administered intraduodenally. The test results are shown in Table 4.

TABLE 4

Inhibition of gastric acid secretion observed under acute fistula method

| Test Compound | Inhibition (%) | Test Compound | Inhibition (%) |
| --- | --- | --- | --- |
| 3 | 82.2 | 179 | 52.8 |
| 6 | 79.6 | 182 | 58.4 |
| 7 | 74.9 | 188 | 79.1 |
| 9 | 90.7 | 205 hydrochloride | 86.0 |
| 26 | 90.8 | 207 hydrochloride | 67.4 |
| 46 | 73.8 | 214 | 56.0 |
| 75 hydrochloride | 73.3 | 221 hydrochloride | 66.7 |
| 158 hydrochloride | 83.6 | 222 hydrochloride | 72.6 |
| 166 hydrochloride | 54.9 | 223 hydrochloride | 60.1 |
| 176 | 49.9 | | |

Experiment 3 Inhibition of gastric acid secretion observed under stomach perfusion method Male Sprague Dawrey rats (6–7weeks) fasted for 24 hours were used (water ad libitum). The rats were anesthetized by intraperitoneal administration of 1.25 g/kg of urethane. The abdomen was incised, and gastral cavity was perfused with saline during experiment. The perfusate was titrated by 10 mM sodium hydroxide up to pH5.5 using an autotitrator in accordance with Stat-method. Gastric acid secretion was stimulated by intravenous administration of histamine dihydrochloride (8 mg/kg/hr). Two hours after histamine stimulation, a test compound (1–10 mg/kg) was administered intrapenetorially. The test compound was mixed with small amount of polysorbate-80, and the mixture was suspended in saline. The test compound was evaluated using $ID_{50}$ (dose showing 50% inhibition of acid secretion) which was calculated based on inhibition of the acid secretion observed one hour after administration of the compound. The results are shown in Table 5.

TABLE 5

Inhibition of gastric acid secretion observed under stomach perfusion method

| Test Compound | $IC_{50}$ (mg/kg) | Test Compound | $IC_{50}$ (mg/kg) |
| --- | --- | --- | --- |
| 3 | 3.4 | 103 | 7.4 |
| 6 | 5.0 | 158 hydrochloride | 8.6 |
| 9 | 3.1 | 230 | 6.2 |
| 10 | 4.2 | 232 | 3.2 |
| 12 | 7.2 | 234 | 1.8 |
| 24 | 5.4 | 236 | 1.4 |
| 26 | 2.8 | 254 | 1.1 |
| 43 | 7.0 | 255 | 1.0 |
| 56 | 6.5 | 271 hydrochloride | 2.4 |
| 78 | 1.6 | 291 hydrochloride | 6.4 |
| 94 | 5.8 | 310 | 3.0 |
| 96 maleate | 8.8 | 340 hydrochloride | 4.9 |

Experiment 4 Inhibition of ethanol-induced gastric lesion (Protection of gastric mucosa)

Male Wister rats (6–7weeks, 5 rats per group) fasted for 24 hours were used (water ad libitum). Test compound (30 mg/kg) suspended in 0.5% aqueous CMC-Na solution was orally administered. In the control group, only 0.5% aqueous CMC-Na solution was administered. Thirty minutes after administration, 0.5 ml/100 g body weight of ethanol was orally administered to cause gastric lesion. After one hour, the rat was killed by excessive amount of ether, and the stomach was removed and fixed with 2% formalin. After fixation, the stomach was dissected along the large curvature. The size of each of mucosal lesions was measured under dissecting microscope, and the total size of the lesions per rat was determined and used as ulcer index (mm). Inhibition of gastric lesion was determined by comparing the ulcer index in the control group and test group. Test results are shown in Table 6.

TABLE 6

Inhibition of ethanol-induced gastric lesion

| Test Compound | Inhibition (%) |
| --- | --- |
| 3 | 73.5 |
| 158 hydrochloride | 92.4 |
| 166 hydrochloride | 49.7 |
| 205 hydrochloride | 98.6 |
| 216 hydrochloride | 81.7 |
| 221 hydrochloride | 73.7 |
| 222 hydrochloride | 98.8 |
| 236 | 91.5 |
| 254 | 92.4 |
| 271 hydrochloride | 99.5 |

Experiment 5 Acute toxicity

Male ICR mice (6 weeks, 3 mice per group) fasted for 16 hours were used (water ad libitum). A test compound suspended in 5% aqueous gum arabic solution was orally administered. After administration, mortality of the animals was observed during 7 days and approximate lethal dose was determined. The results are shown in Table 7.

TABLE 7

Acute toxicity

| Test Compound | | Approximate lethal dose (mg/kg) | Test Compound | | Approximate lethal dose (mg/kg) |
|---|---|---|---|---|---|
| 3 | | >2,000 | 188 | | >2,000 |
| 6 | | >2,000 | 205 | hydrochloride | >2,000 |
| 9 | | >2,000 | 212 | hydrochloride | >2,000 |
| 26 | | >2,000 | 216 | hydrochloride | >2,000 |
| 91 | | >2,000 | 217 | hydrochloride | >2,000 |
| 158 | hydrochloride | >2,000 | 221 | hydrochloride | >2,000 |
| 166 | hydrochloride | >2,000 | 222 | hydrochloride | >2,000 |
| 176 | | >2,000 | 236 | | >2,000 |
| 179 | | >2,000 | 310 | | >2,000 |
| 182 | | >2,000 | | | |

The above experiments revealed that the compounds of the present invention exert inhibitory actions against $H^+/K^+$-ATPase activity and gastric acid secretion and protection of gastric mucosa. Furthermore, the compounds of the invention have low toxicity.

Accordingly, the present invention provides promised anti-ulcer drugs having inhibitory action on aggressive factors and promoting action on defensive factors. The anti-ulcer drugs of the invention are therefore useful for treating and preventing gastroduodenal ulcers, gastritis, reflex esophagitis, Zollinger-Erison syndrome, and the like.

A pharmaceutical composition containing one or more of the compound(s) (I) of the present invention or pharmaceutically acceptable salts or solvates thereof as an active ingredient may be used as the above-mentioned drugs. The pharmaceutical composition can be administered orally or parenterally in the form of tablets, powders, granules, capsules, pills, syrups, suppositories, injections, external preparations, drip injections, and the like. The pharmaceutical composition may be produced by conventional methods without difficulty. For instance, solid preparations for oral use may be prepared by a conventional method using vehicles, binders, disintegrators, lubricants, coloring agents, corrigents, and other commonly used additives. Examples of such vehicles may include lactose, corn starch, sucrose, glucose, crystalline cellulose, silica, sorbitol, and the like. Examples of such binders are polyvinylalcohol, polyvinylether, ethylcellulose, gum arabic, tragacanth, gelatin, hydroxypropylcellulose, hydroxypropylstarch, polyvinylpyrrolidone, and the like. Examples of disintegrators may include starch, agar, gelatin, crystalline cellulose, calcium carbonate, sodium bicarbonate, calcium citrate, calcium carboxymethylcellulose, dextran, and the like. Examples of lubricants may include magnesium stearate, talc, polyethyleneglycol, silica, hydrogenated vegetable oil, and the like. The coloring agents may be selected from those which are approved as additives for pharmaceutical preparations. Examples of corrigents are powdered cocoa, mentha oil, powdered cinnamon bark, and the like. Tablets and granules may be coated with sugar, gelatin, and the like. Injections can readily be prepared by a conventional method, using, if necessary, distilled water, pH-regulating agent, buffering agent, stabilizer, solubilizer, and other commonly used additives.

Dosage of the compound of the invention, when used as an anti-ulcer agent, will vary according to environmental conditions, such as symptom, age, body weight of particular patient and administration route. The dosage may be usually 3 to 1,500 mg, preferable 5 to 800 mg per day for adults. Increased or decreased dosage is also acceptable, and it may be administered once a day or after divided into some portions.

The compounds of the invention may conveniently be administered for a continued period of time, for example, for a week or more.

The phamaceutical composition of the invention containing the compound (I), pharmaceutically acceptable salt or solvate thereof useful for the treatment of the above-mentioned diseases may also include one or more pharmacologically active constituents, such as antacids (magnesium carbonate, magnesium hydroxide, aluminum hydroxide, magnesium aluminate etc.), non-steroidal anti-inflammatory agents (indomethacin, aspirin, naproxen etc.), steroids, nitrite scavengers (ascorbic acid, aminosulphonic acid etc.), antibiotics (penicillins, tetracyclines etc.) and, if appropriate, enzymes, vitamins, or amino acids.

Special attention should be directed to a combination of the compound according to the invention with other agents inhibiting acid secretion, such as $H_2$ blockers (cimetidine or ranitidine etc.) or with so-called peripheral anticholinergic agents (pirenzepine, telenzepine or zolenzepine etc.) with the aim of reinforcing the principal action in an additive or superadditive sense and/or eliminating or reducing side effects, or with antibacterial substances (cephalosporins, tetracyclines, nalidixic acid etc.) with the aim of eradication of *Helicobacter pylori*.

BEST MODE FOR CARRYING OUT THE INVENTION

The present invention is illustrated in more detail with working examples. However, the present invention is not limited thereto. Starting compounds used in the present invention include novel compounds. Processes for preparing such starting compounds are also described below under preparations. In Preparations and Examples, IR means infrared spectrum, wherein data is given using $cm^{-1}$ unit, and the method used is shown in parentheses, MS means mass spectrum, HRMS means high-resolution mass spectrum wherein the method used is shown in parentheses, and NMR means proton nuclear magnetic resonance spectrum, wherein data is given in ppm and the solvent used is shown in parentheses using following abbreviations.

| CDCL | Chloroform-d |
|---|---|
| DMSO | Dimethylsulfoxide-$d_6$ |
| ACET | Acetone-$d_6$ |
| METH | Methanol-$d_4$ |

Preparation 1
4-(4-Methoxybenzyl)amino-6-methylthieno[3,2-c]pyridine

To a solution of 5.1 g of sodium hydride in oil (prewashed by decantation with hexane.) in 60 ml of dry tetrahydrofuran was added dropwise 30 g of triethyl 2-phosphonopropionate over a period of 30 minutes under dry argon atmosphere at room temperature. After the mixture was stirred for further 1 hour, a solution of 11.8 g of 2-thiophenealdehyde in 30l of tetrahydrofuran was added dropwise. The mixture was stirred at room temperature for 2 hours. The reaction mixture was poured into water, and extracted with ethyl acetate. The extract was washed successively with water and saturated saline, dried over anhydrous magnesium sulfate. Drying agent was removed by filtration, and the solvent was removed under reduced pressure. The residue was purified by column chromatography on silica gel to give 11.0 g of ethyl 2-methyl-3-(2-thienyl)acrylate as a yellow oil. Next, 150 ml of ethanol and 60 ml of aqueous 2N sodium hydroxide were added to the oil, and the mixture was refluxed for 1 hour. After cooling, ethanol was removed under reduced pressure, and the residue was acidified with dilute hydrochloric acid. Crystalline precipitate was collected by filtration to give 8.2 g of 2-methyl-3-(2-thienyl) acrylic acid as a white powder.

To a mixture of 8.2 g of 2-methyl-3-(2-thienyl)acrylic acid and 9.5 ml of triethylamine in 45 ml of acetone was added dropwise 7.2 ml of ethyl chlorocarbonate over a period of 30 minutes under ice-cooling with stirring. After being stirred for 1 hour, a solution of 5.1 g of sodium azide in 10 ml of water was added dropwise over 30 minutes, and then stirred for 1 hour. The reaction mixture was poured into water and extracted with benzene. The extract was washed with water and saturated saline, and dried over anhydrous magnesium sulfate. Drying agent was removed by filtration, and the solvent was removed under reduced pressure, and then 15 ml of diphenylether was added to the residue. The resultant solution was added dropwise to a mixture of 14 ml of tri-n-butylamine and 35 ml of diphenylether at 200° C. When addition was complete, the reaction mixture was allowed to cool and the crystalline precipitate was washed with diethyl ether to give 6.2 g of 6-methylthieno[3,2-c]pyridin-4(5H)-one as a pale yellow powder.

A solution of 6.2 g of 6-methylthieno[3,2-c]pyridin-4(5H)-one in 30 ml of phosphoryl chloride was heated under reflux for 1 hour. After being cooled, the excess phosphoryl chloride was removed under reduced pressure, and the residue was poured into ice water, made basic with aqueous 2N sodium hydroxide and extracted with chloroform. The extract was washed successively with water and saturated saline, and dried over anhydrous magnesium sulfate. The drying agent was removed by filtration, and the solvent was removed under reduced pressure to give 7.0 g of 4-chloro-6-methylthieno[3,2-c]pyridine as a brown oily material.

A mixture of 7.0 g of 4-chloro-6-methylthieno[3,2-c]pyridine and 28 ml of 4-methoxybenzylamine was stirred at 170° C. for 4 hours. After being cooled, the reaction mixture was diluted with 400 ml of chloroform, washed with water and saturated saline, dried over anhydrous magnesium sulfate. The drying agent was removed by filtration, and the solvent was removed under reduced pressure. The residue was purified by column chromatography on silica gel to give 10 g of the title compound as a yellow oily material.

IR(Neat): 3420, 3080, 3000, 2950, 2920, 2840, 1680, 1590, 1544, 1510, 1444, 1400, 1334, 1302, 1248, 1172, 1158, 1108, 1090, 1060, 1030,888,810,690.

NMR(CDCL): 7.37(2H,d,J=9.0 Hz), 7.18(2H,s), 6.98 (1H,s), 6.87(2H,d,J=9.0 Hz), 5.10–4.60(1H,br), 4.70(2H,d, J=5.0 Hz), 3.79(3H,s), 2.50(3H,s).

Preparation 2
4-Amino-6-methylthieno[3,2-c]pyridine

To a solution of 24 g of 4-(4-methoxybenzyl)amino-6-methylthieno[3,2-c]pyridine in 80 ml of trifluoroacetic acid was added 15 ml of concentrated sulfuric acid, and the mixture was stirred at ambient temperature for 30 minutes. The reaction mixture was poured into ice water, rendered alkaline by the addition of 28% ammonia water and extracted with chloroform. The extract was washed with water and saturated saline, dried over anhydrous magnesium sulfate. The drying agent was removed by filtration, and the solvent was removed under reduced pressure. The residue was purified by column chromatography on silica gel and recrystallized from chloroform/petroleum ether to give 15 g of the title compound as a white powder.

m.p.: 136.0–136.5° C.

IR(KBr): 3470, 3300, 3140, 1632, 1584, 1540, 1452, 1420, 1370, 1346, 1270, 1080, 894, 802, 700.

NMR(CDCL): 7.20(2H,s), 7.00(1H,s), 5.40–5.00(2H,br), 2.45(3H,s).

Preparation 3
7-Aminothieno[2,3-c]pyridine

To a solution of 18 g of thieno[2,3-c]pyridine in 300 ml of chloroform was added 33 g of 3-chloroperbenzoic acid portionwise with ice-cooling over a period of 1 hour, and the mixture was stirred for further 1 hour under the same conditions. The reaction mixture was diluted with 400 ml of chloroform, washed successively with water, a saturated sodium carbonate solution and saturated saline, and dried over anhydrous magnesium sulfate. The drying agent was removed by filtration, and the solvent was removed under reduced pressure to give 16.6 g of thieno[2,3-c]pyridine-N-oxide as a white powder.

To a solution of 16.6 g of thieno[2,3-c]pyridine-N-oxide in 500 ml of chloroform was added 25 g of p-toluenesulfonyl chloride portionwise with ice-cooling over a period of 1 hour. After the reaction mixture was stirred for further 30 minutes under the same conditions, 250 ml of 10% ammonia water was added, and stirred at ambient temperature for 16 hours. The reaction mixture was diluted with 400 ml of chloroform, washed with water and saturated saline, and dried over anhydrous magnesium sulfate. The drying agent was removed by filtration, and the solvent was removed under reduced pressure. The residue was purified by column chromatography on silica gel to give 2.8 g of the title compound as a brown oily material.

IR(Neat): 3450, 3320, 3150, 1625, 1580, 1552, 1488, 1459, 1400, 1304, 1245, 1152,1110,1035, 1005,800,750.

NMR(CDCL): 8.00(1H,d,J=6.0 Hz), 7.52(1H,d,J=5.0 Hz), 7.24(1H,d,J=5.0 Hz), 7.1 1(1H,d,J=6.0 Hz), 5.33(2H, brs).

Preparation 4
1-Amino-8-chloro-7-methoxyisoquinoline

To a solution of 1.3 g of 8-chloro-7-methoxyisoquinoline-N-oxide in 40 ml of pyridine was added 1.4 g of p-toluenesulfonyl chloride, and the mixture was stirred at ambient temperature for 2 hours. The solvent was removed under reduced pressure, 20 ml of ethanolamine was added to the resultant residue, and then the mixture was stirred for further 3 hours. The reaction mixture was poured into water, and the crystalline precipitate was collected by filtration, washed with water, and dried under reduced pressure to give 0.8 g of the title compound as a yellow powder.

IR(KBr): 3540, 3300, 3130, 3050, 2950, 2850, 1633, 1600, 1540, 1518, 1450, 1423, 1370, 1330, 1290, 1265, 1068, 1025, 957, 818.

NMR(CDCL): 7.82(1H,d,J=6.0 Hz), 7.60(1H,d,J=9.0 Hz), 7.32(1H,d,J=9.0 Hz), 6.90(1H,d,J=6.0 Hz), 6.50–6.02 (2H,br), 4.00(3H,s).

Preparation 5
1-Amino-7-methoxyisoquinoline

A solution of 8.0 g of 7-methoxyisoquinoline in 45 ml of N,N-dimethylaniline was warmed at 60° C., and then 5.9 g of sodium amide was added. The reaction mixture was heated at 130° C. over a period of 2 hours, and stirred for further 1 hour under the same conditions. After being cooled, the reaction mixture was poured into ice water and extracted with chloroform. The extract was washed with water, and dried over anhydrous magnesium sulfate. The drying agent was removed by filtration, and the solvent was removed under reduced pressure. The residue was purified by column chromatography on silica gel and recrystallized from benzene to give 5.7 g of the title compound as colorless flakes.

m.p.: 137.5–138.0° C.

IR(KBr): 3440, 3340, 3150, 3080, 2980, 2850, 1652, 1605, 1569, 1516, 1455, 1428, 1385, 1350, 1298, 1241, 1209,1190, 1136, 1085, 1032,915,890,853,830.

NMR(CDCL): 7.84(1H,d,J=6.0 Hz), 7.59(1H,d,J=9.0 Hz), 7.20(1H,dd,J=2.0 Hz,9.0 Hz), 7.07(1H,d,J=2.0 Hz), 6.95(1H,d,J=6.0 Hz), 5.33(2H,brs), 3.82(3H,s).

Preparation 6
2'-Methyl-2-bromoacetophenone

To a solution of 3.0 g of 2'-methylacetophenone in 60 ml of acetic acid was added successively 9.7 ml of 47% hydrobromic acid and 8.6 g of pyridinium hydrobromide perbromide, and the mixture was stirred at room temperature for 1 hour. The reaction mixture was poured into water and extracted with ethyl acetate. The extract was washed with water and a saturated sodium carbonate solution, and dried over anhydrous magnesium sulfate. The drying agent was removed by filtration, and the solvent was removed under reduced pressure to give 5.4 g of the title compound as a colorless oily material.

IR(Neat): 3075, 3030, 2980, 2940, 1682, 1604, 1573, 1490, 1459, 1435, 1385, 1358, 1295, 1260, 1210, 1189, 1040, 1008, 978,754,735.

NMR(CDCL): 7.72–7.05(4H,m), 4.36(2H,s), 2.49(3H,s).

Preparation 7
2-(2-Methylphenyl)imidazo[2,1-a]isoquinoline

A mixture of 3.0 g of 1-aminoisoquinoline, 6.7 g of 2'-methyl-2-bromoacetophenone and 17.5 g of sodium bicarbonate in 50 ml of ethanol was refluxed for 2 hours. After being cooled, the reaction mixture was poured into water and extracted with ethyl acetate. The extract was washed with water and saturated saline, and dried over anhydrous magnesium sulfate. The drying agent was removed by filtration, and the solvent was removed under reduced pressure. The residue was purified by column chromatography on silica gel and recrystallized from dichloromethane/petroleum ether to give 4.4 g of the title compound as pale brown prisms.

m.p.: 93.0° C.

IR(KBr): 3070–3020, 2960, 1640, 1604, 1538, 1515, 1480, 1458, 1382, 1316, 1208, 1193, 1144, 1120, 1078, 1045,938,870,788,770, 730,700.

NMR(CDCL): 8.90–8.60(1H,m), 8.15–7.83(1H,m), 7.79 (1H,d,J=7.0 Hz), 7.70–7.10(7H,m), 6.90(1H,d,J=7.0 Hz), 2.54(3H,s).

Preparation 8
9-Methoxy-2-(2-methylphenyl)-5,6-dihydroimidazo[2,1-a]isoquinoline To a solution of 3.1 g of 7-methoxy-3,4-dihydroisoquinoline in 40 ml of methylene chloride was added 7.3 g of 2'-methyl-2-bromoacetophenone, and the mixture was stirred at room temperature for 4 hours and evaporated in vacuo. To the resultant residue was added a mixture of 20 ml of acetic acid and 10.4 g of ammonium acetate, and the mixture was refluxed for 6 hours. After being cooled, the reaction mixture was poured into aqueous 2N sodium hydroxide and extracted with ethyl acetate. The extract was washed with water and saturated saline, and dried over anhydrous magnesium sulfate. The drying agent was removed by filtration, and the solvent was removed under reduced pressure. The residue was purified by column chromatography on silica gel to give 0.7 g of the title compound as a brown viscous material.

IR(Neat): 3070, 3020, 2960, 2910, 2850, 1617, 1578, 1548, 1500, 1482, 1465, 1442, 1380, 1332, 1309, 1280, 1252, 1227, 1212, 1180, 1123,1078, 1036, 947, 915,868, 810,745.

NMR(CDCL): 8.09–7.80(1H,m), 7.74(1H,d,J=2.0 Hz), 7.38–7.11(4H,m), 7.05(1H,s), 6.85(1H,dd,J=2.0 Hz,6.0 Hz), 4.17(2H,t,J=7.0 Hz), 3.90(3H,s), 3.08(2H,t,J=7.0 Hz), 2.53 (3H,s).

Preparation 9
9-Methoxy-5-methyl-2-(2-methylphenyl)-5,6-dihydroimidazo[2,1-a]isoquinoline To a solution of 12 g of 7-methoxy-3-methyl-3,4-dihydroisoquinoline in 120 ml of dimethoxyethane was added 16 g of 2'-methyl-2-bromoacetophenone, and the mixture was stirred at room temperature for 14 hours. The resulting white powder was collected by filtration to give 13 g of 7-methoxy-3-methyl-2-(2-methylphenyl)-3,4-dihydroisoquinolinium bromide. A mixture of this white powder, 80 ml of acetic acid and 12.8 g of ammonium acetate was then refluxed for 3 hours. After being cooled, the reaction mixture was poured into water, rendered alkaline by the addition of a saturated sodium carbonate solution and extracted with ethyl acetate. The extract was washed with water and saturated saline, and dried over anhydrous magnesium sulfate. The drying agent was removed by filtration, and the solvent was removed under reduced pressure. The residue was purified by column chromatography on silica gel to give 5.3 g of the title compound as a yellow oily material.

IR(Neat): 3060, 3010, 2970, 2940, 2900, 2840, 1612, 1532, 1493, 1482, 1462, 1455, 1440, 1372, 1338, 1287, 1274, 1241, 1220, 1170, 1078, 1032, 945, 870, 742.

NMR(CDCL): 8.02–7.78(1H,m), 7.71(1H,d,J=3.0 Hz), 7.40–7.08(5H,m), 6.83(1H,dd,J=3.0 Hz,9.0 Hz), 4.69–4.02 (1H,m), 3.88(3H,s), 3.38–2.72(2H,m), 2.52(3H,s), 1.52(3H, d,J=7.0 Hz).

Preparation 10
9-Methoxy-5-methyl-2-(2-methylphenyl)imidazo[2,1-a]isoquinoline

To a solution of 4.9 g of 9-methoxy-5-methyl-2-(2-methylphenyl)-5,6-dihydroimidazo[2,1-a]isoquinoline in 30 ml of decalin was added 0.97 g of palladium on activated carbon (Pd 10%) and the mixture was refluxed for 6 hours. After being cooled and an addition of 200 ml of chloroform, the mixture was filtered and the filtrate was evaporated in vacuo. The resultant residue was crystallized from a mixture of hexane and ethyl acetate(6:1) to give 3.0 g of the tide compound.

IR(KBr): 2940, 2830, 1618, 1538, 1520, 1498, 1481, 1460, 1440, 1405, 1345, 1280, 1259, 1247, 1210, 1174, 1130, 1100, 1030, 872, 830, 800,770, 730.

NMR(CDCL): 8.10(1H,d,J=2.0 Hz), 8.07–7.81(1H,m), 7.59(1H,s), 7.55(1H,d,J=9.0 Hz), 7.40–7.02(4H,m), 6.79 (1H,s), 3.98(3H,s), 2.59(6H,s).

Preparation 11
2-(2-Methyl-3-thienyl)furo[3,2-c]imidazo[1,2-a]pyridine

A solution of 6.1 g of 2-(5-bromo-2-methyl-3-thienyl)furo[3,2-c]imidazo[1,2-a]pyridine, which was prepared by the reaction of 4-aminofuro[3,2-c]pyridine and 5-bromo-3-bromoacetyl-2-methylthiophene in a similar manner to that of aforementioned Preparation 7, in 50 ml of tetrahydrofuran was added dropwise to a solution of 3.5 g of lithium aluminum hydride in 50 ml of tetrahydrofuran. When addition was complete, the mixture was refluxed for 2 hours. After being cooled, excessive lithium aluminum hydride was decomposed by the addition of hydrous ether, and the mixture was dried over anhydrous magnesium sulfate. The drying agent was removed by filtration, and the solvent was removed under reduced pressure to give 4.5 g of the title compound as a white powder.

m.p.: 83.5–85.0° C.

IR(KBr): 3370, 3140, 3090, 2910, 1671, 1645, 1574, 1510, 1440, 1402, 1338, 1305, 1270, 1240, 1148, 1136, 1079, 1062, 1038, 890, 855,768,738,712,682.

NMR(CDCL): 7.98(1H,d,J=8.0 Hz), 7.71(1H,d,J=2.0 Hz), 7.65(1H,s), 7.56(1H,d,J=5.0 Hz), 7.31(1H,d,J=2.0 Hz), 7.13(1H,d,J=5.0 Hz), 7.08(1H,d,J=8.0 Hz), 2.69(3H,s)

EXAMPLE 1

3-Amino-2-(2-methylphenyl)imidazo[2,1-a]isoquinoline (Compound 3)

In a mixture of 30 ml of acetic acid and 6 ml of water was dissolved 2.5 g of 2-(2-methylphenyl)imidazo[2,1-a] isoquinoline with ice-cooling and stirring. A solution of 3.4 g of sodium nitrite in 12 ml of water was added portionwise to this solution and then the mixture was stirred at room temperature for 1 hour. The resulting crude crystals were collected by filtration and washing. The obtained powder was suspended in a mixture of 30 ml of acetic acid and 15 ml of water. To this suspension was added portionwise 6.3 g of zinc powder. After 1 hour, the reaction mixture was filtered, the filtrate was rendered alkaline by the addition of 28% ammonia water, and extracted with ethyl acetate. The extract was washed with water and saturated saline, and dried over anhydrous magnesium sulfate. The drying agent was removed by filtration, and the solvent was removed under reduced pressure. The residue was purified by column chromatography on silica gel and recrystallized from ethyl acetate/petroleum ether to give 2.1 g of the title compound as orange needles.

m.p.: 151.0–153.0° C.

Analysis Calcd.for $C_{18}H_{15}N_3$: C, 79.10%; H, 5.53%; N, 15.37%; Found: C, 79.29%; H, 5.62%; N, 15.18%.

IR(KBr): 3370, 3120–3080, 1645, 1612, 1582, 1528, .1490, 1458, 1382, 1277, 1146, 893, 764,725.

NMR(CDCL): 8.76–8.40(1H,m), 7.78(1H,d,J=7.0 Hz), 7.69–7.09(7H,m), 6.95(1H,d,J=7.0 Hz), 3.28(2H,brs), 2.37 (3H,s).

MS(EI)m/z: 273($M^+$), 257, 144.

EXAMPLE 2

3-Amino-2-(2,5-dimethyl-3-furyl)imidazo[1,2-a]thieno[3,2-c]pyridine (Compound 271) hydrochloride To a solution of 4.0 g of 2-(2,5-dimethyl-3-furyl)imidazo [1,2-a]thieno[3,2-c]pyridine, which was prepared by the reaction of 4-aminothieno[3,2-c]pyridine and 3-bromoacetyl-2,5-dimethylfuran in a similar manner to that of aforementioned Preparation 7, in 60 ml of dioxane was added dropwise 6 ml of isopentyl nitrite at 60° C. When addition was complete, the mixture was stirred for further 20 minutes at 70° C. After being cooled, precipitated crystalline was collected by filtration, washed with ether, and added with 9.8 g of zinc powder after addition of 40 ml of acetic acid and 30 ml water under ice-cooling. The mixture was stirred for 16 hours. The solution was filtered, the filtrate was rendered alkaline by the addition of 28% ammonia water, and extracted with ethyl acetate. The extract was washed with water and saturated saline, and dried over anhydrous magnesium sulfate. The drying agent was removed by filtration, and the solvent was removed under reduced pressure. The residue was purified by column chromatography on silica gel to give 2.3 g of 3-Amino-2-(2,5-dimethyl-3-furyl)imidazo[1,2-a]thieno[3,2-c]pyridine(Compound 271) as a pale yellow amorphous solid. To a solution of 2.3 g of the product in 100 ml of ether was added a saturated solution of hydrogen chloride in ether, precipitated crystalline was collected by filtration, and recrystallized from ethanol to give 2.0 g of the title compound as pale yellow plates.

m.p.: 210.0–211.5° C.(dec.).

IR(KBr): 3370, 3300, 3140, 3050, 2650, 1665, 1630, 1623, 1580, 1538, 1445, 1420, 1400, 1378, 1265, 1224, 1000, 710.

NMR(DMSO): 8.60(1H,d,J=7.5 Hz), 8.48(1H,d,J=5.0 Hz), 8.18(1H,d,J=5.0 Hz), 8.08(1H,d,J=7.5 Hz), 6.44(1H,s), 2.42(3H,s), 2.35(3H,s).

EXAMPLE 3

Compounds obtained in the same manner as in Examples 1 and 2 are collectively shown below.

3-Amino-2-(2-fluorophenyl)imidazo[2,1-a]isoquinoline (Compound 1) hydrochloride m.p.: 221.0–229.0° C.(dec.).

IR(KBr): 3500, 3130, 3060, 2950, 2760, 2700, 2570, 1670, 1634, 1575, 1550, 1509,1460,1430,1332, 1270,1214, 1109,790,760.

NMR(DMSO): 9.23–8.89(1H,m), 8.58(1H,d,J=7.8 Hz), 8.19–7.18(8H,m).

3-Amino-2-(2-chlorophenyl)imidazo[2,1-a]isoquinoline (Compound 2)

m.p.: 185.0–187.0° C.

IR(KBr): 3360–3150, 1645, 1610, 1580, 1483, 1460, 1433, 1380, 1050, 1030, 895, 785, 760.

NMR(CDCL): 8.81–8.46(1H,m), 8.01–7.15(8H,m), 7.01 (1H,d,J=7.0 Hz), 3.60–3.23(2H,brs).

3-Amino-9-fluoro-2-(2-methylphenyl)imidazo[2,1-a] isoquinoline (Compound 4)

m.p.: 191.0–192.5° C.

IR(KBr): 3390, 3140, 2930, 1615, 1578, 1559, 1523, 1499, 1455, 1419, 1379, 1276, 1248,1218, 1181, 1140, 1073,920,868,813,755, 723.

NMR(CDCL): 8.22(1H,dd,J=2.0 Hz,9.8 Hz), 7.84–7.11 (6H,m), 7.77(1H,d,J=7.0 Hz), 6.98(1H,d,J=7.0 Hz), 3.51–3.10(2H,br), 2.42(3H,s).

3-Amino-9-chloro-2-(2-methylphenyl)imidazo[2,1-a] isoquinoline (Compound 6)

m.p.: 190.0–191.0° C.

IR(KBr): 3380, 3320, 1608, 1582, 1518, 1480, 1438, 1408, 1386, 1368, 1104, 826, 726.

NMR(DMSO): 8.34(1H,d,J=2.0 Hz), 8.16(1H,d,J=7.0 Hz), 7.83(1H,d,J=9.0 Hz), 7.70–7.10(6H,m), 5.10(2H,brs), 2.46(3H,s).

3-Amino-10-chloro-2-(2-methylphenyl)imidazo[2,1-a] isoquinoline (Compound 7)

m.p.: 147.0–147.5° C.

IR(KBr): 3360, 3100, 1640, 1610, 1575, 1520, 1482, 1451, 1377, 1270, 1140, 759.

NMR(CDCL): 8.71–8.44(1H,br), 7.81–6.70(8H,m), 3.30 (2H,s), 2.38(3H,s).

3-Amino-5-methyl-2-(2-methylphenyl)imidazo[2,1-a] isoquinoline (Compound 9)

m.p.: 158.0–159.0° C.(dec.).

Analysis Calcd.for $C_{19}H_{17}N_3$: C, 79.41%; H, 5.96%; N, 14.62%; Found: C, 79.39%; H, 6.07%; N, 14.58%.

MS(EI)m/z: 287($M^+$), 270, 158, 143.

HRMS(EI)m/z: 287.14189(Calcd.for: $C_{19}H_{17}N_3$; 287.3634).

IR(KBr): 3410, 3180, 3060, 1647, 1610, 1575, 1533, 1491, 1480, 1456, 1390, 1352, 1289, 1260, 1210, 1160, 1040,945, 868,828,760,745,720.

NMR(CDCL): 8.75–8.50(1H,m), 7.58–7.12(7H,m), 6.58 (1H,brs), 3.32(2H,brs), 2.87(3H,s), 2.35(3H,s).

3-Amino-9-methyl-2-(2-methylphenyl)imidazo[2,1-a] isoquinoline (Compound 10)

m.p.: 172.5–173.0° C.

IR(KBr): 3470, 3380, 3300, 3170, 3060, 3030, 2960, 2930, 1624, 1582, 1520, 1490, 1450, 1410,1378, 1302,1275, 1182, 1084, 1034,945,910,855,822, 770, 726.

NMR(CDCL): 8.48(1H,brs), 7.75(1H,d,J=7.0 Hz), 7.60–7.12(6H,m), 6.96(1H,d,J=7.0 Hz), 3.30(2H,brs), 2.50 (3H,s), 2.40(3H,s).

3-Amino-2-(2-methylphenyl)-7-propylimidazo[2,1-a] isoquinoline (Compound 13)

m.p.: 137.0–138.0° C.

IR(KBr): 3370, 3120, 2950, 2930, 2860, 1640, 1608, 1580, 1520, 1490, 1450, 1382, 1275,1150, 1080,763,720.

NMR(CDCL): 8.63(1H,dd,J=2.0 Hz,7.6 Hz), 7.91(1H,d, J=7.8 Hz), 7.70–7.20(7H,m), 3.31(2H,brs), 3.00(2H,t,J=8.0 Hz), 2.41(3H,s), 2.10–1.46(2H,m), 1.03(3H,t,J=8.0 Hz).

3-Amino-6-isopentyl-2-(2-methylphenyl)imidazo[2,1-a] isoquinoline (Compound 15)

m.p.: 150.5–151.5° C.

IR(KBr): 3440, 3110, 3060, 2960, 2930, 2875, 1645, 1622, 1608, 1582, 1520, 1492, 1465, 1455, 1392, 1369, 1230, 860, 840–810, 760, 724, 690.

NMR(CDCL): 8.80–8.60(1H,m), 7.95–7.14(8H,m), 3.30 (2H,brs), 3.10–2.75(2H,m), 2.40(3H,s), 1.85–1.45(3H,m), 1.06(6H,d,J=6.0 Hz).

3-Amino-6-methoxymethyl-2-(2-methylphenyl)imidazo [2,1-a] isoquinoline (Compound 16)

m.p.: 102.5–103.5° C.

IR(KBr): 3430, 3340, 3070, 2940, 2900, 2860, 2830, 1650, 1610, 1580, 1522, 1488, 1455, 1445, 1398, 1386, 1352, 1295, 1278, 1225, 1200, 1150, 1023, 1096, 1050, 1030, 970, 913, 848,760, 740, 700.

NMR(CDCL): 8.85–8.55(1H,m), 8.10–7.29(8H,m), 4.77 (2H,s), 3.48(3H,s), 3.32(2H,brs), 2.41(3H,s).

3-Amino-2-(2-methylphenyl)-6-(phenoxymethyl)imidazo [2,1-a]isoquinoline (Compound 17)

m.p.: 187.0–188.5° C.

IR(KBr): 3450, 3330, 3170, 3070, 2930, 2880, 1651, 1615, 1600, 1590, 1528, 1495, 1480, 1458, 1380, 1350, 1330, 1296, 1230, 1175, 1150, 1100, 1080, 1029, 1005, 989, 860, 816, 752, 723, 688.

NMR(CDCL): 8.80–8.58(1H,m), 7.91(1H,s), 7.87–6.85 (12H,m), 5.25(2H,s), 3.30(2H,brs), 2.38(3H,s).

3-Amino-7-hydroxymethyl-2-(2-methylphenyl)imidazo[2, 1-a]isoquinoline (Compound 18)

IR(KBr): 3500, 3350, 3230, 3000, 2970, 2900, 1652, 1592, 1525, 1496, 1455, 1390,1320,1280, 1254, 1220, 1015, 777.

NMR(DMSO): 8.60–8.01(2H,m), 7.81–7.07(7H,m), 5.58–5.22(1H,m), 5.20–4.66(4H,br), 2.48(3H,s).

3-Amino-9-(1-hydroxyethyl)-2-(2-methylphenyl)imidazo [2,1-a]isoquinoline (Compound 19)

m.p.: 227.5–229.0° C.

IR(KBr): 3460, 3180, 2980, 2940, 1648, 1624, 1590, 1522, 1490, 1445, 1412, 1378, 1272, 1073, 824, 767, 721.

NMR(DMSO): 8.46(1H,brs), 8.12(1H,d,J=7.0 Hz), 7.88–7.12(7H,m), 5.40(1H,d,J=4.0 Hz), 5.204.78(1H,m), 4.98(2H,brs), 2.48(3H,s), 1.44(3H,d,J=6.0 Hz).

3-Amino-2-(2-methylphenyl)-9-phenylimidazo[2,1-a] isoquinoline (Compound 20) hydrochloride m.p.: 229.0° C.(dec.).

IR(KBr): 3420, 3100, 3060, 2780, 2600, 1668, 1630, 1604, 1558, 1491, 1462, 1422, 1300, 1278, 1255, 1160,900, 830,753,722,682.

NMR(DMSO): 9.54(1H,s), 8.64(1H,d,J=7.6 Hz), 8.20–7.28(12H,m), 2.46(3H,s).

3-Amino-6-(4-methoxyphenyl)-2-(2-methylphenyl)imidazo [2,1-a]isoquinoline (Compound 21)

m.p.: 182.0–183.0° C.

IR(KBr): 3400, 1640, 1610, 1574, 1506, 1454, 1394, 1364, 1286, 1246, 1178, 1030, 826, 762.

NMR(CDCL): 8.92–8.56(1H,m), 7.78(1H,s), 7.70–6.90(1 1H,m), 3.90(3H,s), 3.50–3.06(2H,br), 2.42(3H, s).

3-Amino-6-methoxy-2-(2-methylphenyl)imidazo[2,1-a] isoquinoline (Compound 24)

m.p.: 162.0–163.0° C.

IR(KBr): 3430, 3120, 2960, 2850, 1650, 1630, 1580, 1521, 1491, 1449, 1383, 1338, 1285, 1259, 1235, 1160, 1120, 1098, 1030, 982, 863, 760, 728.

NMR(CDCL): 8.72–8.45(1H,m), 8.15–7.85(1H,m), 7.71–7.09(7H,m), 3.87(3H,s), 3.78(2H,brs), 2.38(3H,s).

3-Amino-9-methoxy-2-(2-methylphenyl)imidazo[2,1-a] isoquinoline (Compound 26)

m.p.: 131.0–132.0° C.

IR(KBr): 3380, 3125, 3000, 2950, 2840, 1616, 1577, 1546, 1520, 1503, 1458, 1442, 1380, 1292, 1255, 1233, 1205, 1175, 1076, 1033, 870, 803, 752, 720.

NMR(CDCL): 8.00(1H,d,J=3.0 Hz), 7.68(1H,d,J=7.2 Hz), 7.57(1H,d,J=8.0 Hz), 7.60–7.00(5H,m), 6.93(1H,d,J= 7.2 Hz), 3.93(3H,s), 3.28(2H,brs), 2.40(3H,s).

3-Amino-9-isopropoxy-2-(2-methylphenyl)imidazo[2,1-a] isoquinoline (Compound 30)

m.p.: 127.0–128.0° C.

IR(KBr): 3400, 3160, 3000, 2940, 1615, 1578, 1520, 1500, 1459, 1380, 1335, 1290, 1230, 1112,955,825.

NMR(CDCL): 8.06(1H,d,J=2.0 Hz), 7.72(1H,d,J=7.0 Hz), 7.60(1H,d,J=8.0 Hz), 7.50–7.10(5H,m), 6.98(1H,d,J= 7.0 Hz), 4.82(1H,qui,J=6.0 Hz), 3.29(2H,brs), 2.41(3H,s), 1.40(6H,d,J=6.0 Hz).

3-Amino-8,9-dimethoxy-2-(2-methylphenyl)imidazo[2,1-a] isoquinoline (Compound 33)

m.p.: 189.0–192.0° C.(dec.).

IR(KBr): 3400, 3320, 3070, 3020, 2970, 2840, 1620, 1578, 1550, 1520, 1500, 1478, 1443, 1400, 1362,1279, 1245, 1223, 1198, 1160, 1080, 1011, 860, 765,725.

NMR(CDCL): 8.05(1H,s), 7.76(1H,d,J=7.0 Hz), 7.57–7.21(4H,m), 7.05(1H,s), 6.93(1H,d,J=7.0 Hz), 4.05 (3H,s), 3.98(3H,s), 3.25(2H,brs), 2.41(3H,s).

3-Amino-9-ethoxycarbonylmethoxy-2-(2-methylphenyl) imidazo[2,1-a]isoquinoline (Compound 35)

IR(KBr): 3400, 3330, 2980, 1750, 1615, 1575, 1520, 1499, 1440, 1380, 1338, 1275, 1195, 1090, 1060, 1015, 910, 855, 820,750.

NMR(CDCL): 7.93(1H,d,J=2.4 Hz), 7.67(1H,d,J=7.6 Hz), 7.56(1H,d,J=8.4 Hz), 7.48–7.05(5H,m), 6.91(1H,d,J= 7.6 Hz), 4.76(2H,s), 4.25(2H,q,J=7.0 Hz), 3.32(2H,brs), 2.40(3H,s), 1.29(3H,t,J=7.0 Hz).

3-Amino-9-(2-hydroxyethoxy)-2-(2-methylphenyl)imidazo [2,1-a]isoquinoline (Compound 36)

m.p.: 122.0–124.0° C.

IR(KBr): 3420, 3330, 3050, 2950, 2760, 1620, 1583, 1520, 1500, 1458, 1417, 1388, 1340, 1295, 1230, 1080, 1060, 940, 900, 818, 770, 725.

NMR(DMSO): 8.00(1H,d,J=7.0 Hz), 7.85(1H,d,J=2.0 Hz), 7.76(1H,d,J=8.4 Hz), 7.68–7.05(7H,m), 4.99(3H,br), 4.19(2H,t,J=4.6 Hz), 4.00–3.70(2H,m), 2.43(3H,s).

3-Amino-9-(2-methoxyethoxy)-2-(2-methylphenyl)imidazo [2,1-a]isoquinoline (Compound 37)

m.p.: 151.0–152.0° C.

IR(KBr): 3410, 3340, 2925, 1645, 1632, 1617, 1575, 1550, 1500, 1492, 1452, 1378, 1340, 1298, 1275, 1225, 1200, 1122, 1105, 1048, 1023,935, 858, 820,764, 720.

NMR(CDCL): 7.98(1H,d,J=2.0 Hz), 7.65(1H,d,J=7.0 Hz), 7.55(1H,d,J=9.0 Hz), 7.45–7.00(5H,m), 6.90(1H,d,J= 7.0 Hz), 4.39–4.15(2H,m), 3.85–3.65(2H,m), 3.45(3H,s), 3.30(2H,brs), 2.40(3H,s).

3-Amino-6-benzyloxy-2-(2-methylphenyl)imidazo[2,1-a] isoquinoline (Compound 38)

m.p.: 149.0–150.0° C.

IR(KBr): 3470, 3310, 3180, 3090, 2940, 2880, 1651, 1622, 1575, 1520, 1495, 1460,1395,1375,1336, 1300,1285, 1236,1160, 1115,1092,1030,982,912, 880, 760, 730, 692.

NMR(CDCL): 8.75–8.50(1H,m), 8.25–8.00(1H,m), 7.70–7.10(12H,m), 5.12(2H,s), 3.25(2H,brs), 2.40(3H,s)

9-Acetoxy-3-amino-2-(2-methylphenyl)imidazo[2,1-a] isoquinoline (Compound 41)

m.p.: 145.0–146.5° C.

IR(KBr): 3400, 1762, 1612, 1575, 1520, 1495, 1373, 1300, 1272, 1209, 1180, 930, 902, 822, 770.

NMR(CDCL): 8.28(1H,d,J=2.0 Hz), 7.60(1H,d,J=7.0 Hz), 7.52(1H,d,J=8.0 Hz), 7.49–7.08(5H,m), 6.80(1H,d,J=7.0 Hz), 4.17(2H,brs), 2.39(3H,s), 2.30(3H,s).

3-Amino-9-isobutyryloxy-2-(2-methylphenyl)imidazo[2,1-a]isoquinoline (Compound 43)

m.p.: 138.0–140.0° C.

IR(KBr): 3400, 3300, 2960, 2900, 2860, 1737, 1625, 1608, 1550, 1520, 1490, 1470, 1460, 1420, 1385, 1370, 1350, 1300,1273, 1240, 1207, 1180,1155, 1137, 929, 909, 880, 806, 765, 745.

NMR(CDCL): 8.26(1H,d,J=2.0 Hz), 7.64(1H,d,J=7.6 Hz), 8.57(1H,d,J=8.4 Hz), 8.57–7.05(5H,m), 6.86(1H,d,J=7.6 Hz), 3.33(2H,brs), 3.20–2.45(1H,m), 2.40(3H,s), 1.35 (6H,d,J=7.0 Hz).

3-Amino-9-(N,N-dimethylcarbamoyloxy)-2-(2-methylphenyl)imidazo[2,1-a]isoquinoline (Compound 44)

m.p.: 169.0–171.0° C.

IR(KBr): 3420, 3310, 3220, 2990, 2920, 1705, 1642, 1626, 1580, 1568, 1518, 1489, 1440, 1410,1390,1325, 1300, 1270, 1237, 1210,1170,1065, 1018,914, 888, 808, 750.

NMR(CDCL): 8.18(1H,d,J=2.4 Hz), 7.50(1H,d,J=7.0 Hz), 7.53–7.03(6H,m), 6.69(1H,d,J=7.0 Hz), 3.50(2H,brs), 3.08(6H,brs), 2.42(3H,s).

3-Amino-7-benzylthio-2-(2-methylphenyl)imidazo[2,1-a]isoquinoline (Compound 45)

m.p.: 188.0–189.5° C.

IR(KBr): 3380, 3100, 2940, 1640, 1605, 1578, 1548, 1522, 1482, 1458, 1438, 1400, 1380, 1293, 1274, 1230, 1200, 1180, 1157, 1130, 1068,1028, 1000,905, 760,716, 692,.

NMR(CDCL): 8.53(1H,dd,J=2.0 Hz,6.0 Hz), 7.80(1H,d,J=7.0 Hz), 7.63–7.15(12H,m), 4.10(2H,s), 3.30(2H,brs), 2.40(3H,s).

3-Amino-2-(2-methylphenyl)-7-(methylthio)imidazo[2,1-a]isoquinoline (Compound 46)

m.p.: 142.0–144.0° C.

IR(KBr): 3430, 3100, 2950, 1642, 1607, 1483, 1458, 1421, 1380, 1344, 1274, 1256,1203,1165,1138, 1048,962, 898,777.

NMR(CDCL): 8.62(1H,dd,J=3.6 Hz,6.0 Hz), 7.93–7.07 (8H,m), 3.55–3.15(2H,br), 2.93(3H,s), 2.40(3H,s).

6-Acetyl-3-amino-2-(2-methylphenyl)imidazo[2,1-a]isoquinoline (Compound 47)

m.p.: 190.0–191.0° C.

IR(KBr): 3410, 3230, 2960, 1672, 1616, 1595, 1490, 1454, 1408, 1368, 1336, 1324,1289,1185,1160,767.

NMR(DMSO): 9.10–8.75(1H,m), 9.04(1H,s), 8.63–8.31 (1H,m), 7.90–7.09(6H,m), 5.42(2H,brs), 2.79(3H,s), 2.47 (3H,s).

3-Amino-7-(p-anisoyl)-2-(2-methylphenyl)imidazo[2,1-a]isoquinoline (Compound 48)

m.p.: 164.0–165.0° C.

IR(KBr): 3400, 3330, 1650, 1600, 1572, 1514, 1422, 1373, 1312, 1278, 1260, 1175, 1142, 1015,965, 887, 846, 794, 754.

NMR(CDCL): 8.93–8.61(1H,m), 8.02–6.75(12H,m), 3.85(3H,s), 3.46(2H,brs), 2.40(3H,s).

3-Amino-2-(2-methylphenyl)imidazo [2,1-a] isoquinolin-7-carboxylic acid (Compound 49) hydrochloride m.p.: 231.0–233.5° C.

IR(KBr): 3450–3340, 2950–2800, 2720, 2680, 2630, 1710, 1670, 1627, 1548, 1496,1458,1396,1270, 1220,1128, 792.

NMR(DMSO): 9.55–9.25(1H,m), 8.95–8.32(3H,m), 7.98 (1H,t,J=8.0 Hz), 7.50(4H,s), 2.44(3H,s).

3-Amino-6-methoxycarbonyl-2-(2-methylphenyl)imidazo [2,1-a] isoquinoline (Compound 50)

m.p.: 185.0–186.0° C.

IR(KBr): 3410, 3330, 3180, 2960, 1712, 1633, 1607, 1586, 1485, 1455, 1439, 1401, 1330, 1302, 1282, 1244, 1198, 1156, 1045, 1030,928,760.

NMR(CDCL): 8.95–8.52(2H,m), 8.64(1H,s), 7.73–7.05 (6H,m), 3.93(3H,s), 3.40(2H,brs), 2.37(3H,s).

3-Amino-7-cyano-2-(2-methylphenyl)imidazo[2,1-a] isoquinoline (Compound 52)

m.p.: 190.0–191.0° C.

IR(KBr): 3400, 3140, 2250, 1642, 1600, 1576, 1528, 1492, 1450, 1378, 1325, 1275,1218,1150,928,768.

NMR(CDCL): 8.78(1H,dd,J=2.0 Hz,7.0 Hz), 7.99(1H,d, J=7.0 Hz), 7.90–7.01(7H,m), 3.57(2H,brs), 2.44(3H,s).

3-Amino-7-diethylamino-2-(2-methylphenyl)imidazo[2,1-a]isoquinoline (Compound 54)

IR(KBr): 3430, 3320, 3060, 2980, 2940, 2870, 2830, 1640, 1600, 1556, 1486, 1450, 1380, 1250, 1210, 1135, 1030, 945, 780–750.

NMR(CDCL): 8.40(1H,brd,J=7.0 Hz), 7.92–7.10(8H,m), 3.52–2.93(2H,br), 3.19(4H,q,J=7.0 Hz), 2.43(3H,s), 1.05 (6H,t,J=7.0 Hz).

(hydrochloride m.p.:211.0–215.0° C.).

3-Amino-10-chloro-9-methoxy-2-(2-methylphenyl)imidazo [2,1-a]isoquinoline (Compound 55)

m.p.: 180.5–181.5° C.

IR(KBr): 3180, 3010, 2940, 2840, 1648, 1603, 1573, 1538, 1490, 1460, 1440, 1409, 1370, 1280, 1254, 1222, 1180, 1154, 1118, 1067, 1040, 1010,952,855,800, 753, 720.

NMR(CDCL): 7.55(1H,d,J=7.0 Hz), 7.45(1H,d,J=8.0 Hz), 7.40–7.12(4H,m), 7.04(1H,d,J=8.0 Hz), 6.78(1H,d,J=7.0 Hz), 3.95(3H,s), 3.40(2H,brs), 2.50(3H,s).

3-Amino-9-methoxy-5-methyl-2-(2-methylphenyl)imidazo [2,1-a]isoquinoline (Compound 56)

m.p.: 165.0–166.0° C.

IR(KBr): 3400, 3280, 3160, 1675, 1613, 1524, 1495, 1455, 1436, 1390, 1355, 1296, 1240, 1180, 1150, 1098, 1032, 890, 850,765,728.

NMR(CDCL): 8.01(1H,d,J=2.6 Hz), 7.62–7.25(5H,m), 7.09(1H,dd,J=2.6 Hz,9.0 Hz), 6.61(1H,s), 3.94(3H,s), 3.32 (2H,brs), 2.94(3H,s), 2.40(3H,s).

3-Amino-2-(3-methylphenyl)imidazo[2,1-a]isoquinoline (Compound 57) hydrochloride m.p.: 192.0° C.(dec.).

IR(KBr): 3320, 3170, 3060, 2940, 2720, 1662, 1615, 1549, 1496, 1460, 1425, 1335, 794, 685.

NMR(DMSO): 9.42–9.08(1H,m), 8.58(1H,d,J=7.0 Hz), 8.20–7.00(8H,m), 2.38(3H,s).

3-Amino-2-(2-ethylphenyl)imidazo[2,1-a]isoquinoline (Compound 59) hydrochloride m.p.: 215.0–216.0° C.

IR(KBr): 3450, 3120, 2980, 2940, 2890, 2600, 1668, 1630, 1550, 1498, 1460, 1426, 1330, 1281, 1250, 1168, 868, 794,770, 680.

NMR(DMSO): 9.15–8.88(1H,m), 8.65(1H,d,J=7.0 Hz), 8.29–7.70(4H,m), 7.50(4H,s), 2.78(2H,q,J=7.0 Hz), 1.11 (3H,t,J=7.0 Hz).

3-Amino-2-(2-trifluoromethylphenyl)imidazo[2,1-a] isoquinoline (Compound 60) hydrochloride m.p.: 189.0–194.0° C.(dec.).

IR(KBr): 3470, 3270, 3150, 3050, 2920, 2800, 2730, 2680, 1668, 1632, 1608, 1582, 1550, 1500, 1460, 1439, 1425, 1318, 1270, 1241, 1171, 1120, 1059, 1033, 970, 798, 778, 675.

NMR(DMSO): 8.92–8.70(1H,m), 8.55(1H,d,J=7.4 Hz), 8.30–7.60(8H,m).

3-Amino-2-(2,4-dimethylphenyl)imidazo[2,1-a]isoquinoline (Compound 62)

m.p.: 191.0–192.5° C.

IR(KBr): 3100, 2920, 1645, 1615, 1583, 1529, 1505, 1490, 1458, 1380, 1275, 1145, 825, 770.

NMR(CDCL): 8.72–8.50(1H,m), 7.90–6.89(8H,m), 3.28 (2H,brs), 2.34(6H,s).

3-Amino-2-(4-chloro-2-methylphenyl)imidazo[2,1-a]isoquinoline (Compound 66)

m.p.: 223.0–224.0° C.

IR(KBr): 3390, 3250, 3120, 3070, 3040, 2930, 1645, 1615, 1580, 1525, 1487, 1459, 1437, 1415, 1380, 1315, 1284, 1204, 1173, 1145, 1100, 1029, 985, 893, 866, 824, 770, 680.

NMR(DMSO): 8.43–8.19(1H,m), 8.03(1H,d,J=7.0 Hz), 7.87–7.23(6H,m), 7.10(1H,d,J=7.0 Hz), 5.04(2H,brs), 2.41 (3H,s).

3-Amino-2-(4-hydroxy-2-methylphenyl)imidazo[2,1-a]isoquinoline (Compound 68)

m.p.: 273.0–276.0° C.(dec.).

IR(KBr): 3400, 3330, 3050, 3000, 2910, 2770, 2670, 2600, 1638, 1608, 1510, 1500, 1453, 1380, 1300, 1245, 1165, 948, 899, 860, 810, 785, 740.

NMR(DMSO): 9.35(1H,s), 8.50–8.28(1H,m), 8.09(1H,d, J=7.0 Hz), 7.92–7.02(5H,m), 6.82–6.58(2H,m), 4.82(2H, brs), 2.33(3H,s).

3-Amino-2-(4-methoxy-2-methylphenyl)imidazo[2,1-a]isoquinoline (Compound 69) hydrochloride m.p.: 215.5–217.5° C.

IR(KBr): 3380, 3090, 2920, 2830, 2750, 2680, 2600, 1665, 1610, 1567, 1545, 1510, 1460, 1420, 1292, 1245, 1162, 1068, 1038, 790.

NMR(DMSO): 9.28–8.94(1H,m), 8.65(1H,d,J=7.0 Hz), 8.29–7.70(4H,m), 7.48(1H,d,J=9.0 Hz), 7.09–6.80(2H,m), 5.604.55(2H,br), 3.85(3H,s), 2.83(3H,s).

2-(4-Acetoxy-2-methylphenyl)-3-aminoimidazo[2,1-a]isoquinoline (Compound 70) hydrochloride m.p.: 201.0–205.0° C.

IR(KBr): 3600, 3450, 3350, 3150, 2910, 2640, 1750, 1662, 1625, 1547, 1500, 1453, 1420, 1370, 1203, 1158, 1013, 950, 904, 788.

NMR(DMSO): 9.13–8.90(1H,m), 8.61(1H,d,J=7.0 Hz), 8.28–7.50(5H,m), 7.31–7.08(2H,m), 2.40(3H,s), 2.31(3H,s).

3-Amino-2-(2,4,6-trimethylphenyl)imidazo[2,1-a]isoquinoline (Compound 71)

m.p.: 103.0–105.0° C.

IR(KBr): 3420, 3320, 3150, 3070, 3020, 2970, 2930, 2860, 1645, 1615, 1585, 1520, 1485, 1450, 1375, 1311, 1275, 1210, 1139, 1085, 1025, 983, 891, 850,784, 745, 685.

NMR(CDCL): 8.75–8.52(1H,m), 7.83(1H,d,J=7.0 Hz), 7.74–7.32(3H,m), 7.02(1H,d,J=7.0 Hz), 6.95(2H,s), 3.33–2.95(2H,br), 2.31(3H,s), 2.12(6H,s).

3-Amino-2-(3-methyl-2-thienyl)imidazo[2,1-a]isoquinoline (Compound 73)

m.p.: 174.0–175.0° C.

IR(KBr): 3400, 3340, 3100, 3060, 2920, 1640, 1605, 1519, 1482, 1458, 1371, 935, 890, 833, 785, 732, 712, 673.

NMR(CDCL): 8.78–8.52(1H,m), 7.84–7.41(4H,m), 7.29 (1H,d,J=5.0 Hz), 6.99(1H,d,J=7.4 Hz), 6.98(1H,d,J=5.0 Hz), 3.41(2H,brs), 2.44(3H,s).

3-Amino-6-methoxy-2-(3-methyl-2-thienyl)imidazo[2,1-a]isoquinoline (Compound 74)

m.p.: 143.0–146.0° C.

IR(KBr): 3440, 3110, 2950, 1652, 1627, 1590, 1521, 1470, 1450, 1381, 1330, 1298, 1257, 1235, 1161, 1125, 1099, 1028, 995, 960, 924, 861, 762.

NMR(CDCL): 8.70–8.46(1H,m), 8.13–7.91(1H,m), 7.78–7.42(2H,m), 7.27(1H,s), 7.22(1H,d,J=5.0 Hz), 6.93 (1H,d,J=5.0 Hz), 3.92(3H,s), 3.62–3.08(2H,br), 2.45(3H,s).

3-Amino-9-methoxy-2-(3-methyl-2-thienyl)imidazo[2,1-a]isoquinoline (Compound 75)

IR(KBr): 3420, 2930, 1616, 1518, 1500, 1439, 1370, 1337, 1297, 1275, 1229, 1180, 1139, 1026,905, 854,820.

NMR(CDCL): 7.99(1H,d,J=2.4 Hz), 7.64(1H,d,J=7.6 Hz), 7.53(1H,d,J=8.2 Hz), 7.35–7.10(2H,m), 6.96(1H,d,J= 8.2 Hz), 6.94(1H,d,J=6.4 Hz), 3.96(3H,s), 3.55–3.30(2H,br), 2.42(3H,s).

(hydrochloride m.p.: 195.0° C(dec.)).

3-Amino-2-(4-methyl-2-thienyl)imidazo [2,1-a]isoquinoline (Compound 76)

m.p.: 152.0–155.0° C.

IR(KBr): 3460, 3310, 3175, 3070, 2930, 1645, 1623, 1584, 1552, 1520, 1488, 1459, 1375, 1265, 1212, 1182, 1155,922,890,848,788, 720.

NMR(CDCL): 8.75–8.45(1H,m), 7.69(1H,d,J=7.0 Hz), 7.69–7.47(3H,m), 7.33(2H,d,J=1.0 Hz), 6.89(1H,d,J=7.0 Hz), 6.84(1H,d,J=1.0 Hz), 3.53–3.08(2H,br), 2.30(3H,s).

3-Amino-2-(3-ethyl-2-thienyl)imidazo[2,1-a]isoquinoline (Compound 77)

IR(KBr): 3410, 3300, 2970, 2930, 2870, 1642, 1610, 1588, 1519, 1483, 1457, 1370,1324,1272,1210, 1175,1138, 888,780.

NMR(CDCL): 8.68–8.39(1H,m), 7.66(1H,d,J=7.0 Hz), 7.58–7.30(3H,m), 7.22(1H,d,J=5.0 Hz), 6.98(1H,d,J=5.0 Hz), 6.86(1H,d,J=7.0 Hz), 3 .38(2H,brs), 2.83(2H,q,J=7.0 Hz), 1.22(3H,t,J=7.0 Hz).

3-Amino-2-(2-methyl-3-thienyl)imidazo[2,1-a]isoquinoline (Compound 78)

m.p.: 124.0–124.5° C.

IR(KBr): 3400, 3330, 3090, 2910, 1638, 1606, 1518, 1482, 1455, 1440, 1373, 1230, 1209, 1170,1139,1084,890, 858,784,732,690.

NMR(CDCL): 8.75–8.45(1H,m), 7.78(1H,d,J=7.0 Hz), 7.70–7.40(3H,m), 7.23(1H,d,J=5.0 Hz), 7.10(1H,d,J=5.0 Hz), 6.98(1H,d,J=7.0 Hz), 3.30(2H,brs), 2.62(3H,s).

3-Amino-2-(4-methyl-3-thienyl)imidazo[2,1-a]isoquinoline (Compound 81)

m.p.: 155.5–156.0° C.

IR(KBr): 3440, 3300, 3150, 3050, 1640, 1620, 1580, 1548, 1518, 1485, 1455, 1370, 1360, 1262, 1210, 1180, 1 154 , 890 , 848 , 790,720.

NMR(CDCL): 8.72–8.48(1H,m), 7.67–7.44(4H,m), 7.28 (1H,brs), 6.86–6.73(2H,m), 3.30(2H,brs), 2.27(3H,s).

3-Amino-2-(2,5-dimethyl-3-thienyl)imidazo [2,1-a]isoquinoline (Compound 83) hydrochloride m.p.: 233.0° C.(dec.).

IR(KBr): 3350, 3140, 3050, 2910, 2850, 2750, 266, 1665, 1625, 1545, 1440, 1420,1380,1328,1305, 1246,1110,790.

NMR(DMSO): 9.20–8.97(1H,m), 8.62(1H,d,J=7.0 Hz), 8.26–7.68(4H,m), 7.01(1H,s), 2.48(6H,s).

3-Amino-2-(2-chloro-3-methyl-4-thienyl)imidazo[2,1-a]isoquinoline (Compound 85)

m.p.: 167.0–170.0° C.(dec.).

IR(KBr): 3400, 3150,3100, 1640, 1613, 1595, 1520, 1477, 1455, 1369, 1352, 1138,1005,763,680.

NMR(CDCL): 8.71–8.42(1H,m), 7.71(1H,d,J=7.0 Hz), 7.70–7.38(3H,m), 7.13(1H,s), 6.99(1H,d,J=7.0 Hz), 3.42 (2H,br), 2.35(3H,s).

3-Amino-7-bromo-2-(2-chloro-3-methyl-4-thienyl)imidazo[2,1-a]isoquinoline (Compound 86)

IR(KBr): 3420, 3100, 2930, 1638, 1615, 1596, 1513, 1478, 1435, 1400, 1370, 1342, 1257, 1211,1102, 1030,961, 895,858,776, 740.

NMR(CDCL): 8.55(1H,brd,J=7.4 Hz), 7.93–7.62(2H,m), 7.55–7.19(2H,m), 7.15(1H,s), 3.62–3.23(2H,br), 2.29(3H,s).

3-Amino-2-(3-methyl-2-furyl)imidazo[2,1-a]isoquinoline (Compound 88)
m.p.: 183.0–185.0° C.(dec.).
IR(KBr): 3420, 3325, 2925, 1640, 1600, 1545, 1521, 1481, 1458, 1367, 1168, 1078, 885, 795, 746, 725.
NMR(DMSO): 8.53–8.30(1H,m), 8.10(1H,d,J=7.0 Hz), 7.95–7.48(4H,m), 7.18(1H,d,J=7.0 Hz), 6.47(1H,d,J=2.0 Hz), 5.42(2H,brs), 2.46(3H,s).

3-Amino-2-(2,5-dimethyl-3-furyl)imidazo [2,1-a] isoquinoline (Compound 91)
m.p.: 135.0–136.0° C.(dec.).
IR(KBr): 3410, 3310, 2920, 1640, 1594, 1520, 1482, 1452, 1374, 1268, 1212, 1186, 1080, 994, 922, 890, 784, 740.
NMR(CDCL): 8.80–8.54(1H,m), 7.77(1H,d,J=7.0 Hz), 7.70–7.40(3H,m), 6.95(1H,d,J=7.0 Hz), 6.28(1H,s), 3.22(2H,brs), 2.54(3H,s), 2.29(3H,s).

3-Amino-2-(1-methyl-2-pyrrolyl)imidazo [2,1-a] isoquinoline (Compound 94)
m.p.: 134.0–136.0° C.(dec.).
IR(KBr): 3400, 3320, 3090, 1638, 1607, 1585, 1532, 1515, 1492, 1453, 1374, 1313, 1289, 1262, 1177, 1086, 1053, 970, 892, 780, 718, 700.
NMR(CDCL): 8.70–8.35(1H,m), 7.61(1H,d,J=7.0 Hz), 7.58–7.33(3H,m), 6.88(1H,d,J=7.0 Hz), 6.70(1H,t,J=2.0 Hz), 6.34–6.12(2H,m), 3.87(3H,s), 3.44(2H,brs).

3-Amino-2-(2-methylphenyl)-5,6-dihydroimidazo[2,1-a]isoquinoline (Compound 96) maleate
m.p.: 157.0–158.0° C.
IR(KBr): 3350, 3210, 3060, 2960, 2920, 2840, 2800, 2740, 1655, 1585, 1480, 1360, 1210, 1192, 1010–988, 868, 760, 700.
NMR(DMSO): 8.10–7.72(1H,m), 7.67–7.27(7H,m), 6.05(2H,s), 4.23(2H,t,J=7.0 Hz), 3.28(2H,t,J=7.0 Hz), 2.35(3H,s).

3-Amino-9-fluoro-2-(2-methylphenyl)-5,6-dihydroimidazo[2,1-a]isoquinoline (Compound 97)
m.p.: 157.5–158.0° C.
IR(KBr): 3410, 3150, 2920, 1620, 1575, 1538, 1496, 1456, 1356, 1315, 1270, 1258, 1202, 1174, 1070, 911, 876, 862, 799, 766, 722.
NMR(CDCL): 7.75(1H,dd,J=2.0 Hz, 10.0 Hz), 7.50–6.70(6H,m), 3.98(2H,t,J=7.0 Hz), 3.50–2.90(2H,br), 3.09(2H,t,J=7.0 Hz), 2.40(3H,s).

3-Amino-8-chloro-2-(2-methylphenyl)-5,6-dihydroimidazo[2,1-a]isoquinoline (Compound 98) hydrochloride
m.p.: 199.0–201.0° C.(dec.).
IR(KBr): 3425, 3320, 3130, 2930, 2850, 2760, 2700, 2660, 2620, 1640, 1560, 1504, 1480, 1453, 1314, 1290, 1193, 1110, 1084, 850, 823, 764.
NMR(DMSO): 8.42(1H,d,J=8.0 Hz), 7.82–7.27(6H,m), 4.31(2H,t,J=7.0 Hz), 3.31(2H,t,J=7.0 Hz), 2.39(3H,s).

3-Amino-9-bromo-2-(2-methylphenyl)-5,6-dihydroimidazo[2,1-a]isoquinoline (Compound 99)
m.p.: 167.0–170.0° C.
IR(KBr): 3450, 3370, 2960, 2930, 1610, 1588, 1530, 1490, 1460, 1431, 1387, 1347, 1317, 1250, 1224, 1203, 1150, 1100, 1068, 1040, 885, 812, 792, 765, 725.
NMR(CDCL): 8.18(1H,d,J=2.0 Hz), 7.50–6.90(6H,m), 3.98(2H,t,J=7.0 Hz), 3.48–2.88(2H,br), 3.07(2H,t,J=7.0 Hz), 2.40(3H,s).

3-Amino-5-methyl-2-(2-methylphenyl)-5,6-dihydroimidazo[2,1-a]isoquinoline (Compound 100)
IR(KBr): 3400, 3300, 3120, 3050, 2960, 2920, 1605, 1572, 1530, 1485, 1475, 1450, 1412, 1377, 1353, 1265, 1250, 1200, 1150, 1083, 1030, 978, 940, 755, 720.
NMR(CDCL): 8.17–7.88(1H,m), 7.50–7.05(7H,m), 4.80–4.20(1H,m), 3.42(1H,dd,J=6.0 Hz,16.0 Hz), 3.20(2H,br), 2.78(1H,dd,J=1.6 Hz,16.0 Hz), 2.39(3H,s), 1.24(3H,d,J=7.0 Hz).

3-Amino-9-methyl-2-(2-methylphenyl)-5,6-dihydroimidazo[2,1-a]isoquinoline (Compound 102)
m.p.: 141.5–143.0° C.
IR(KBr): 3420, 3300, 3150, 3050, 2900, 1632, 1615, 1602, 1570, 1532, 1490, 1450, 1378, 1350, 1338, 1315, 1270, 1218, 1186, 1095, 1036, 943, 916, 865, 810, 762, 720.
NMR(CDCL): 7.87(1H,brs), 7.50–6.95(6H,m), 3.93(2H,t,J=7.0 Hz), 3.17(2H,brs), 3.04(2H,t,J=7.0 Hz), 2.39(3H,s), 2.32(3H,s).

3-Amino-5,5-dimethyl-2-(2-methylphenyl)-5,6-dihydroimidazo[2,1-a]isoquinoline (Compound 104)
m.p.: 151.0–152.0° C.(dec.).
IR(KBr): 3440, 3280, 3060, 2960, 2925, 2760, 1680, 1602, 1570, 1488, 1470, 1460, 1435, 1370, 1341, 1300, 1282, 1262, 1239, 1189, 1162, 1120, 1100, 983, 955, 815, 760, 723.
NMR(CDCL): 8.20–8.00(1H,m), 8.10–7.80(2H,br), 7.55–7.00(7H,m), 2.93(1H,d,J=16.0 Hz), 2.59(1H,d,J=16.0 Hz), 2.35(3H,s), 1.70(3H,s), 1.65(3H,s).

3-Amino-6,7-dimethyl-2-(2-methylphenyl)-5,6-dihydroimidazo[2,1-a]isoquinoline (Compound 105)
m.p.: 107.0–110.0° C.(dec.).
IR(KBr): 3420, 3300, 3050, 2970, 2940, 2880, 1675, 1617, 1602, 1580, 1490, 1458, 1418, 1380, 1325, 1150, 753.
NMR(CDCL): 8.07–7.72(1H,m), 7.57–6.91(6H,m), 4.05–2.90(5H,m), 2.41(3H,s), 2.35(3H,s), 1.20(3H,d,J=7.0 Hz).

3-Amino-2-(4-hydroxy-2-methylphenyl)-5,6-dihydroimidazo[2,1-a]isoquinoline (Compound 107)
m.p.: 262.0–265.0° C.(dec.).
IR(KBr): 3410, 3330, 3050, 2960, 2760, 2650, 2580, 1605, 1500, 1456, 1419, 1380, 1350, 1300, 1245, 1200, 1188, 1168, 910, 864, 764.
NMR(DMSO): 9.22(1H,s), 7.88–7.62(1H,m), 7.40–7.03(4H,m), 6.80–6.50(2H,m), 4.50(2H,brs), 4.00(2H,t,J=7.0 Hz), 3.09(2H,t,J=7.0 Hz), 2.30(3H,s).

3-Amino-2-(5-bromo-4-hydroxy-2-methylphenyl)-5,6-dihydroimidazo[2,1-a]isoquinoline (Compound 108)
m.p.: 285.0° C.(dec.).
IR(KBr): 3360, 3140, 2920, 1654, 1610, 1560, 1503, 1480, 1455, 1421, 1357, 1298, 1248, 1220, 864, 815, 772.
NMR(DMSO): 9.73(1H,s), 8.11–7.82(1H,m), 7.65–7.10(3H,m), 6.98–6.64(2H,m), 5.88–5.40(2H,br), 4.28(2H,t,J=7.0 Hz), 3.29(2H,t,J=7.0 Hz), 2.22(3H,s).

3-Amino-5-methyl-2-phenylimidazo[1,2-a]thieno[3,2-c]pyridine (Compound 230)
m.p.: 193.0–194.0° C.
IR(KBr): 3370, 3280, 3090, 1620, 1596, 1580, 1560, 1530, 1485, 1442, 1380, 1360, 1285, 1230, 1195, 990, 915, 878, 818, 792, 770, 730, 710, 685.
NMR(DMSO): 8.35–8.00(2H,m), 7.86–7.63(2H,m), 7.62–7.20(3H,m), 7.06(1H,s), 4.58(2H,brs), 3.02(3H,s).

3-Amino-2-(2-hydroxyphenyl)-5-methylimidazo[1,2-a]thieno[3,2-c]pyridine (Compound 231)
m.p.: 199.5–201.0° C.
IR(KBr): 3400, 3320, 1630, 1570, 1538, 1490, 1455, 1410, 1373, 1290, 1250, 1013, 818, 754, 710.
NMR(DMSO): 8.38–8.20(1H,m), 7.78(2H,s), 7.37–6.72(4H,m), 4.83(2H,brs), 3.60–2.92(1H,br), 3.05(3H,s).

3-Amino-2-(2-chlorophenyl)imidazo[1,2-a]thieno[3,2-c]pyridine (Compound 232)
m.p.: 180.0–181.0° C.
IR(KBr): 3330, 3170, 3080, 1626, 1578, 1482, 1432, 1409, 1402, 1352, 1294, 1252, 1268, 1188, 1168, 1150, 1046, 1030, 954, 900, 756, 702.
NMR(CDCL): 7.97(1H,d,J=5.0 Hz), 7.96(1H,d,J=7.0 Hz), 7.87–7.60(1H,m), 7.53(1H,d,J=5.0 Hz), 7.50–7.21(3H,m), 7.21(1H,d,J=7.0 Hz), 3.42(2H,brs).

3-Amino-2-(2-methylphenyl)imidazo[1,2-a]thieno[3,2-c]pyridine (Compound 234)
  m.p.: 136.0–137.0° C.
  Analysis Calcd.for $C_{16}H_{13}N_3S$: C, 68.79%; H, 4.69%; N, 15.04%; Found: C, 68.53%; H, 4.82%; N, 14.75%.
  MS(EI)m/z: 279($M^+$), 263, 150, 135, 83.
  HRMS(EI)m/z: 279.08338(Calcd.for: $C_{16}H_{13}N_3S$; 279.3588).
  IR(KBr): 3350–3200, 3090, 2910, 1628, 1580, 1513, 1490, 1478, 1450, 1410, 1400, 1351, 1294, 1265, 1185, 1168, 1080, 1010,953,765,743,700.
  NMR(CDCL): 7.95(1H,d,J=5.8 Hz), 7.85(1H,d,J=7.0 Hz), 7.49(1H,d,J=5.8 Hz), 7.50–7.10(5H,m), 3.30(2H,brs), 2.39(3H,s).

3-Amino-8-bromo-2-(2-methylphenyl)imidazo[1,2-a]thieno[3,2-c]pyridine (Compound 235)
  m.p.: 221.5–222.0° C.
  IR(KBr): 3360, 3080, 1627, 1605, 1580, 1480, 1450, 1400, 1350, 1290, 1270, 1200, 1170, 1152,980,923,826,763, 726.
  NMR(CDCL): 7.95(1H,s), 7.91(1H,d,J=7.5 Hz), 7.50–7.23(4H,m), 7.10(1H,d,J=7.5 Hz), 3.28(2H,brs), 2.40 (3H,s).

3-Amino-5-methyl-2-(2-methylphenyl)imidazo[1,2-a]thieno[3,2-c]pyridine (Compound 236)
  m.p.: 185.0–185.5° C.
  Analysis Calcd.for $C_{17}H_{15}N_3S$: C, 69.60%; H, 5.15%; N, 14.32%; Found: C, 69.34%; H, 5.20%; N, 14.11%.
  MS(EI)m/z: 293($M^+$), 277, 164, 149, 83.
  HRMS(EI)m/z: 293.09827(Calcd.for: $C_{17}H_{15}N_3S$; 293.3856).
  IR(KBr): 3390, 3280, 3170, 3070, 1632, 1574, 1530, 1488, 1440, 1376, 1286, 1250, 1170, 1012, 882, 810,760, 718,700.
  NMR(CDCL): 7.70(1H,d,J=5.0 Hz), 7.40–7.00(5H,m), 6.62(1H,s), 3.22(2H,brs), 2.87(3H,s), 2.28(3H,s).

3-Amino-5-ethyl-2-(2-methylphenyl)imidazo[1,2-a]thieno[3,2-c]pyridine (Compound 238)
  m.p.: 178.0–179.0° C.
  IR(KBr): 3390, 3330, 3090, 2960, 2940, 2910, 2870, 1630, 1580, 1564, 1534, 1485, 1460, 1434, 1402, 1375, 1289, 1275, 1245, 1176, 1153, 1076, 1000,870, 830, 772, 705.
  NMR(CDCL): 7.80(1H,d,J=5.0 Hz), 7.44–7.03(5H,m), 6.80(1H,s), 3.40(2H,q,J=7.0 Hz), 3.38–3.13(2H,br), 2.32 (3H,s), 1.37(3H,t,J=7.0 Hz).

3-Amino-5,6-dimethyl-2-(2-methylphenyl)imidazo[1,2-a]thieno[3,2-c]pyridine (Compound 239)
  m.p.: 173.5–175.0° C.
  IR(KBr): 3390, 3200, 3060, 2920, 2850, 1625, 1578, 1555, 1519, 1509, 1489, 1465,1452,1435,1395, 1358,1282, 1255,1192, 1085, 1006,880,832,762,712.
  NMR(CDCL): 7.90(1H,d,J=5.5 Hz), 7.60–7.15(4H,m), 7.40(1H,d,J=5.5 Hz), 3.45–3.15(2H,br), 3.00(3H,s), 2.44 (3H,s), 2.38(3H,s).

3-Amino-5-methyl-2-(3-methylphenyl)imidazo[1,2-a]thieno[3,2-c]pyridine (Compound 242)
  m.p.: 165.0–166.0° C.
  IR(KBr): 3420, 3340, 3080, 2910, 1630, 1606, 1530, 1488, 1446, 1410, 1372, 1290, 1254, 1210, 1170, 1096, 1040, 892, 790, 710.
  NMR(CDCL): 7.93(1H,d,J=5.0 Hz), 7.80–7.00(5H,m), 6.72(1H,s), 3.46(2H,brs), 2.93(3H,s), 2.41(3H,s).

3-Amino-5-methyl-2-(2-trifluoromethylphenyl)imidazo[1,2-a]thieno[3,2-c]pyridine (Compound 244)
  m.p.: 194.0–195.0° C.
  IR(KBr): 3380, 3320, 3070, 1630, 1580, 1536, 1490, 1473, 1450, 1440, 1405, 1378, 1312, 1295, 1268,1240, 1190, 1163, 1140, 1100, 1050, 1030, 1010, 990, 968, 880, 818, 770, 700.
  NMR(CDCL): 8.10–7.90(1H,m), 7.98(1H,d,J=5.8 Hz), 7.90–7.50(3H,m), 7.48(1H,d,J=5.8 Hz), 7.08(1H,s), 2.68 (3H,s).

3-Amino-2-(2-methoxyphenyl)-5-methylimidazo[1,2-a]thieno[3,2-c]pyridine (Compound 245)
  m.p.: 135.0–136.0° C.
  IR(KBr): 3410, 3100, 2930, 2830, 1630, 1568, 1532, 1492, 1463, 1456, 1434, 1386, 1372, 1280, 1240, 1178, 1120, 1068, 1016,884,810,752,708.
  NMR(CDCL): 7.85(1H,d,J=5.0 Hz), 7.74(1H,dd,J=2.0 Hz,7.0 Hz), 7.40–6.83(4H,m), 6.70(1H,s), 3.84(3H,s), 3.52 (2H,br), 2.96(3H,s).

3-Amino-2-(4-chloro-2-methylphenyl)-5-methylimidazo[1,2-a]thieno[3,2-c]pyridine (Compound 248)
  m.p.: 206.0–207.0° C.
  IR(KBr): 3370, 3150, 1630, 1579, 1530, 1480, 1410, 1385, 1370, 1245, 1205, 1173, 1090, 1070, 1010, 862, 810,700.
  NMR(CDCL+DMSO): 7.75(1H,d,J=6.0 Hz), 7.42(1H,d, J=6.0 Hz), 7.40(1H,d,J=8.0 Hz), 7.40–7.10(2H,m), 6.85(3H, s), 3.90(2H,brs), 3.05(3H,s), 2.39(3H,s).

3-Amino-5-methyl-2-(2-thienyl)imidazo[1,2-a]thieno[3,2-c]pyridine (Compound 249)
  m.p.: 185.0–186.0° C.
  IR(KBr): 3400, 3050, 1630, 1580, 1528, 1468, 1434, 1402, 1372, 1300, 1256, 1200, 1172, 1080, 1034, 876, 830, 780, 708, 680.
  NMR(DMSO): 7.73(1H,d,J=5.0 Hz), 7.58(1H,d,J=4.0 Hz), 7.48(1H,d,J=5.0 Hz), 7.29(1H,d,J=5.0 Hz), 7.03(1H, dd,J=4.0 Hz,5.0 Hz), 6.81(1H,s), 3.40(2H,brs), 2.95(3H,s).

3-Amino-2-(3-methyl-2-thienyl)imidazo[1,2-a]thieno[3,2-c]pyridine (Compound 250)
  m.p.: 164.5–165.5° C.
  IR(KBr): 3400, 3280, 3060, 1626, 1510, 1472, 1402, 1384, 1342, 1276, 1252, 1190,1168,1148, 1012,980,948, 830,790,716.
  NMR(CDCL): 7.90(1H,d,J=5.0 Hz), 7.78(1H,d,J=7.0 Hz), 7.44(1H,d,J=5.0 Hz), 7.24(1H,d,J=5.0 Hz), 7.10(1H,d, J=7.0 Hz), 6.89(1H,d,J=5.0 Hz), 3.42(2H,brs), 2.38(3H,s).

3-Amino-2-(2-methyl-3-thienyl)imidazo[1,2-a]thieno[3,2-c]pyridine (Compound 254)
  m.p.: 161.0–162.0° C.
  IR(KBr): 3430, 3270, 3100, 1638, 1622, 1604, 1544, 1516, 1492, 1478, 1448, 1410, 1330, 1268, 1198, 1152, 1080,952,860,814,768, 702.
  NMR(CDCL): 7.91(1H,d,J=5.0 Hz), 7.81(1H,d,J=7.0 Hz), 7.47(1H,d,J=5.0 Hz), 7.30–7.05(3H,m), 3.30(2H,brs), 2.58(3H,s).

3-Amino-5-methyl-2-(2-methyl-3-thienyl)imidazo[1,2-a]thieno[3,2-c]pyridine (Compound 255)
  m.p.: 139.0–140.0° C.
  IR(KBr): 3375, 3250, 3160, 3080, 2910, 1630, 1594, 1532, 1510, 1472, 1450, 1438, 1408, 1382, 1308,1250, 1212, 1158, 1000, 880, 816, 696,675.
  NMR(CDCL): 7.88(1H,d,J=5.5 Hz), 7.38(1H,d,J=5.5 Hz), 7.15(2H,s), 6.78(1H,brs), 3.35(2H,brs), 2.97(3H,s), 2.55(3H,s).

3-Amino-2-(2,5-dimethyl-3-thienyl)imidazo[1,2-a]thieno[3,2-c]pyridine (Compound 264)
  m.p.: 142.0–143.0° C.
  IR(KBr): 3375, 3260, 3175, 3075, 2900, 1625, 1540, 1515, 1475, 1435, 1404, 1391,1375,1338,1322, 1246,1192, 1165,1149, 1135,1085,950, 818,765,703.
  NMR(CDCL): 7.95(1H,d,J=5.5 Hz), 7.84(1H,d,J=7.0 Hz), 7.50(1H,d,J=5.5 Hz), 7.15(1H,d,J=7.0 Hz), 6.89(1H, brs), 3.35(2H,brs), 2.53(3H,s), 2.47(3H,s).

3-Amino-2-(1-methyl-2-pyrrolyl)imidazo[1,2-a]thieno[3,2-c]pyridine (Compound 275)

m.p.: 140.0–141.0° C.

IR(KBr): 3380, 3070, 1622, 1490, 1470, 1404, 1342, 1300, 1170, 1148, 1090, 1052, 984, 952, 796, 710.

NMR(CDCL): 7.84(1H,d,J=5.0 Hz), 7.68(1H,d,J=7.0 Hz), 7.41(1H,d,J=5.0 Hz), 7.02(1H,d,J=7.0 Hz), 6.70(1H,t, J=2.0 Hz), 6.37–6.10(2H,m), 3.80(3H,s), 3.49(2H,brs).

3-Amino-2-(2-methylphenyl)furo[3,2-c]imidazo[1,2-a]pyridine (Compound 276)

m.p.: 151.0–152.0° C.(dec.).

IR(KBr): 3400, 3270, 3100, 1638, 1592, 1504, 1490, 1398, 1360, 1268, 1248, 1176, 1130, 1058, 1030, 990, 890, 730.

NMR(CDCL): 7.89(1H,d,J=7.0 Hz), 7.67(1H,d,J=2.0 Hz), 7.56–7.20(5H,m), 7.10(1H,d,J=7.0 Hz), 3.28(2H,brs), 2.40(3H,s).

3-Amino-2-(2-methyl-3-thienyl)furo[3,2-c]imidazo[1,2-a]pyridine (Compound 280)

m.p.: 146.5–147.0° C.

IR(KBr): 3400, 3300, 3190, 3140, 2920, 1640, 1618, 1532, 1507, 1440, 1402, 1332, 1275, 1250, 1193, 1165, 1130, 1059, 892, 859,730.

NMR(CDCL): 7.90(1H,d,J=7.0 Hz), 7.70(1H,d,J=2.0 Hz), 7.32–7.03(4H,m), 3.26(2H,brs), 2.60(3H,s).

3-Amino-2-(2,5-dimethyl-3-furyl)furo[3,2-c]imidazo[1,2-a]pyridine (Compound 288)

m.p.: 145.5–146.0° C.

IR(KBr): 3450, 3420, 3110, 3075, 2920, 1650, 1638, 1597, 1568, 1510, 1445, 1404, 1332, 1279, 1258, 1222, 1210, 1180, 1138, 1118, 1064, 995, 980, 924, 892, 800, 752, 730.

NMR(CDCL): 7.80(1H,d,J=7.0 Hz), 7.60(1H,d,J=2.0 Hz), 7.28–7.14(1H,m), 6.99(1H,d,J=7.0 Hz), 6.25(1H,brs), 3.21(2H,brs), 2.52(3H,s), 2.30(3H,s).

3-Amino-7-methyl-2-(2-methylphenyl)imidazo[1,2-a]pyrrolo[3,2-c]pyridine (Compound 291) hydrochloride m.p.: 219.0° C.(sublimation).

IR(KBr): 3360, 3260, 3110, 3070, 2950, 2860, 2770, 2700, 1665, 1560, 1538, 1495, 1460, 1425, 1380, 1290, 1252, 1212, 1090, 1040, 750.

NMR(DMSO): 8.42(1H,d,J=7.0 Hz), 7.73(1H,d,J=7.0 Hz), 7.95–7.30(4H,m), 7.58(1H,d,J=3.0 Hz), 7.26(1H,d,J=3.0 Hz), 3.98(3H,s), 2.41(3H,s).

3-Amino-7-benzyl-2-(2-methylphenyl)imidazo[1,2-a]pyrrolo[3,2-c]pyridine (Compound 292) hydrochloride m.p.: 225.0° C.(dec.).

IR(KBr): 3360, 3120, 3060, 2650, 1660, 1630, 1490, 1445, 1378, 1340, 1300, 1259, 1210, 815, 760, 740, 695.

NMR(DMSO): 8.42(1H,d,J=7.6 Hz), 7.79(1H,d,J=7.6 Hz), 7.76(1H,d,J=3.0 Hz), 7.60–7.10(10H,m), 5.63(2H,s), 2.40(3H,s).

3-Amino-5-methyl-2-(2-methylphenyl)imidazo[1,2-a]thieno[3,4-c]pyridine (Compound 303)

m.p.: 154.0–154.5° C.

IR(KBr): 3390, 3170, 3100, 3050, 3010, 2960, 2920, 1645, 1610, 1580, 1530, 1488, 1455, 1430, 1403, 1382, 1366, 1310, 1292, 1270, 1220, 1190, 1095, 1038, 960, 858, 835, 825, 770, 750, 730.

NMR(CDCL): 7.98(1H,d,J=3.0 Hz), 7.40–7.00(5H,m), 6.36(1H,s), 3.29(2H,brs), 2.70(3H,s), 2.32(3H,s).

3-Amino-2-(2-methylphenyl)imidazo[1,2-a]thieno[2,3-c]pyridine (Compound 310)

m.p.: 133.5–134.0° C.

Analysis Calcd.for $C_{16}H_{13}N_3S$: C, 68.79%; H, 4.69%; N, 15.04%; Found: C, 68.74%; H, 4.87%; N, 14.79%.

MS(EI)m/z: 279(M$^+$), 263, 150, 135, 83.

HRMS(EI)m/z: 279.08233(Calcd.for: $C_{16}H_{13}N_3S$; 279.3588).

IR(KBr): 3350, 3150, 2920, 1630, 1575, 1510, 1490, 1450, 1412, 1373, 1306, 1262, 940, 850, 762, 726.

NMR(CDCL): 7.78(1H,d,J=7.0 Hz), 7.50–7.00(7H,m), 3.28(2H,brs), 2.37(3H,s).

3-Amino-5-methyl-2-(2-methylphenyl)imidazo[1,2-a]thieno[2,3-c]pyridine (Compound 311)

m.p.: 179.5–180.0° C.

IR(KBr): 3380, 3270, 3180, 1632, 1572, 1532, 1490, 1443, 1427, 1385, 1360, 1338, 1298, 1278, 1247, 1200, 1032, 930, 820, 764.

NMR(CDCL): 7.33–7.03(6H,m), 6.66(1H,s), 3.25(2H,brs), 2.90(3H,s), 2.30(3H,s).

3-Amino-8-methyl-2-(2-methylphenyl)imidazo[1,2-a]thieno[2,3-c]pyridine (Compound 312)

m.p.: 153.0–153.5° C.

IR(KBr): 3330, 3250, 3160, 2900, 1626, 1570, 1516, 1490, 1448, 1422, 1373, 1298, 1262, 1198, 1170,1038,912, 822,760, 720.

NMR(CDCL): 7.83(1H,d,J=7.0 Hz), 7.63–7.20(4H,m), 7.00(1H,d,J=7.0 Hz), 6.96(1H,s), 3.36(2H,brs), 2.60(3H,s), 2.38(3H,s).

3-Amino-2-(2-methylphenyl)furo[2,3-c]imidazo[1,2-a]pyridine (Compound 318)

m.p.: 65.5–67.0° C.

IR(KBr): 3400, 3300, 3120, 1620, 1584, 1532, 1490, 1438, 1388, 1363, 1270, 1250, 1159, 1118, 1002,888,766, 720.

NMR(CDCL): 7.86(1H,d,J=7.0 Hz), 7.70(1H,d,J=2.0 Hz), 7.55–7.20(4H,m), 6.97(1H,d,J=7.0 Hz), 6.80(1H,d,J=2.0 Hz), 3.46(2H,brs), 2.40(3H,s).

3-Amino-2-(2-methylphenyl)-5,6-dihydroimidazo[1,2-a]thieno[2,3-c]pyridine (Compound 323)

IR(KBr): 3400, 3300, 3050, 2920, 1665, 1625, 1560, 1480, 1432, 1380, 1340, 1220, 1178, 1134, 1090, 1040,945, 870,750,720.

NMR(CDCL): 7.40–7.10(5H,m), 6.89(1H,d,J=5.0 Hz), 4.02(2H,t,J=7.0 Hz), 3.30–3.00(2H,br), 3.10(2H,t,J=7.0 Hz), 2.39(3H,s).

EXAMPLE 4

3-Acetylamino-2-(2-methylphenyl)imidazo[2,1-a]isoquinoline (Compound 112)

To a solution of 1.5 g of 3-amino-2-(2-methylphenyl)imidazo[2,1-a]isoquinoline(Compound 3) in 20 ml of ethanol was added 3.0 ml of acetic anhydride. After 1 hour, precipitated crude crystalline was collected by filtration and recrystallized from ethanol to give 1.5 g of the title compound as a white powder.

m.p.: >270.0° C.

IR(KBr): 3090, 2940, 2800, 1690, 1645, 1619, 1598, 1515, 1460, 1405, 1384, 1284, 782.

NMR(DMSO): 8.28–8.08(1H,m), 7.81–7.05(9H,m), 2.47(3H,s), 2.20(3H,s).

EXAMPLE 5

Compounds obtained in the same manner as in Example 4 are collectively shown below.

3-Acetylamino-2-(2-fluorophenyl)imidazo[2,1-a]isoquinoline (Compound III)

IR(KBr): 3160, 3090, 2950, 2800, 1695, 1645, 1629, 1603, 1580, 1515, 1490, 1459, 1410, 1382, 1370, 1319, 1285, 1272, 1224, 1130, 1095,1034, 1007, 954, 932, 900, 850, 810, 785, 748, 700.

NMR(DMSO): 8.70–8.45(1H,m), 8.20–7.05(10H,m), 2.19(3H,s).

3-(3-Chloropropionylamino)-2-(2-methylphenyl)imidazo[2,1-a]isoquinoline (Compound 124)

m.p.: 223.0° C.(sublimation).

IR(KBr): 3150, 3070, 3020, 2940, 2870, 2760, 1690, 1645, 1617, 1596, 1517, 1458, 1438, 1421, 1403, 1380, 1300, 1252, 1215, 980, 928, 900, 770, 718.

NMR(DMSO): 10.25(1H,brs), 8.69–8.42(1H,m), 8.04–7.20(9H,m), 4.00(2H,t,J=7.0 Hz), 3.00(2H,t,J=7.0 Hz), 2.46(3H,s).

2-(2-Methylphenyl)-3-[3-(methylthio)propionylamino]imidazo[2,1-a]isoquinoline (Compound 125).

m.p.: 219.0–220.0° C.

IR(KBr): 3090, 2940, 1699, 1643, 1619, 1595, 1515, 1490, 1459, 1425, 1400, 1381,1286,1244, 1230,1140,900, 775,726.

NMR(DMSO): 10.2(1H,brs), 8.69–8.40(1H,m), 8.14–7.11(9H,m), 2.80(4H,s), 2.43(3H,s), 2.12(3H,s).

3-[(3-Carboxypropionyl)amino]-2-(2,4-dimethylphenyl)imidazo[2,1-a]isoquinoline (Compound 127)

IR(KBr): 3210, 2940, 1750, 1660, 1602, 1516, 1459, 1382, 1260, 1240, 1165, 990, 955, 900, 817, 780.

NMR(DMSO): 12.9–11.7(1H,br), 10.1(1H,brs), 8.65–8.33(1H,m), 8.04–6.90(8H,m), 2.65(4H,s), 2.38(3H,s), 2.32(3H,s).

3-Hexanoylamino-2-(2-methylphenyl)imidazo[2,1-a]isoquinoline (Compound 128)

IR(KBr): 3150, 3080, 2940, 2870, 1698, 1643, 1618, 1597, 1514, 1490, 1458, 1402, 1380, 1312, 1288, 1247, 1180, 1105, 960, 898,773,722.

NMR(DMSO): 9.90(1H,s), 8.70–8.43(1H,m), 8.05–7.15 (9H,m), 2.40(3H,s), 1.95–0.70(1 1H,m).

3-(Methoxyfumaroylamino)-2-(2-methylphenyl)imidazo[2,1-a]isoquinoline (Compound 129)

m.p.: 254.0–256.0° C.(dec.).

IR(KBr): 3140, 3080, 2960, 2800, 1735, 1691, 1640, 1617, 1598, 1515, 1458, 1400, 1380, 1328,1310, 1202–1185, 1163,990,778,755.

NMR(DMSO): 10.65(1H,s), 8.61–8.39(1H,m), 8.00–7.15 (10H,m), 6.77(1H,d,J=16.0 Hz), 3.77(3H,s), 2.39(3H,s).

3-(p-Anisoylamino)-2-(2-methylphenyl)imidazo[2,1-a]isoquinoline (Compound 131)

m.p.: >270.0° C.

IR(KBr): 3075, 2950, 2860, 1664, 1610, 1590, 1520, 1498, 1460, 1382, 1318, 1287, 1257, 1180,1030,845,780, 725.

NMR(DMSO): 10.37(1H,brs), 8.66–8.37(1H,m), 8.17–6.90(13H,m), 3.85(3H,s), 2.44(3H,s).

2-(2-Methylphenyl)-3-(2-thenoylamino)imidazo[2,1-a]isoquinoline (Compound 132)

m.p.: >270.0° C.

IR(KBr): 3080, 2925, 1660, 1615, 1592, 1525, 1490, 1460, 1422, 1400, 1383, 13 59,1290,1100,788,720.

NMR(DMSO): 10.6(1H,brs), 8.70–8.40(1H,m), 8.16–7.10(12H,m), 2.46(3H,s).

3-[(3-Methyl-2-benz[b]furoyl)amino]-2-(2-methylphenyl)imidazo[2,1-a]isoquinoline (Compound 133)

m.p.: >280.0° C.

IR(KBr): 3230, 3150, 3070, 2940, 1673, 1609, 1590, 1500, 1453, 1420, 1400, 1380, 1315,1294,1268, 1190,1145, 1095,910,833,768.

NMR(DMSO): 10.73(1H,brs), 8.36–8.10(1H,m), 7.91–7.08(13H,m), 2.67(3H,s), 2.54(3H,s).

3-Ethoxycarbonylamino-2-(2-methylphenyl)imidazo[1,2-a]thieno[3,2-c]pyridine (Compound 355)

m.p.: 204.0° C.(sublimation).

IR(KBr): 3080, 2970, 2900, 1722, 1629, 1618, 1594, 1475, 1409, 1390, 1349, 1299, 1241, 1210, 1182, 1095, 1060, 1010,957,760,708.

NMR(CDCL): 7.92(1H,d,J=5.4 Hz), 7.68(1H,d,J=6.6 Hz), 7.50(1H,d,J=5.4 Hz), 7.40–7.00(6H,m), 4.18(2H,q,J= 7.0 Hz), 2.30(3H,s), 1.21(3H,t,J=7.0 Hz).

EXAMPLE 6

3-(N-Acetyl-N-propylamino)-2-(2-methylphenyl)imidazo[2,1-a]isoquinoline (Compound 138) hydrochloride A solution of 6.0 g of 3-acetylamino-2-(2-methylphenyl)imidazo[2,1-a]isoquinoline(Compound 112) in 250 ml of dry N,N-dimethylformamide was added dropwise to a solution of 0.9 g of sodium hydride in oil (prewashed with hexane) in 50 ml of dry N,N-dimethylformamide over 30 minutes under dry argon atmosphere at room temperature. After the mixture was stirred for further 1 hour, 2.2 ml of propyl bromide was added dropwise. When addition was complete, the mixture was stirred at room temperature for 2 hours. The reaction mixture was poured into water and extracted with ethyl acetate. The extract was washed with water and saturated saline, and dried over anhydrous magnesium sulfate. The drying agent was removed by filtration, and the solvent was removed under reduced pressure. The residue was purified by column chromatography on silica gel to give 11.0 g of 3-(N-acetyl-N-propylamino)-2-(2-methylphenyl)imidazo[2,1-a]isoquinoline (Compound 138) as a brown viscous material. To a solution of 3.0 g of the product in 100 ml of ether was added a saturated solution of hydrogen chloride in ether, and precipitated crystalline was collected by filtration. Recrystallization from ether/chloroform gave 2.7 g of the title compound as a white powder.

m.p.: 174.5–177.0° C.

Analysis Calcd.for $C_{23}H_{23}N_3 \cdot HCl \cdot 0.3H_2O$: C, 69.18%; H, 6.21%; N, 10.52%; Found: C, 69.30%; H, 6.08%; N, 10.54%.

IR(KBr): 3075, 3040, 2980, 2940, 2890, 2500, 2260, 1683, 1630, 1543, 1498, 1460, 1430, 1397, 1332, 1300, 1243, 1148,810,750.

NMR(DMSO): 9.48–9.10(1H,m), 8.50(1H,d,J=8.0 Hz), 8.36–7.78(4H,m), 7.60–7.30(4H,m), 3.80–3.10(2H,m), 2.45 (3H,s), 2.38,2.00(3H,each s), 1.62–1.02(2H,m), 0.65(3H,t, J=7.0 Hz).

MS(EI)m/z: 357(M−HCl)$^+$, 314, 272, 245, 128.

EXAMPLE 7

Compounds obtained in the same manner as in Example 6 are collectively shown below.

3-[N-Acetyl-N-(ethoxycarbonylmethyl)amino]-2-(2-methylphenyl)imidazo[2,1-a]isoquinoline (Compound 134)

m.p.: 127.0–128.0° C.

IR(KBr): 3070, 3000, 2950, 2875, 1752, 1692, 1640, 1610, 1585, 1565, 1520, 1490,1458,1401,1379, 1335,1269, 1238,1205, 1165,1140,1094, 1030,980, 895, 800, 769, 729, 705.

NMR(CDCL): 8.80–8.60(1H,m), 8.41(1H,d,J=7.0 Hz), 7.80–7.50(3H,m), 7.40–7.10(5H,m), 4.81(1H,d,J=17.0 Hz), 4.19(2H,q,J=7.0 Hz), 3.52(1H,d,J=17.0 Hz), 2.40(3H,s), 1.95(3H,s), 1.25(3H,t,J=7.0 Hz).

3-[N-Acetyl-N-(N,N-diethylcarbamoylmethyl)amino]-2-(3-ethyl-2-thienyl)imidazo[2,1-a]isoquinoline (Compound 135)

IR(Neat): 3080, 2980, 2940, 2880, 1690, 1656, 1610, 1582, 1520, 1480, 1452, 1371, 1330, 1260, 1238, 1215, 1144, 1072, 1031, 980, 950, 908, 800–780, 740.

NMR(CDCL): 8.92(1H,d,J=7.0 Hz), 8.86–8.60(1H,m), 7.87–7.51(3H,m), 7.33–7.00(3H,m), 5.21(1H,d,J=16.0 Hz), 3.58(1H,d,J=16.0 Hz), 3.57–3.00(6H,m), 1.93(3H,s), 1.48–0.98(9H,m).

3-[N-Acetyl-N-(2-methoxyethyl)amino]-2-(2-methylphenyl)imidazo[2,1-a]isoquinoline (Compound 136) hydrochloride m.p.: 104.0–107.0° C.

IR(KBr): 3100–3000, 2950–2800, 2750–2300, 1684, 1665, 1629, 1545, 1498, 1455, 1429, 1400, 1385, 1338, 1272, 1245, 1235, 1196, 1120, 1100, 1008, 805–740.

NMR(CDCL): 10.00–9.65(1H,m), 8.25–7.60(5H,m), 7.50–7.20(4H,m), 4.60–2.80(4H,m), 3.11(3H,s), 2.55, 2.40 (3H,each s), 2.48, 2.00(3H,each s).

3-(N-Acetyl-N-propylamino)-2-(2-fluorophenyl)imidazo[2,1-a]isoquinoline (Compound 137)

IR(KBr): 3080, 2960, 2870, 1680, 1636, 1610, 1570, 1523, 1452, 1380, 1348, 1300, 1254, 1220, 1150, 800, 760, 740.

NMR(CDCL): 8.90–8.60(1H,m), 8.10–6.90(9H,m), 4.20–2.85(2H,m), 1.98(3H,s), 1.80–1.10(2H,m), 0.78(3H,t, J=7.0 Hz).

3-(N-Acetyl-N-propylamino)-9-methoxy-2-(2-methylphenyl)imidazo[2,1-a]isoquinoline (Compound 141)

IR(KBr): 3070, 2960, 2940, 2880, 1680, 1635, 1618, 1518, 1500, 1440, 1380, 1340, 1290, 1230, 1140, 1028,824.

NMR(CDCL): 8.13(1H,d,J=3.0 Hz), 7.70(1H,d,J=8.0 Hz), 7.63(1H,d,J=7.0 Hz), 7.43–7.07(6H,m), 4.11–2.90(2H, m), 4.00(3H,s), 2.46(3H,s), 1.98(3H,s), 1.78–1.10(2H,m), 0.78(3H,t,J=7.0 Hz).

3-(N-Acetyl-N-propylamino)-2-(3-methylphenyl)imidazo[2,1-a]isoquinoline (Compound 143)

IR(KBr): 3070, 2980, 2930, 2880, 1670, 1640, 1612, 1570, 1522, 1486, 1458, 1420, 1396, 1375, 1349, 1295, 1256, 1240, 1215, 1155, 1072, 1035,977,798, 749, 728, 702.

NMR(CDCL): 8.92–8.67(1H,m), 8.00–7.00(9H,m), 4.25–3.18(2H,m), 2.42(3H,s), 1.90–1.22(2H,m), 1.89(3H,s), 0.83(3H,t,J=7.0 Hz).

3-(N-Acetyl-N-propylamino)-2-(3-methyl-2-thienyl)imidazo[2,1-a]isoquinoline (Compound 144)

IR(Neat): 3070, 3010, 2960, 2940, 2880, 1678, 1640, 1610, 1584, 1520, 1482, 1456,1441,1370,1335, 1298,1260, 1240,1218, 1150,1070,1030,960,934, 890, 832, 790, 748.

NMR(CDCL): 8.90–8.60(1H,m), 7.84–7.54(4H,m), 7.35–7.19(2H,m), 7.00(1H,d,J=5.0 Hz), 4.29–3.79(1H,m), 3.59–3.09(1H,m), 2.71(3H,s), 1.90(3H,s), 1.78–1.10(2H,m), 0.83(3H,t,J=7.0 Hz).

3-(N-Acetyl-N-isopropylamino)-2-(2-methylphenyl)imidazo[2,1-a]isoquinoline (Compound 145)

IR(KBr): 3080, 2990, 2950, 2890, 1670, 1640, 1612, 1588, 1568, 1518, 1485, 1456, 1370, 1330, 1310, 1238, 1212, 1176, 1132, 1118, 1102, 1088, 1040, 956, 925, 892, 796, 782, 740.

NMR(CDCL): 8.92–8.58(1H,m), 7.88–7.02(9H,m), 5.10–4.56(1H,m), 2.52(3H,s), 2.00(3H,s), 0.93(3H,d,J=7.0 Hz), 0.69(3H,d,J=7.0 Hz).

3-(N-Acetyl-N-allylamino)-2-(2-methylphenyl)imidazo[2,1-a]isoquinoline (Compound 146)

IR(Neat): 3080, 3030, 2950, 1675, 1640, 1612, 1590, 1570, 1520, 1485, 1456, 1372, 1326, 1240, 1142, 1100, 1046, 980, 928, 896, 740.

NMR(CDCL): 8.83–8.53(1H,m), 7.88–7.46(4H,m), 7.39–7.02(5H,m), 6.10–5.40(1H,m), 5.204.74(2H,m), 4.744.40(1H,m), 3.93–3.55(1H,m), 2.45(3H,s), 1.94(3H,s).

3-(N-Acetyl-N-isopentylamino)-2-(2-ethylphenyl)imidazo[2,1-a]isoquinoline (Compound 148)

IR(Neat): 3090, 2980, 2950, 2890, 1680, 1641, 1612, 1588 , 1568 , 1520, 1490, 1458, 1378, 1345, 1295, 1270, 1250, 1233, 1210, 1155, 1100, 1070, 1031, 981, 893, 790, 750, 700.

NMR(CDCL): 8.88–8.62(1H,m), 7.88–7.50(4H,m), 7.40–7.13(5H,m), 4.19–3.70(1H,m), 3.48–2.68(3H,m), 2.00 (3H,s), 1.60–1.00(3H,m), 1.26(3H,t,J=7.0 Hz), 0.80(3H,d, J=6.0 Hz), 0.72(3H,d,J=6.0 Hz).

3-[N-Acetyl-N-(4-methylbenzyl)amino]-2-(2-methylphenyl)imidazo[2,1-a]isoquinoline (Compound 151)

IR(KBr): 3070, 3030, 2940, 1680, 1640, 1612, 1587, 1565, 1519, 1486, 1458, 1376, 1333, 1318, 1290, 1250, 1230, 1190, 1100, 1035, 970, 892,790, 730.

NMR(CDCL): 8.90–8.60(1H,m), 7.85–7.55(3H,m), 7.45–6.80(10H,m), 5.32(1H,d,J=13.0 Hz), 4.10(1H,d,J=13.0 Hz), 2.34(3H,s), 2.22(3H,s), 1.95(3H,s).

(hydrochloride m.p.: 126.0–128.0° C.).

3-[N-Ethyl-N-[3-(methylthio)propionyl]amino]-2-(2-methylphenyl)imidazo[2,1-a]isoquinoline (Compound 152)

IR(Neat): 3080, 2990, 2940, 1678, 1640, 1612, 1588, 1568, 1520, 1488, 1458, 1377, 1350, 1258, 1217, 1150, 1128, 1000, 1045, 1022, 980, 930, 893,790, 750–730, 700.

NMR(CDCL): 8.87–8.55(1H,m), 7.89–7.49(4H,m), 7.37–7.02(5H,m), 4.23–3.18(2H,m), 2.98–2.62(2H,m), 2.57–2.17(2H,m), 2.48(3H,s), 1.94(3H,s), 1.05(3H,t,J=7.0 Hz).

2-(2,4-Dimethylphenyl)-3-succinylaminoimidazo[2,1-a]isoquinoline (Compound 154)

m.p.: 233.0–233.5° C.

IR(KBr): 2940, 1728, 1645, 1623, 1600, 1520, 1460, 1427, 1380, 1330, 1169, 780.

NMR(CDCL): 8.83–8.53(1H,m), 7.72–6.84(8H,m), 2.81 (4H,s), 2.36(3H,s), 2.32(3H,s).

EXAMPLE 8

3-(N-Ethyl-N-propylamino)-2-(2-methylphenyl)imidazo[2,1-a]isoquinoline (Compound 207) hydrochloride A solution of 4.0 g of 3-(N-acetyl-N-propylamino)-2-(2-methylphenyl)imidazo[2,1-a]isoquinoline(Compound 138) in 30 ml of dry tetrahydrofuran was added dropwise to a solution of 0.7 g of lithium aluminum hydride in 20 ml of dry tetrahydrofuran over a period of 30 minutes. The mixture was stirred at room temperature for 4 hours. After excessive lithium aluminum hydride was decomposed by the addition of hydrous ether, the mixture was dried over anhydrous magnesium sulfate. The drying agent was removed by filtration, and the solvent was removed under reduced pressure. The residue was purified by column chromatography on silica gel to give 3.5 g of 3-(N-ethyl-N-propylamino)-2-(2-methylphenyl)imidazo[2,1-a] isoquinoline(Compound 207) as a yellow oily material. To a solution of 3.5 g of the product in 100 ml of ether was added a saturated solution of hydrogen chloride in ether, and precipitated crystalline was collected by filtration. Recrystallization from ether/chloroform gave 3.0 g of the title compound as a white powder.

m.p.: 168.5–172.5° C.

Analysis Calcd.for $C_{23}H_{25}N_3 \cdot HCl \cdot 0.2H_2O$: C, 72.03%; H, 6.94%; N, 10.96%; Found: C, 72.04%; H, 6.88%; N, 10.93%.

IR(KBr): 3050, 2980, 2950, 2880, 2540, 1655, 1620, 1545, 1500, 1460, 1420, 1388, 1328, 1283, 1236, 1096, 808, 750.

NMR(DMSO): 9.55–9.22(1H,m), 8.70–7.85(5H,m), 7.70–7.37(4H,m), 3.09(2H,q,J=7.0 Hz), 2.92(2H,t,J=7.0 Hz), 2.43(3H,s), 1.68–0.93(2H,m), 1.10(3H,t,J=7.0 Hz), 0.80(3H,t,J=7.0 Hz).

MS(EI)m/z: 343(M−HCl)$^+$, 314, 300, 245, 128.

EXAMPLE 9

2-(2-Methylphenyl)-3-[(1-phenylethyl)amino]imidazo[2,1-a]isoquinoline (Compound 192)

A solution of 5.0 g of 3-amino-2-(2-methylphenyl)imidazo[2,1-a]isoquinoline (Compound 3) in 30 ml of dry N,N-dimethylformamide was added dropwise to a solution of 1.2 g of sodium hydride in oil (prewashed with hexane) in 10 ml of dry N,N-dimethylformamide over 30 minutes under dry argon atmosphere at room temperature. After the mixture was stirred for further 1 hour, a solution of 4.1 g of (1-bromoethyl)benzene in 30 ml of dry N,N-dimethylformamide was added dropwise. When addition was complete, the mixture was stirred at room temperature for 1 hour. The solution was poured into water and extracted with ethyl acetate. The extract was washed with water and saturated saline, and dried over anhydrous magnesium sulfate. The drying agent was removed by filtration, and the solvent was removed under reduced pressure. The residue was purified by column chromatography on silica gel, and recrystallized from benzene/hexane to give 5.3 g of the title compound as colorless needles.

m.p.: 160.5–161.5° C.

IR(KBr): 3350, 3060, 3020, 2960, 2920, 1608, 1580, 1558, 1517, 1480, 1455, 1390,1368,1264,1230, 1210,1183, 1156,1125,1090,1078, 1008,800,748,720, 690.

NMR(CDCL): 8.76–8.55(1H,m), 7.95(1H,d,J=7.5 Hz), 7.67–7.09(12H,m), 6.99(1H,d,J=7.5 Hz), 4.30–3.85(1H,m), 3.48–3.15(1H,m), 2.28(3H,s), 1.28(3H,d,J=6.5 Hz).

EXAMPLE 10

A solution of 3.0 g of 3-amino-2-(2-methylphenyl) imidazo[2,1-a]isoquinoline (Compound 3) in 30 ml of dry N,N-dimethylformamide was added dropwise to a solution of 0.9 g of sodium hydride in oil (prewashed with hex ane) in 50 ml of dry N,N-dimethylformamide over 30 minutes under dry argon atmosphere at room temperature. After the mixture was stiffed for further 1 hour, 10 ml of allyl bromide was added dropwise. The mixture was stiffed at room temperature for 2 hours, and then at 50° C. for 16 hours. The solution was poured into water, and extracted with ethyl acetate. The extract was washed with water and saturated saline, and dried over anhydrous magnesium sulfate. The drying agent was removed by filtration, and the solvent was removed under reduced pressure. The residue was purified by column, chromatography on silica gel to give 1.5 g of 3-diallylamino-2-(2-methylphenyl)imidazo[2,1-a] isoquinoline(Compound 223) as a brown oily material. The chromatography successively gave 0.5 g of 3-allylamino-2-(2-methylphenyl)imidazo[2,1-a]isoquinoline(Compound 221) as a brown oily material.

Physico-chemical data of 3-diallylamino-2-(2-methylphenyl)imidazo[2,1-a]isoquinoline(Compound 223) is shown below.

IR(Neat): 3090, 3030, 3000, 2940, 2850, 1645, 1611, 1583, 1560, 1520, 1482, 1458, 1420, 1375, 1342, 1230, 1189, 1158, 1091, 990, 921, 790, 750–730, 700.

NMR(CDCL): 8.84–8.55(1H,m), 8.00(1H,d,J-7.0 Hz), 7.83–7.20(7H,m), 7.02(11H,d,J=7.0 Hz), 6.20–5.44(2H,m), 5.27–4.83(4H,m), 3.55(4H,d,J=5.0 Hz), 2.33(3H,s).

(hydrochloride m.p.: 167.0–168.0° C.).

Physico-chemical data of 3-allylamino-2-(2-methylphenyl)imidazo[2,1-a]isoquinoline(Compound 221) is shown below.

IR(Neat): 3250, 3075, 2990, 2940, 2860, 1643, 1610, 1585, 1519, 1482, 1458, 1419, 1373, 1330, 1244, 1186, 1140, 1093, 1045, 990, 920, 896, 789, 750–730.

NMR(CDCL): 8.75–8.46(1H,m), 7.86(1H,d,J=7.0 Hz), 7.68–7.13(7H,m), 6.97(1H,d,J=7.0 Hz), 6.17–5.39(1H,m), 5.28–4.83(2H,m), 3.48(2H,d,J=5.0 Hz), 3.43–2.98(1H,brs), 2.40(3H,s).

(hydrochloride m.p.: 195.0–198.0° C.(dec.)).

EXAMPLE 11

Example 10 was repeated except that N,N-diethylchloroacetamide was used in place of allyl bromide, which gave 3-(N,N-diethylcarbamoyl methyl)amino-2-(2-methylphenyl)imidazo[2,1-a]isoquinoline (Compound 157) as a brown oily material and 3-[bis(N,N-diethylcarbamoylmethyl)amino]-2-(2-methylphenyl) imidazo[2,1-a]isoquinoline (Compound 198) as a brown oily material. To a solution of 1.6 g of the former compound in 50 ml of ether was added a saturated solution of hydrogen chloride in ether, and precipitated crystalline was collected by filtration. Recrystallization from ethyl acetate/chloroform gave 1.0 g of 3-(N,N-diethylcarbamoylmethyl)amino-2-(2-methylphenyl)imidazo[2,1-a]isoquinoline (Compound 157) hydrochloride as a yellow ocher powder.

Physico-chemical data of 3-(N,N-diethylcarbamoylmethyl)amino-2-(2-methylphenyl)imidazo [2,1-a]isoquinoline (Compound 157) hydrochloride is shown below.

m.p.: 187.0–190.0° C.

IR(KBr): 3240, 2990, 2950, 2550, 1659, 1570, 1550, 1490, 1462, 1388, 1340, 1310, 1270, 1223, 1138, 1100,895, 800,754.

NMR(DMSO): 9.20–8.85(1H,m), 8.78(1H,d,J=7.0 Hz), 8.22–7.63(4H,m), 7.55–7.18(4H,m), 3.70(2H,s), 3.32–2.67 (4H,m), 2.32(3H,s), 0.91(3H,t,J=7.0 Hz), 0.73(3H,t,J=7.0 Hz).

Physico-chemical data of 3-[bis(N,N-diethylcarbamoylmethyl)amino]-2 -(2-methylphenyl) imidazo[2,1-a]isoquinoline (Compound 198) is shown below.

IR(Neat): 3080, 2990, 2950, 1658, 1640, 1565, 1519, 1456, 1380, 1310, 1262, 1220,1190,1132,1098, 1048,980, 945,897,740.

NMR(CDCL): 8.72–8.51(1H,m), 8.66(1H,d,J=7.0 Hz), 7.82–7.17(7H,m), 7.06(1H,d,J=7.0 Hz), 3.93(4H,s), 3.52–2.94(8H,m), 2.32(3H,s), 1.06(12H,t,J=7.0 Hz).

EXAMPLE 12

Example 10 was repeated except that 3-amino-7-chloro-2-(2-methylphenyl)imidazo[2,1-a]isoquinoline (Compound 5) and ethyl iodide were used in place of 3-amino-2-(2-methylphenyl)imidazo[2,1-a]isoquinoline and allyl bromide, which gave 7-chloro-3-ethylamino-2-(2-methylphenyl)imidazo[2,1-a]isoquinoline (Compound 159) as yellow needles and 7-chloro-3-diethylamino-2-(2-methylphenyl)imidazo[2,1-a]isoquinoline (Compound 199) as colorless needles.

Physico-chemical data of 7-chloro-3-diethylamino-2-(2-methylphenyl)imidazo[2,1-a]isoquinoline (Compound 199) is shown below.

m.p.: 102.0–102.5° C.

IR(KBr): 2980, 2860, 1600, 1558, 1512, 1490, 1474, 1450, 1370, 1342, 1218, 1088, 900, 788.

NMR(CDCL): 8.64(1H,dd,J=3.0 Hz,7.0 Hz), 8.19(1H,d, J=7.0 Hz), 7.72–7.18(7H,m), 2.97(4H,q,J=7.0 Hz),2.32(3H, s), 1.00(6H,t,J=7.0 Hz.).

Physico-chemical data of 7-chloro-3-ethylamino-2-(2-methylphenyl)imidazo[2,1-a]isoquinoline (Compound 159) is shown below.

m.p.: 157.0–158.0° C.

IR(KBr): 3270, 2980, 2940, 1638, 1600, 1578, 1505, 1472, 1440, 1405, 1370, 1353, 1300, 1260, 1210, 1190, 1160, 1120, 1083, 996, 900, 820,772,740, 720.

NMR(CDCL): 8.60(1H,dd,J=2.0 Hz,7.0 Hz), 8.00(1H,d, J=7.0 Hz), 7.67–7.19(7H,m), 3.27–2.98(1H,br), 2.98(2H,q, J=7.0 Hz), 2.40(3H,s), 1.07(3H,t,J=7.0 Hz).

EXAMPLE 13

Example 10 was repeated except that 3-amino-7-methoxycarbonyl-2-(2-methylphenyl)imidazo[2,1-a] isoquinoline (Compound 51) and methyl iodide were used in place of 3-amino-2-(2-methylphenyl)imidazo[2,1-a] isoquinoline and allyl bromide, which gave 3-dimethylamino-7-methoxycarbonyl-2-(2-methylphenyl) imidazo[2,1-a]isoquinoline (Compound 197) as a pale yellow powder.

m.p.: 130.0–130.5° C.

IR(KBr): 2950, 2880, 2800, 1713, 1636, 1600, 1560, 1492, 1428, 1370, 1307, 1259,1200,1110, 1012,970,926, 800.

NMR(CDCL): 8.92(1H,dd,J=2.0 Hz,7.0 Hz), 8.30(1H,d, J=8.0 Hz), 8.20(1H,dd,J=2.0 Hz,8.0 Hz), 7.98(1H,d,J=8.0 Hz), 7.57(1H,t,J=8.0 Hz), 7.30(4H,s), 4.00(3H,s), 2.72(6H, s), 2.37(3H,s).

EXAMPLE 14

2-(2-Methylphenyl)-3-piperidinoimidazo[2,1-a] isoquinoline (Compound 217) hydrochloride To a solution of 3.0 g of 3-amino-2-(2-methylphenyl) imidazo[2,1-a]isoquinoline(Compound 3) in 50 ml of dry N,N-dimethylformamide was added successively 4.6 g of potassium carbonate and 1.6 ml of 1,5-dibromopentane, and the mixture was stirred at 140° C. for 3 hours. After being cooled, the mixture was poured into water and extracted with ethyl acetate. The extract was washed with water and saturated saline, and dried over anhydrous magnesium sulfate. The drying agent was removed by filtration, and the solvent was removed under reduced pressure. The residue was purified by column chromatography on silica gel to give 3.7 g of 2-(2-methylphenyl)-3-piperidinoimidazo[2,1-a] isoquinoline (Compound 217) as a brown oily material. To a solution of 2.0 g of the product in 80 ml of ether was added a saturated solution of hydrogen chloride in ether, and precipitated crystalline was collected by filtration. Recrystallization from ethyl acetate/petroleum ether gave 1.4 g of the title compound as a white powder.

m.p.: 212.0–215.0° C.

Analysis Calcd.for $C_{23}H_{23}N_3 \cdot HCl \cdot 0.5H_2O$: C, 71.40%; H, 6.51%; N, 10.86%; Found: C, 71.44%; H, 6.45%; N, 10.94%.

IR(KBr): 2950, 2850, 2620, 1660, 1622, 1548, 1498, 1450, 1382, 1283, 1130, 905, 800, 752.

NMR(DMSO): 9.40–9.07(1H,m), 8.45(1H,d,J=7.0 Hz), 8.35–7.83(4H,m), 7.70–7.37(4H,m), 3.15–2.70(4H,m), 2.40 (3H,s), 1.98–1.30(6H,m).

MS(EI)m/z: 341(M–HCl)$^+$, 284, 257, 245, 128.

EXAMPLE 15

2-(2-Methylphenyl)-3-morpholinoimidazo[2,1-a] isoquinoline (Compound 218) hydrochloride A solution of 5.5 g of 3-amino-2-(2-methylphenyl) imidazo[2,1-a]isoquinoline (Compound 3) in 50 ml of dry N,N-dimethylformamide was added dropwise to a solution of 1.8 g of sodium hydride in oil (prewashed with hexane) in 150 ml of dry N,N-dimethylformamide over 30 minutes under dry argon atmosphere at room temperature. After the mixture was stirred for further 1 hour, 3.2 g of bis(2-chloroethyl)ether was added dropwise. The mixture was stirred at room temperature for 2 hours, and then at 60° C. for 2 hours. The reaction mixture was poured into ice water, and extracted with ethyl acetate. The extract was washed with water and saturated saline, and dried over anhydrous magnesium sulfate. The drying agent was removed by filtration, and the solvent was removed under reduced pressure. The residue was purified by column chromatography on silica gel to give 2.0 g of 2-(2-methylphenyl)-3-morpholinoimidazo[2,1-a]isoquinoline (Compound 218) as a yellow oily material. To a solution of 2.0 g of the product in 80 ml of ether was added a saturated solution of hydrogen chloride in ether. Precipitated crystalline was collected by filtration, and washed with ethanol to give 1.1 g of the title compound as a yellowish white powder.

m.p.: 212.0–217.0° C.

Analysis Calcd.for $C_{22}H_{21}N_3O \cdot HCl \cdot 0.2H_2O$: C, 68.90%; H, 5.89%; N, 10.96%; Found: C, 68.87%; H, 5.94%; N, 10.92%.

IR(KBr): 3040, 2980, 2860, 2740, 2600, 1660, 1625, 1542, 1498, 1459, 1304, 1262, 1239, 1202, 1112, 919, 800, 750.

NMR(DMSO): 9.38–9.02(1H,m), 8.56(1H,d,J=7.0 Hz), 8.41–7.70(4H,m), 7.68–7.38(4H,m), 3.90–3.55(4H,m), 3.10–2.77(4H,m), 2.37(3H,s).

MS(EI)m/z: 343(M–HCl)$^+$, 284, 270, 257, 245, 128.

EXAMPLE 16

3-(4-Methylbenzylideneamino)-2-(2-methylphenyl)imidazo [2,1-a]isoquinoline (Compound 225)

To a solution of 5.0 g of 3-amino-2-(2-methylphenyl) imidazo[2,1-a]isoquinoline (Compound 3) in 50 ml of methanol was added 2.2 g of p-tolualdehyde. After the mixture was stirred at room temperature for 22 hours, it was poured into water and extracted with ethyl acetate. The extract was washed with water and saturated saline, and dried over anhydrous magnesium sulfate. The drying agent was removed by filtration, and the solvent was removed under reduced pressure. The residue was purified by column chromatography on silica gel, and recrystallization from ethyl acetate/petroleum ether gave 5.4 g of the title compound as yellow crystals.

m.p.: 159.5–160.0° C.

IR(KBr): 3050, 2930, 1603, 1572, 1515, 1480, 1458, 1378, 1228, 1173, 1088, 900, 791, 755, 690.

NMR(CDCL): 8.81–8.58(1H,m), 8.38(1H,d,J=7.0 Hz), 8.22(1H,s), 7.84–7.01(12H,m), 2.37(3H,s), 2.27(3H,s).

EXAMPLE 17

3-[(1-Bromo-2-naphthyl)methylideneamino]-2-(2-methylphenyl)imidazo[2,1-a]isoquinoline (Compound 228)

Example 16 was repeated except that 1-bromo-2-naphtoaldehyde was used in place of p-tolualdehyde, which gave the title compound as a yellow powder.

m.p.: 250.0–252.0° C.

IR(KBr): 3060, 3020, 2920, 1578, 1515, 1476, 1458, 1380, 1328, 1300, 1260, 1230, 1190, 1160, 972, 940, 893, 860, 810, 786,760, 730, 688.

NMR(CDCL): 8.94(1H,s), 8.82–8.60(1H,m), 8.40(1H,d, J=8.0 Hz), 8.36–8.10(2H,m), 7.87–7.30(11H,m), 7.10(1H, d,J=8.0 Hz), 2.30(3H,s).

EXAMPLE 18

2-(2-Methylphenyl)-3-propylideneaminoimidazo[2,1-a] isoquinoline (Compound 224)

Example 16 was repeated except that propylaldehyde was used in place of p-tolualdehyde, which gave the title compound as a brown oily material.

IR(Neat): 3070, 2980, 1642, 1611, 1516,1480,1458, 1380, 1218, 1183, 1138, 1090, 1030, 985, 893, 790, 745, 693.

NMR(CDCL): 8.84–8.55(1H,m), 8.18(1H,d,J=7.0 Hz), 7.78(1H,t,J=4.0 Hz), 7.78–7.19(7H,m), 7.02(1H,d,J=7.0 Hz), 2.60–2.08(2H,m), 2.27(3H,s), 1.08(3H,t,J=7.0 Hz).

EXAMPLE 19

2-(2-Ethylphenyl)-3-(4-methylbenzylideneamino)imidazo[2,1-a]isoquinoline (Compound 226)

Example 16 was repeated except that 3-amino-2-(2-ethylphenyl)imidazo[2,1-a]isoquinoline (Compound 59) was used in place of 3-amino-2-(2-methylphenyl)imidazo[2,1-a]isoquinoline, which gave the title compound as a yellow powder.

m.p.: 158.5–159.5° C.

IR(KBr): 2970, 2940, 2880, 1600, 1570, 1515, 1476, 1460, 1420, 1380, 1230, 1175, 1088, 970, 900, 812, 790, 765,742, 690.

NMR(CDCL): 8.97–8.67(1H,m), 8.46(1H,d,J=7.4 Hz), 8.30(1H,s), 7.91–7.09(12H,m), 2.68(2H,q,J=7.0 Hz), 2.39 (3H,s), 1.10(3H,t,J=7.0 Hz).

EXAMPLE 20

3-(4-Methylbenzylamino)-2-(2-methylphenyl)imidazo[2,1-a]isoquinoline (Compound 194)

To a solution of 4.3 g of 3-(4-methylbenzylideneamino)-2-(2-methylphenyl)imidazo[2,1-a]isoquinoline(Compound 225) in 50 ml of ethanol was added 0.9 g of sodium borohydride. After the mixture was refluxed for 2 hours, it was poured into water, and extracted with chloroform. The extract was washed with saturated saline, and dried over anhydrous magnesium sulfate. The drying agent was removed by filtration, and the solvent was removed under reduced pressure. The crude crystals were recrystallized from petroleum ether/chloroform to give 3.7 g of the title compound as pale yellow needles.

m.p.: 139.0–139.5° C.

IR(KBr): 3360, 3050, 2940, 2860, 1613, 1571, 1518, 1459, 1374, 1185, 898, 798, 750, 730.

NMR(CDCL): 8.87–8.60(1H,m), 7.95(1H,d,J=7.0 Hz), 7.75–6.94(12H,m), 4.13–3.89(2H,m), 3.71–3.44(1H,m), 2.37(3H,s), 2.30(3H,s).

EXAMPLE 21

3-Ethylamino-9-methoxy-2-(2-methylphenyl)imidazo[2,1-a]isoquinoline (Compound 167)

To a solution of 5.0 g of 3-amino-9-methoxy-2-(2-methylphenyl)imidazo[2,1-a]isoquinoline (Compound 26) in 100 ml of ethanol was added 3.0 ml of acetaldehyde, and the mixture was stirred at room temperature for 3 hours. After 3.3 g of sodium borohydride was added to the mixture and refluxed for 2 hours, the reaction mixture was poured into water, and extracted with ethyl acetate. The extract was washed with saturated saline, and dried over anhydrous magnesium sulfate. The drying agent was removed by filtration, and the solvent was removed under reduced pressure. The crude crystal was recrystallized from petroleum ether/ethyl acetate to give 5.0 g of the title compound as colorless needles.

m.p.: 153.0–154.0° C.

IR(KBr): 3240, 3070, 3040, 2960, 2930, 2900, 2850, 1618, 1585, 1568, 1520, 1506, 1473, 1436, 1396, 1379, 1340,1300, 1270, 1223, 1190, 1140, 1050, 1030, 912, 850, 822, 752, 718.

NMR(CDCL): 8.10(1H,d,J=2.0 Hz), 7.84(1H,d,J=7.0 Hz), 7.63(1H,d,J=8.0 Hz), 7.49–6.90(6H,m), 3.97(3H,s), 3.28–2.84(1H,br), 2.97(2H,q,J=7.0 Hz), 2.40(3H,s), 1.05 (3H,t,J=7.0 Hz).

EXAMPLE 22

Compounds obtained in the same manner as in Examples 8, 9, 10 and 21 are collectively shown below.

2-(2-Methylphenyl)-3-(propoxycarbonylmethyl)aminoimidazo[2,1-a]isoquinoline (Compound 156)

IR(Neat): 3450–3150, 3070, 2480, 2440, 1748, 1672, 1640, 1610, 1598–1550, 1520, 1459, 1398, 1378, 1195, 890,745.

NMR(CDCL): 8.75–8.54(1H,m), 8.00(1H,d,J=8.0 Hz), 7.75–7.20(7H,m), 7.01(1H,d,J=8.0 Hz), 4.00(2H,t,J=6.0 Hz), 3.64(2H,s), 2.40(3H,s), 1.80–1.27(2H,m), 0.85(3H,t,J=7.0 Hz).

3-Ethylamino-2-(2-methylphenyl)imidazo[2,1-a]isoquinoline (Compound 158) hydrochloride m.p.: 236.5–239.5° C.(dec.).

IR(KBr): 3160, 3050, 3000, 2940, 2890, 2560, 1660, 1625, 1603, 1567, 1550, 1492,1460,1424,1385, 1327,1305, 1237, 1152,796,755,720.

NMR(DMSO): 8.94–8.70(1H,m), 8.50(1H,d,J=6.0 Hz), 8.14–7.28(8H,m), 2.94(2H,q,J=7.0 Hz), 2.45(3H,s), 1.01 (3H,t,J=7.0 Hz).

3-Ethylamino-2-(2-methylphenyl)-7-propylimidazo[2,1-a]isoquinoline (Compound 163) hydrochloride m.p.: 185.0° C.(dec.).

IR(KBr): 3170, 3030, 2970, 2940, 2870, 2625, 1658, 1618, 1570, 1542, 1486, 1428, 1380, 1343, 1300, 1282, 1240, 1220, 1154, 1086,792, 750.

NMR(DMSO): 8.97(1H,dd,J=3.0 Hz,6.0 Hz), 8.78(1H,d, J=8.0 Hz), 8.03–7.17(7H,m), 3.10(2H,brt,J=7.0 Hz), 2.87 (2H,q,J=7.0 Hz), 2.41(3H,s), 1.98–1.38(2H,m), 1.02(6H,t, J=7.0 Hz).

3-Ethylamino-6-methoxymethyl-2-(2-methylphenyl)imidazo[2,1-a]isoquinoline (Compound 164)

m.p.: 115.0–116.5° C.

IR(KBr): 3330, 3080, 2980, 2930, 2900, 2860, 2830, 1644, 1610, 1580, 1559, 1523, 1482, 1450, 1395, 1375, 1339, 1278, 1240,1215, 1195, 1155, 1120, 1090, 1060, 1030, 982, 948, 872, 860, 845, 825, 755, 715, 700.

NMR(CDCL): 8.72–8.50(1H,m), 7.98–7.10(8H,m), 4.75 (2H,s), 3.47(3H,s), 3.20–2.75(3H,m), 2.40(3H,s), 1.25–0.90 (3H,m).

3-Ethylamino-7-hydroxy-2-(2-methylphenyl)imidazo[2,1-a]isoquinoline (Compound 165)

m.p.: 247.0–251.0° C.(dec.).

IR(KBr): 3480–3400, 3390, 3100, 2980, 2940, 2875, 2375, 1611, 1588, 1565, 1508, 1448, 1381, 1355, 1280, 1252, 1208, 1186, 1146, 1015,949,785,741.

NMR(DMSO): 10.30(1H,s), 8.10(1H,d,J=7.0 Hz), 7.90 (1H,brd,J=8.0 Hz), 7.69–7.20(6H,m), 7.00(1H,dd,J=2.0 Hz,8.0 Hz), 4.79(1H,brt,J=6.0 Hz), 3.05–2.70(2H,m), 2.40 (3H,s), 0.96(3H,t,J=7.0 Hz).

3-Ethylamino-6-methoxy-2-(2-methylphenyl)imidazo[2,1-a]isoquinoline (Compound 166)

IR(Neat): 3260, 3070, 2970, 2950, 2880, 1648, 1610, 1568, 1519, 1485, 1455, 1372,1338, 1286, 1228,1158, 1125, 1100,1044, 1030,984,860.

NMR(CDCL): 8.79–8.50(1H,m), 8.15–7.88(1H,m), 7.68–7.08(7H,m), 3.90(3H,s), 3.20–2.62(3H,m), 2.39(3H,s), 1.00(3H,t,J=7.0 Hz).

(hydrochloride m.p.: 202.0° C.(dec.)).

7-Benzyloxy-3-ethylamino-2-(2-methylphenyl)imidazo[2,1-a]isoquinoline (Compound 169)

m.p.: 128.0–129.0° C.

IR(KBr): 3225, 3050, 2950, 2900, 2850, 1610, 1585, 1565, 1555, 1520, 1500, 1489, 1450, 1395, 1378, 1332, 1305, 1260, 1189, 1176, 1145, 1080, 1060, 1050, 1024, 935, 775, 735, 715.

NMR(CDCL): 8.30(1H,brd,J=8.0 Hz), 7.90(1H,d,J=7.0 Hz), 7.65–7.20(11H,m), 7.00(1H,brd,J=8.0 Hz), 5.25(2H,s), 3.20–2.75(3H,m), 2.40(3H,s), 1.07(3H,m).

7-Ethoxycarbonyl-3-ethylamino-2-(2-methylphenyl)imidazo[2,1-a]isoquinoline (Compound 173)

IR(KBr): 3380, 3070, 2980, 2940, 2880, 1718, 1637, 1600, 1557, 1515, 1482, 1450,1370,1310,1260, 1210,1195, 1119, 1022,925,790.

NMR(CDCL): 8.96(1H,dd,J=2.0 Hz,8.0 Hz), 8.32(1H,d, J=8.0 Hz), 8.23(1H,dd,J=2.0 Hz,8.0 Hz), 8.02(1H,d,J=8.0 Hz), 7.62(1H,t,J=8.0 Hz), 7.58–7.22(4H,m), 4.50(2H,q,J= 7.0 Hz), 3.13–2.70(1H,br), 2.98(2H,q,J=7.0 Hz), 2.42(3H,s), 1.47(3H,t,J=7.0 Hz), 1.07(3H,t,J=7.0 Hz).

3-Ethylamino-2-(2-trifluoromethylphenyl)imidazo[2,1-a] isoquinoline (Compound 175)

m.p.: 100.5–101.5° C.

IR(KBr): 3230, 3060, 2980, 2940, 2910, 2860, 1639, 1610, 1590, 1570, 1520, 1505, 1483, 1457, 1420, 1390, 1373, 1349, 1320, 1275, 1260, 1190, 1168, 1156, 1125, 1115, 1100, 1053, 1032,980,950,900,845,792,754,697.

NMR(CDCL): 8.79–8.45(1H,m), 8.10–7.30(7H,m), 7.88 (1H,d,J=7.6 Hz), 7.01(1H,d,J=7.6 Hz), 3.20–2.63(3H,m), 1.02(3H,t,J=7.0 Hz).

3-Ethylamino-6-methoxy-2-(3-methyl-2-thienyl)imidazo[2, 1-a]isoquinoline (Compound 176)

m.p.: 142.0–143.0° C.

IR(KBr): 3330, 3090, 3040, 2980, 2950, 2925, 2880, 1648,1590, 1520, 1481, 1471, 1441, 1378,1341,1323, 1289, 1230, 1214, 1186, 1160, 1135, 1100, 1074, 1020, 990, 968, 861, 830, 773, 732, 699.

NMR(CDCL): 8.83–8.52(1H,m), 8.20–7.89(1H,m), 7.79–7.48(2H,m), 7.41(1H,s), 7.24(1H,d,J=5.0 Hz), 6.96 (1H,d,J=5.0 Hz), 3.96(3H,s), 3.32–2.76(3H,m), 2.51(3H,s), 1.17(3H,t,J=7.0 Hz).

2-(2-Chloro-3-methyl-4-thienyl)-3-ethylaminoimidazo[2,1-a]isoquinoline (Compound 179)

m.p.: 80.5–81.0° C.

IR(KBr): 3250, 3060, 2960, 2850, 1635, 1608, 1581, 1516, 1486, 1443, 1375, 1340, 1230, 1188, 1136, 1004,960, 892,776,732,688.

NMR(CDCL): 8.85–8.51(1H,m), 7.92(1H,d,J=7.0 Hz), 7.82–7.35(3H,m), 7.21(1H,s), 7.06(1H,d,J=7.0 Hz), 3.31–2.78(3H,m), 2.38(3H,s), 1.14(3H,t,J=7.0 Hz).

3-(2-Methoxyethyl)amino-2-(2-methylphenyl)imidazo[2,1-a]isoquinoline (Compound 180) hydrochloride m.p.: 206.0–208.0° C.(dec.).

IR(KBr): 3160, 3050, 2940, 2610, 1662, 1625, 1605, 1570, 1550, 1470–1435, 1430, 1330, 1310, 1241, 1200, 1145, 1120, 958, 789, 752.

NMR(CDCL): 16.10–15.60(1H,br), 9.60–9.38(1H,m), 8.55(1H,d,J=8.0 Hz), 7.91–7.62(3H,m), 7.58–7.30(1H,m), 7.42(1H,d,J=8.0 Hz), 7.10–6.85(3H,m), 3.48–2.85(4H,m), 3.10(3H,s), 2.40(3H,s).

6-Isopentyl-2-(2-methylphenyl)-3-propylaminoimidazo[2, 1-a]isoquinoline (Compound 181)

m.p.: 126.5–127.5° C.

IR(KBr): 3210, 3070, 3025, 2960, 2940, 2875, 1640, 1610, 1575, 1520, 1495, 1480,1465,1455,1390, 1368, 1360, 1340,1240,1154,760.

NMR(CDCL): 8.85–8.55(1H,m), 7.90–7.10(8H,m), 3.20–2.70(5H,m), 2.40(3H,s), 1.86–1.25(5H,m), 1.05(6H,d, J=6.0 Hz), 0.85(3H,t,J=7.0 Hz).

6-Methoxy-2-(2-methylphenyl)-3-propylaminoimidazo[2, 1-a]isoquinoline (Compound 182)

m.p.: 106.0° C.

IR(KBr): 3250, 3070, 3030, 2970, 2930, 2840, 1650, 1610, 1589, 1572, 1522, 1482, 1471, 1452, 1412, 1378, 1338, 1308, 1279,1226, 1192, 1152, 1128, 1100, 1068, 990, 863, 790, 758, 715, 702.

NMR(CDCL): 8.71–8.45(1H,m), 8.19–7.91(1H,m), 7.71–7.05(7H,m), 3.98(3H,s), 3.29–2.59(3H,m), 2.38(3H,s), 1.69–1.10(2H,m), 0.86(3H,t,J=7.0 Hz).

3-Isopropylamino-2-(2-methylphenyl)imidazo[2,1-a] isoquinoline(Compound 184) hydrochloride m.p.: 210.0–214.5° C.

IR(KBr): 3450, 3220, 3050, 2990, 2940, 2800, 2725, 1663, 1625, 1606, 1570, 1549, 1498, 1460, 1428, 1385, 1370, 1332, 1238, 1175, 962, 899, 792, 750.

NMR(METH): 8.79–8.37(2H,m), 8.37–7.30(8H,m), 3.41–2.94(1H,m), 2.42(3H,s), 1.07(6H,d,J=7.0 Hz).

2-(2-Methylphenyl)-3-[(3-methylthiopropyl)amino]imidazo [2,1-a]isoquinoline (Compound 185)

IR(Neat): 3270, 3070, 2960, 2925, 2860, 1640, 1610, 1568, 1518, 1480, 1455, 1374,1260,1183,1135, 1092, 1042, 950,893,787,745,690.

NMR(CDCL): 8.78–8.52(1H,m), 7.92(1H,d,J=7.0 Hz), 7.80–7.40(3H,m), 7.28(4H,s), 7.02(1H,d,J=7.0 Hz), 3.31–2.79(3H,m), 2.42(2H,t,J=7.0 Hz), 2.38(3H,s), 1.98 (3H,s), 1.92–1.50(2H,m).

2-(2-Methylphenyl)-3-[3-(methylsulfinyl)propylamino] imidazo[2,1-a]isoquinoline (Compound 186)

IR(Neat): 3300, 3070, 2960, 2860, 1640, 1610, 1580, 1520, 1480, 1458, 1373, 1260, 1216, 1185, 1095, 1020, 940, 890, 790, 745.

NMR(CDCL): 8.78–8.52(1H,m), 7.92(1H,d,J=7.0 Hz), 7.847.20(7H,m), 7.08(1H,d,J=7.0 Hz), 3.50–2.80(3H,m), 2.70–2.35(2H,m), 2.40(6H,s), 2.10–1.15(2H,m).

3-Isopentylamino-2-(2-methylphenyl)imidazo[2,1-a] isoquinoline (Compound 188)

m.p.: 93.0–93.5° C.

IR(KBr): 3300, 3080, 3040, 2960, 2940, 2880, 1638, 1615, 1590, 1576, 1515, 1476, 1460, 1375, 1190, 1092, 900,795, 772,738.

NMR(CDCL): 8.80–8.52(1H,m), 7.90(1H,d,J=7.0 Hz), 7.72–7.19(7H,m), 7.00(1H,d,J=7.0 Hz), 3.12–2.73(3H,m), 2.40(3H,s), 1.73–1.05(3H,m), 0.80(6H,d,J=6.0 Hz).

3-Isopentylamino-2-(2,4-dimethylphenyl)imidazo[2,1-a] isoquinoline (Compound 189)

IR(Neat): 3250, 3070, 2970, 2940, 2870, 1640, 1612, 1582, 1505, 1485, 1456, 1372,1265,1237,1185, 1140,1094, 894,786,745.

NMR(CDCL): 8.86–8.50(1H,m), 7.88(1H,d,J=7.0 Hz), 7.80–6.82(7H,m), 3.10–2.64(3H,m), 2.37(6H,s), 1.55–1.05 (3H,m), 0.80(6H,d,J=6.0 Hz).

(hydrochloride m.p.: 215.0–217.5° C.).

3-Cyclopentylamino-2-(2-methylphenyl)imidazo[2,1-a] isoquinoline (Compound 190)

IR(KBr): 3300, 3080, 2975, 2890, 1640, 1613, 1569, 1521, 1484, 1460, 1377, 1186, 1090, 898,790,741.

NMR(CDCL): 8.78–8.50(1H,m), 7.93(1H,d,J=7.0 Hz), 7.70–7.16(7H,m), 6.98(1H,d,J=7.0 Hz), 3.60–3.22(1H,m), 3.11–2.73(1H,br), 2.40(3H,s), 1.80–1.11(8H,m).

3-Hexylamino-2-(2-methylphenyl)imidazo [2,1-a] isoquinoline (Compound 191)

IR(Neat): 3240, 3060, 2960, 2930, 2860, 1635, 1608, 1582–1565, 1518, 1480, 1456, 1372, 1260, 1219–1210, 1181, 893, 788, 748.

NMR(CDCL): 8.82–8.60(1H,m), 7.92(1H,d,J=7.0 Hz), 7.75–7.25(7H,m), 7.06(1H,d,J=7.0 Hz), 3.30–2.75(3H,m), 2.40(3H,s), 1.60–0.60(11H,m).

(hydrochloride m.p.: 172.0–175.0° C.(dec.)).

3-[(1-Bromo-2-naphthyl)methylamino]-2-(2-methylphenyl) imidazo[2,1-a]isoquinoline (Compound 195)

m.p.: 129.0–130.0° C.

IR(KBr): 3250, 3050, 2940, 2830, 1639, 1610, 1570, 1520, 1498, 1483, 1455, 1375, 1325, 1260, 1230, 1213, 1183, 1135, 1097, 1026, 965, 896, 865, 815, 783, 760,715.

NMR(CDCL): 8.80–8.50(1H,m), 8.33–8.03(1H,m), 7.93 (1H,d,J=7.0 Hz), 7.81–7.34(7H,m), 7.12–6.87(6H,m), 4.444.23(2H,m), 4.18–3.90(1H,m), 2.17(3H,s).

3-[(3-Methyl-2-benz[b]furyl)methylamino]-2-(2-methylphenyl)imidazo[2,1-a]isoquinoline (Compound 196)

IR(KBr): 3390, 3060, 2940, 2860, 1610, 1520, 1480, 1458, 1374, 1328, 1265, 1230,1178,1117,790,740.

NMR(CDCL): 8.78–8.54(1H,m), 7.90(1H,d,J=8.0 Hz), 7.70–7.03(11H,m), 6.98(1H,d,J=8.0 Hz), 4.12(2H,brd,J=5.0 Hz), 3.90–3.57(1H,br), 2.26(3H,s), 1.83(3H,s).

7-Bromo-3-diethylamino-2-(2-methylphenyl)imidazo[2,1-a]isoquinoline (Compound 200)

IR(Neat): 3080, 2980, 2940, 2860, 1635, 1597, 1556, 1515, 1490, 1473, 1436, 1371, 1348, 1218, 1104, 897,780.

NMR(CDCL): 8.82–8.45(1H,m), 8.30–7.10(8H,m), 2.95 (4H,q,J=7.0 Hz), 2.35(3H,s), 0.98(6H,t,J=7.0 Hz).

(hydrochloride m.p.: 186.0–187.5° C.).

3-[N-(2-Chloroethyl)-N-ethylamino]-2-(2-methylphenyl) imidazo[2,1-a]isoquinoline (Compound 202) hydrochloride m.p.: 169.0–169.5° C.

IR(KBr): 3050, 2980, 2920, 2850, 2570, 2350, 1740, 1651, 1618, 1540, 1493, 1456, 1419, 1380, 1315, 1280, 1240, 1159, 1099, 1030, 894, 804, 747.

NMR(DMSO): 9.50–9.19(1H,m), 8.59(1H,d,J=7.0 Hz), 8.39–7.75(4H,m), 7.72–7.21(4H,m), 3.70(2H,t,J=5.0 Hz), 3.50–2.90(4H,m), 2.40(3H,s), 1.09(3H,t,J=7.0 Hz).

3-[N-Ethyl-N-[2-(N,N-diethylamino)ethyl]amino]-2-(3-ethyl-2-thienyl)imidazo[2,1-a] isoquinoline (Compound 203)

IR(Neat): 3070, 2980, 2940, 2870, 2810, 1638, 1610, 1580, 1520, 1482, 1458, 1372, 1345, 1202, 1155, 1068,905, 890, 788, 735, 698.

NMR(CDCL): 8.83–8.58(1H,m), 8.12(1H,d,J=7.0 Hz), 7.81–7.44(3H,m), 7.31–6.95(3H,m), 3.36–2.29(12H,m), 1.25(3H,t,J=7.0 Hz), 1.02(3H,t,J=7.0 Hz), 0.92(6H,t,J=7.0 Hz).

3-[N-Ethyl-N-(2-methoxyethyl)amino]-2-(2-methylphenyl) imidazo[2,1-a]isoquinoline (Compound 205) hydrochloride m.p.: 156.5–159.0° C.

IR(KBr): 3040, 2990, 2940, 2850, 2575, 2400, 2320, 1783–1769, 1655, 1620, 1605, 1541, 1499, 1455, 1420, 1388, 1375, 1350, 1330, 1300, 1288, 1238, 1198, 1115, 1110, 1072, 1015, 920–855, 808, 765, 751,725, 695.

NMR(CDCL): 10.00–9.72(1H,m), 8.50(1H,d,J=8.0 Hz), 8.05–7.78(3H,m), 7.60(1H,d,J=8.0 Hz), 7.50–7.25(4H,m), 3.55–2.85(6H,m), 3.25(3H,s), 2.50(3H,s), 1.05(3H,t,J=7.0 Hz).

3-(N-Ethyl-N-propylamino)-2-(2-fluorophenyl)imidazo[2,1-a]isoquinoline (Compound 206)

IR(Neat): 3060, 2960, 2940, 2875, 1625, 1610, 1565, 1520, 1495, 1480, 1456, 1418, 1378, 1260, 1220, 1175, 1150, 1115, 1090, 1030, 891, 820,790,750, 696.

NMR(CDCL): 8.82–8.10(1H,m), 8.03(1H,d,J=7.2 Hz), 7.90–7.20(7H,m), 7.07(1H,d,J=7.2 Hz), 3.28–2.75(4H,m), 1.65–1.10(2H,m), 1.04(3H,t,J=7.0 Hz), 0.81(3H,t,J=7.0 Hz).

3-(N-Ethyl-N-propylamino)-6-isopentyl-2-(2-methylphenyl)imidazo [2,1-a]isoquinoline (Compound 208) hydrochloride m.p.: 149.0–151.5° C.

IR(KBr): 3060, 3020, 2960, 2940, 2875, 2550, 2275, 1780–1770, 1651, 1615, 1605, 1539, 1495, 1465, 1455, 1422, 1384, 1370, 1330, 1275, 1230, 1170, 1120–1060, 1040, 850, 825, 775, 723.

NMR(CDCL): 9.95–9.70(1H,m), 8.20–7.78(4H,m), 7.50–7.25(4H,m), 3.30–2.75(6H,m), 2.50(3H,s), 2.00–1.30 (5H,m), 1.10(3H,t,J=8.0 Hz), 1.10(6H,d,J=6.0 Hz), 0.90(3H, t,J=7.0 Hz).

3-(N-Ethyl-N-propylamino)-2-(3-methylphenyl)imidazo[2,1-a]isoquinoline (Compound 211) hydrochloride m.p.: 152.5–156.0° C.

IR(KBr): 3060, 2980, 2940, 2860, 2600, 1656, 1621, 1605, 1543, 1497, 1458, 1420, 1385, 1335, 1238, 1172, 1110–1088, 890, 800, 750, 692.

NMR(DMSO): 9.70–9.37(1H,m), 8.53(1H,d,J=7.0 Hz), 8.40–7.24(8H,m), 3.25(4H,m), 2.46(3H,s), 1.70–1.10(2H, m), 1.10(3H,t,J=7.0 Hz), 0.79(3H,t,J=7.0 Hz).

3-(N-Ethyl-N-propylamino)-2-(3-methyl-2-thienyl)imidazo [2,1-a]isoquinoline (Compound 212) hydrochloride m.p.: 146.0–148.5° C.

IR(KBr): 3050, 2970, 2930, 2870, 2660–2590, 2330, 1790, 1655, 1620, 1545, 1459, 1425, 1389, 1320, 1236, 1180, 1065, 890, 800, 750.

NMR(DMSO): 9.38–9.11(1H,m), 8.49(1H,d,J=7.0 Hz), 8.32–7.74(5H,m), 7.18(1H,d,J=5.0 Hz), 3.17(2H,q,J=7.0 Hz), 3.00(2H,t,J=7.0 Hz), 2.38(3H,s), 1.73–1.03(2H,m), 1.09(3H,t,J=7.0 Hz), 0.80(3H,t,J=7.0 Hz).

3-[N-Ethyl-N-(3-methylthiopropyl)amino]-2-(2-methylphenyl)imidazo[2,1-a]isoquinoline (Compound 214)

IR(Neat): 3070, 2980, 2940, 2860, 1639, 1612, 1559, 1520, 1482, 1457, 1376, 1234, 1156, 1045,954,895,792,750, 700.

NMR(CDCL): 8.82–8.55(1H,m), 8.02(1H,d,J=7.0 Hz), 7.75–7.21(7H,m), 7.06(1H,d,J=7.0 Hz), 3.03(2H,q,J=7.0 Hz), 2.99(2H,t,J=7.0 Hz), 2.45(2H,t,J=7.0 Hz), 2.35(3H,s), 1.98(3H,s), 1.98–1.47(2H,m), 1.06(3H,t,J=7.0 Hz).

3-(N-Ethyl-N-isopentylamino)-2-(2-ethylphenyl)imidazo[2,1-a]isoquinoline (Compound 216) hydrochloride m.p.: 159.5–161.0° C.

IR(KBr): 3060, 2970, 2940, 2880, 2600, 1660, 1621, 1550, 1494, 1465, 1424, 1390, 1339, 1290, 1250, 1229, 1165, 1100, 890,800,750.

NMR(DMSO): 9.20–8.98(1H,m), 8.49(1H,d,J=7.0 Hz), 8.33–7.74(4H,m), 7.64–7.38(4H,m), 3.25–2.76(6H,m), 1.52–0.96(9H,m), 0.80(6H,d,J=6.0 Hz).

3-[N-Ethyl-N-(4-methylbenzyl)amino]-2-(2-methylphenyl) imidazo[2,1-a]isoquinoline (Compound 219)

IR(Neat): 3080, 3040, 2990, 2940, 2860, 1645, 1612, 1560, 1519, 1482, 1458, 1380, 792, 750.

NMR(CDCL): 8.80–8.50(1H,m), 8.05(1H,d,J=7.0 Hz), 7.80–7.20(7H,m), 7.20–6.89(5H,m), 4.05(2H,s), 2.98(2H,q, J=7.0 Hz), 2.26(6H,s), 1.00(3H,s).

(hydrochloride m.p.: 116.0–119.0° C.).

3-[N-Ethyl-N-(4-methylbenzyl)amino]-2-(2-ethylphenyl) imidazo[2,1-a]isoquinoline (Compound 220)

IR(Neat): 3070, 3040, 2990, 2940, 2890, 1639, 1610, 1558, 1519, 1482, 1455, 1420, 1372, 1270, 1230, 1160, 1020, 896, 840,790,700.

NMR(CDCL): 8.82–8.50(1H,m), 8.00(1H,d,J=7.4 Hz), 7.78–6.88(12H,m), 4.02(2H,s), 2.98(2H,q,J=7.0 Hz), 2.62 (2H,q,J=7.0 Hz), 2.26(3H,s), 1.22(3H,t,J=7.0 Hz), 1.00(3H, t,J=7.0 Hz).

3-(N-Allyl-N-ethylamino)-2-(2-methylphenyl)imidazo[2,1-a]isoquinoline (Compound 222) hydrochloride m.p.: 175.0–178.0° C.

IR(KBr): 3100, 2990, 2580, 2400–2310, 1750, 1655, 1620, 1542, 1498, 1420, 1233, 1100,1082, 1010,928,891, 803,750, 692.

NMR(DMSO): 9.34–8.93(1H,m), 8.53(1H,d,J=7.0 Hz), 8.40–7.78(4H,m), 7.49(4H,s), 6.18–5.52(1H,m), 5.38–4.88 (2H,m), 3.68(2H,d,J=6.0 Hz), 3.00(2H,q,J=7.0 Hz), 2.40 (3H,s), 1.00(3H,t,J=7.0 Hz).

3-Ethylamino-2-(2-methylphenyl)imidazo[1,2-a]thieno[3,2-c]pyridine (Compound 340) hydrochloride m.p.: 192.0° C.(sublimation).

IR(KBr): 3150, 3060, 3030, 2970, 2910, 2870, 2770, 2710, 2650, 2600, 1650, 1620, 1600, 1533, 1495, 1422, 1379, 1315, 1290, 1243, 1215, 1162, 1086, 1008, 959,763, 721.

NMR(DMSO): 8.41(1H,d,J=5.8 Hz), 8.25(1H,d,J=4.0 Hz), 8.08–7.86(2H,m), 7.63–7.20(4H,m), 2.97(2H,q,J=7.8 Hz), 2.48(3H,s), 1.01(3H,t,J=7.8 Hz).

3-Ethylamino-2-(2-methylphenyl)imidazo[1,2-a]thieno[2,3-c]pyridine (Compound 345) hydrochloride m.p.: 237.0° C.(dec.).

IR(KBr): 3140, 3050, 2960, 2910, 2860, 2780, 2700, 2650, 2550, 1653, 1624, 1600, 1545, 1525, 1500, 1442, 1414, 1385,1353, 1323, 1280, 1248, 1205, 1150, 1095, 1057, 1040, 920, 840, 792, 750, 733, 715.

NMR(DMSO): 8.82(1H,d,J=7.0 Hz), 8.32(1H,d,J=5.0 Hz), 7.94(1H,d,J=7.0 Hz), 7.80(1H,d,J=5.0 Hz), 7.66–7.33 (4H,m), 2.88(2H,q,J=7.0 Hz), 2.40(3H,s), 0.98(3H,t,J=7.0 Hz).

3-(N-Ethyl-N-propylamino)-2-(2-methylphenyl)imidazo[1,2-a]thieno[2,3-c]pyridine (Compound 356) hydrochloride m.p.: 185.0–188.5° C.

IR(KBr): 3040, 2960, 2930, 2860, 2530, 2250, 1650, 1613, 1570, 1538, 1490, 1457,1410,1386,1350, 1320,1278, 1242,1213, 1173,1080, 1038,803,762,730.

NMR(DMSO): 8.70(1H,d,J=7.0 Hz), 8.48(1H,d,J=5.0 Hz), 8.10(1H,d,J=7.0 Hz), 7.93(1H,d,J=5.0 Hz), 7.55(4H,s), 3.10(2H,q,J=7.0 Hz), 2.93(2H,t,J=7.0 Hz), 2.44(3H,s), 1.78–1.02(2H,m), 1.08(3H,t,J=7.0 Hz), 0.78(3H,t,J=7.0 Hz).

EXAMPLE 23

3-Amino-9-methoxy-2-(2-methylphenyl)-5,6-dihydroimidazo[2,1-a]isoquinoline (Compound 103)

To a solution of 8.4 g of 3-amino-9-methoxy-2-(2-methylphenyl)imidazo[2,1-a]isoquinoline(Compound 26) in 100 ml of ethanol was added 1.0 g of palladium on activated carbon (Pd 10%). After introduction of hydrogen, the mixture was stirred at room temperature for 48 hours. The reaction mixture was filtered, and the filtrate was evaporated in vacuo. Resultant residue was purified by column chromatography on silica gel and recrystallized from ethyl acetate/isopropyl ether to give 1.5 g of the title compound as a pale yellow powder.

m.p.: 159.5–160.0° C.

IR(KBr): 3460, 3340, 3200, 3070, 3020, 2930, 2900, 2850, 1628, 1618, 1572, 1540, 1498, 1470, 1458, 1440, 1358, 1322, 1283, 1230, 1180, 1035,820,770.

NMR(CDCL): 7.58(1H,d,J=3.0 Hz), 7.46–7.20(4H,m), 7.13(1H,d,J=9.0 Hz), 6.77(1H,dd,J=3.0 Hz,9.0 Hz), 3.96 (2H,t,J=7.0 Hz), 3.84(3H,s), 3.20(2H,brs), 3.04(2H,t,J=7.0 Hz), 2.40(3H,s).

EXAMPLE 24

3-Amino-9-hydroxy-2-(2-methylphenyl)imidazo[2,1-a]isoquinoline (Compound 22).

To a solution of 5.0 g of 3-amino-9-benzyloxy-2-(2-methylphenyl)imidazo[2,1-a]isoquinoline (Compound 40) in 100 ml of ethanol was added 0.5 g of palladium on activated carbon (Pd 10%). After introduction of hydrogen, the mixture was stirred at room temperature for 24 hours. The reaction mixture was filtered, and the filtrate was evaporated in vacuo. Resultant residue was purified by column chromatography on silica gel and recrystallized from water/methanol to give 3.2 g of the title compound as pale yellow needles.

m.p.: 240.0–243.0° C.(dec.).

IR(KBr): 3400, 3320, 3000–2450, 1610, 1490, 1455, 1420, 1395, 1325, 1255, 1232, 1200, 1130, 1080, 1030, 920, 865, 815, 758,720.

NMR(DMSO): 10.00(1H,brs), 7.92(1H,d,J=7.0 Hz), 7.77 (1H,d,J=2.0 Hz), 7.68(1H,d,J=8.4 Hz), 7.65–6.90(5H,m), 7.09(1H,d,J=7.0 Hz), 4.92(2H,brs), 2.45(3H,s).

Pharmaceutical formulation 1: Powders containing 3-amino-5-methyl-2-(2-methylphenyl)imidazo[1,2-a]thieno[3,2-c]pyridine (Compound 236) as an active ingredient Five grams of 3-amino-5-methyl-2-(2-methylphenyl)imidazo[1,2-a]thieno[3,2-c]pyridine (Compound 236) and 95 g of lactose were admixed uniformly to give the powders.

Pharmaceutical formulation 2: Granules containing 3-amino-5-methyl-2-(2-methylphenyl)imidazo[1,2-a]thieno[3,2-c]pyridine (Compound 236) as an active ingredient Five grams of 3-amino-5-methyl-2-(2-methylphenyl)imidazo[1,2-a]thieno[3,2-c]pyridine (Compound 236), 36 g of lactose, 31 g of corn starch, and 22 g of crystalline cellulose were admixed, and then the resultant powder was granulated by kneading it with 4 g of hydroxypropylcellulose in 100 ml of water, and the resultant grains were dried for 4 hours at 50° C. The dried grains were sifted through a 12 mesh sieve, and mixed with 2 g of magnesium stearate to obtain granules.

Pharmaceutical formulation 3: Tablets containing 3-amino-5-methyl-2-(2-methylphenyl)imidazo[1,2-a]thieno[3,2-c]pyridine (Compound 236) as an active ingredient Five grams of 3-amino-5-methyl-2-(2-methylphenyl)imidazo[1,2-a]thieno[3,2-c]pyridine (Compound 236), 35 g of lactose, 32 g of corn starch, and 24 g of crystalline cellulose were admixed, and then the resultant powder was granulated by kneading it with an aqueous solution containing 2 g of hydroxypropylcellulose, and then the granules were dried for 4 hours at 50° C. After mixing with 2 g of magnesium stearate, the granules were compressed into tablets, each weighing 200 mg, using a tablet machine.

Pharmaceutical formulation 4: Capsules containing 3-amino-5-methyl-2-(2-methylphenyl)imidazo[1,2-a]thieno[3,2-c]pyridine (Compound 236) as an active ingredient Five grams of 3-amino-5-methyl-2-(2-methylphenyl)imidazo[1,2-a]thieno[3,2-c]pyridine (Compound 236), 38 g of lactose, 33 g of corn starch, 22 g of crystalline cellulose, and 2 g of magnesium stearate were admixed. The mixture was filled into hard gelatin capsules, each weighing 200 mg, using a capsule filler.

Pharmaceutical formulation 5: Syrups containing 3-amino-5-methyl-2-(2-methylphenyl)imidazo[1,2-a]thieno[3,2-c]pyridine (Compound 236) as an active ingredient One gram of 3-amino-5-methyl-2-(2-methylphenyl)imidazo[1,2-a]thieno[3,2-c]pyridine (Compound 236), 30 g of sucrose, 25 g of D-sorbitol(70 w/v %), 30 mg of ethyl p-hydroxybenzoate, and 15 mg of propyl p-hydroxybenzoate were dissolved in 60 g of warm water. After cooling, a flavouring dissolved in 150 mg of glycerin and 500 mg of ethanol(96%) was added thereto. Water was added to the mixture to give 100 ml of syrups.

What is claimed is:

1. Fused imidazo[1,2-a]pyridines represented by the following general formula (I):

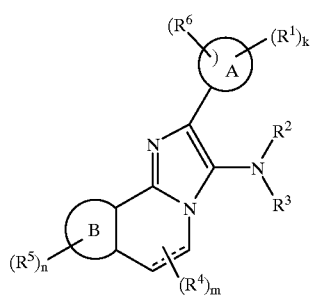

(I)

wherein ring A represents an aromatic ring selected from benzene, thiophene, furan or pyrrole ring; ring B represents benzene;

$R^1$ is a hydroxyl group, halogen atom, lower alkyl group which may be halogenated, lower alkoxy group or acyloxy group;

k represents 0, 1, 2 or 3;

$R^2$ and $R^3$ may be the same or different and each represents a hydrogen atom, alkenyl group, acyl group, alkoxycarbonyl group or lower alkyl group which may have substituent(s) selected from the group consisting of 1) halogen atom, 2) hydroxyl group, 3) lower alkoxy group, 4) lower alkylthio group, 5) alkylsulfinyl group, 6) alkoxycarbonyl group, 7) carbamoyl group, 8) alkylamino group and 9) aryl group, or $R^2$ and $R^3$, together with the nitrogen atom to which they are attached, may form a 5- or 6-membered monocyclic heterocyclic ring, or $R^2$ and $R^3$, together with the nitrogen atom to which they are attached, may form an alkylideneamino group or arylalkylideneamino group; $R^4$ and $R^5$ each independently represent a halogen atom, cyano group, hydroxyl group, carboxyl group, alkoxycarbonyl group, acyl group, alkylamino group, aryl group, acyloxy group, carbamoyloxy group, lower alkyl group which may have substituent(s) selected from the group consisting of 1) hydroxyl group, 2) lower alkoxy group, 3) aryl group and 4) aryloxy group, lower alkoxy group which may have substituent(s) selected from the group consisting of 1) hydroxyl group, 2) lower alkoxy group, 3) lower alkoxycarbonyl group and 4) aryl group, or lower alkylthio group which may be substituted with an aryl group;

$R^6$, which may be present or absent, is selected from the group consisting of a halogen atom, lower alkyl group which may be halogenated, or lower alkoxy group;

m represents 0, 1 or 2;

n represents 0, 1 or 2;

the dotted line, together with the solid line, represents a single or double bond, provided that plural $R^4$s may be attached to the same carbon atom, or a pharmaceutically acceptable salt or solvate thereof.

2. The compounds of claim 1 wherein $R^2$ and $R^3$ may be the same or different and each represent hydrogen atom, alkenyl group or lower alkyl group which may have substituent(s) selected from the group consisting of halogen atom, lower alkoxy group, lower alkylthio group and aryl group, or $R^2$ and $R^3$, together with the nitrogen atom to which they are attached, may form a 5- or 6-membered monocyclic heterocyclic ring.

3. The compounds of claim 1 wherein
ring A is an aromatic ring selected from benzene, thiophene, furan or pyrrole ring;
$R^1$ is a halogen atom or lower alkyl group which may be halogenated or lower alkoxy group;
k is 1 or 2;
$R^2$ is hydrogen atom;
$R^3$ is hydrogen atom, alkenyl group or lower alkyl group which may have substituent(s) selected from the group consisting of halogen atom, lower alkoxy group, lower alkylthio group and aryl group.

4. The compounds of claim 3 wherein the dotted line, together with the solid line, represents a double bond.

5. The compounds of claim 4 wherein ring A and substituent(s) on the ring represent the following formula:

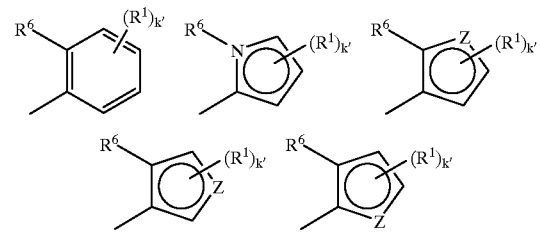

wherein $R^1$ and $R^6$ are each independently halogen atom, lower alkyl group which may be halogenated or lower alkoxy group; k' is 0 or 1; Z is a hetero atom selected from sulfur, oxygen or nitrogen atom.

6. The compounds of claim 5 wherein at least one of $R^1$ and $R^6$ is lower alkyl group.

7. The compounds of claim 6 wherein $R^6$ is lower alkyl group having 1 or 2 carbon atoms; $R^4$ and $R^5$ are each independently a substituent selected from halogen atom, lower alkyl group, lower alkoxy group or lower alkylthio group.

8. The compounds of claim 1 wherein
ring A is an aromatic ring selected from benzene, thiophene, furan or pyrrole ring represented by the following formula:

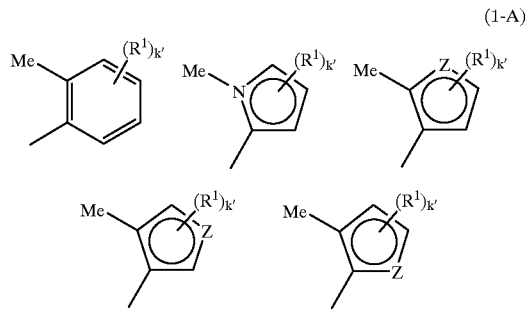

(1-A)

wherein k' is 0 or 1; Z is a hetero atom selected from a sulfur, oxygen or nitrogen atom;
the substitutent $R^1$ on the ring is halogen atom, lower alkyl group which may be halogenated, or lower alkoxy group;
$R^2$ and $R^3$ are hydrogen atoms;
$R^4$ and $R^5$ are independently a substituent selected from a halogen atom, lower alkyl group, lower alkoxy group or lower alkylthio group;

m is 0, 1 or 2,;

n is 0, 1 or 2;

and the dotted line, together with the solid line, represents a double bond.

9. Pharmaceutical compositions containing the compound defined in claim 1, in association with a pharmaceutically acceptable carrier.

10. Pharmaceutical compositions according to claim 9 comprising an amount of the compound effective for the treatment of gastrointestinal diseases.

11. Pharmaceutical compositions according to claim 9 comprising an amount of the compound effective for treating an ulcer.

12. A method of treating a patient suffering from gastrointestinal diseases including ulcer, which comprises administering an effective amount of a compound defined in claim 1 to the patient.

* * * * *